United States Patent
Kelley et al.

(10) Patent No.: US 12,350,247 B2
(45) Date of Patent: Jul. 8, 2025

(54) USE OF APE1/REF-1 INHIBITORS FOR TREATMENT OF RETINAL DISEASES

(71) Applicant: Indiana University Research and Technology Corporation, Indianapolis, IN (US)

(72) Inventors: Mark R. Kelley, Zionsville, IN (US); Melissa L. Fishel, Fishers, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 18/295,907

(22) Filed: Apr. 5, 2023

(65) Prior Publication Data
US 2023/0293471 A1  Sep. 21, 2023

Related U.S. Application Data

(60) Division of application No. 17/026,671, filed on Sep. 21, 2020, now Pat. No. 11,648,226, which is a (Continued)

(51) Int. Cl.
*A61K 31/201* (2006.01)
*A61K 31/165* (2006.01)
(Continued)

(52) U.S. Cl.
CPC .......... *A61K 31/201* (2013.01); *A61K 31/165* (2013.01); *A61K 31/18* (2013.01);
(Continued)

(58) Field of Classification Search
CPC ........ A61P 27/00; A61P 35/00; A61K 31/201; A61K 31/165; A61K 31/18; A61K 3/192;
(Continued)

(56) References Cited

U.S. PATENT DOCUMENTS 9,040,505 B2 * 5/2015 Kelley .................. A61K 33/243
                                                                    514/120
9,315,481 B2 * 4/2016 Kelley .................. C07C 235/78
(Continued)

FOREIGN PATENT DOCUMENTS

CA      2700274 A1   4/2009
JP   2014516051 A    7/2014
(Continued)

OTHER PUBLICATIONS

Mark R. Kelley, James H. Wikel et al. Identification and Characterization of New Chemical Entities Targeting Apurinic/Apyrimidinic Endonuclease 1 for the Prevention of Chemotherapy-Induced Peripheral Neuropathy, Journal of Pharmacology and Experimental Therapeutics Nov. 1, 2016, 359 (2) 300-309 (Year: 2016).*

(Continued)

*Primary Examiner* — Walter E Webb
*Assistant Examiner* — Amanda Michelle Petritsch
(74) *Attorney, Agent, or Firm* — Sandberg Phoenix & von Gontard, PC

(57) ABSTRACT

Combination therapies including a Apurinic/Apyrimidinic Endonuclease/reduction-oxidation (redox) Factor-1 (APE1/Ref-1) inhibitor specific to inhibit the redox function of APE1/Ref-1 are disclosed herein. The Combination therapies can be used for treating various cancers, as well as other angiogenesis-mediated diseases (e.g., retinal diseases, cardiovascular diseases).

7 Claims, 60 Drawing Sheets

Specification includes a Sequence Listing.

Related U.S. Application Data continuation of application No. 16/092,812, filed as application No. PCT/US2018/023346 on Mar. 20, 2018, now abandoned.

(60) Provisional application No. 62/521,082, filed on Jun. 16, 2017, provisional application No. 62/473,528, filed on Mar. 20, 2017.

(51) Int. Cl.

| | | |
|---|---|---|
| *A61K 31/18* | (2006.01) | |
| *A61K 31/192* | (2006.01) | |
| *A61K 31/20* | (2006.01) | |
| *A61K 31/282* | (2006.01) | |
| *A61K 31/337* | (2006.01) | |
| *A61K 31/343* | (2006.01) | |
| *A61K 31/501* | (2006.01) | |
| *A61K 31/519* | (2006.01) | |
| *A61K 31/7068* | (2006.01) | |
| *A61K 31/713* | (2006.01) | |
| *A61K 33/243* | (2019.01) | |
| *A61K 45/06* | (2006.01) | |
| *A61P 35/00* | (2006.01) | |

(52) U.S. Cl.
CPC ............ *A61K 31/192* (2013.01); *A61K 31/20* (2013.01); *A61K 31/282* (2013.01); *A61K 31/337* (2013.01); *A61K 31/343* (2013.01); *A61K 31/501* (2013.01); *A61K 31/519* (2013.01); *A61K 31/7068* (2013.01); *A61K 31/713* (2013.01); *A61K 33/243* (2019.01); *A61K 45/06* (2013.01); *A61P 35/00* (2018.01)

(58) Field of Classification Search
CPC .... A61K 31/20; A61K 31/282; A61K 31/337; A61K 31/343; A61K 31/501; A61K 31/519; A61K 31/7068; A61K 31/713; A61K 33/243; A61K 45/06
See application file for complete search history.

(56) References Cited

U.S. PATENT DOCUMENTS

| | | | | |
|---|---|---|---|---|
| 10,154,973 | B2* | 12/2018 | Kelley | ............... A61P 9/00 |
| 11,331,294 | B2* | 5/2022 | Kelley | ............... A61K 31/13 |
| 11,351,130 | B2* | 6/2022 | Kelley | ............... A61K 31/192 |
| 11,648,226 | B2* | 5/2023 | Kelley | ............... A61K 31/519 |
| | | | | 424/649 |
| 11,723,886 | B2* | 8/2023 | Kelley | ............... A61K 31/20 |
| | | | | 514/621 |
| 2003/0229004 | A1* | 12/2003 | Zarling | ............... A61K 45/06 |
| | | | | 514/19.5 |

FOREIGN PATENT DOCUMENTS

| | | |
|---|---|---|
| WO | 2012162589 A1 | 11/2012 |
| WO | 2014047782 A1 | 4/2014 |

OTHER PUBLICATIONS

Y. Li, X. Liu, T.Zhou, M.R. Kelley, P. Edwards, H. Gao, X.Qiao, Inhibition of APE1/Ref-1 redox activity rescues human retinal pigment epithelial cells from oxidative stress and reduces choroidal neovascularization, Jan. 2014, Redox Biology (Year: 2014).*

Arpin et al., Applying Small Molecule Signal Transducer and Activator of Transcriptson-3 (STAT3) Protein Inhibitors as Pancreatic Cancer Therapeutics; 2016, Molecular Cancer Therapeutics, vol. 15, No. 5, pp. 794-805.

Blum et al., Systemic Inflammation Alters Satellite Glial Cell Function and Structure. A Possible Contribution to Pain; Neuroscience, 2014, vol. 274, pp. 209-217.

Brooks et al., DNA repair in neural cells: basic science and clinical implications; 2002, Mutation Research, vol. 509, pp. 93-108.

Cardoso et al., Metagenomic Analysis of the Microbiota from the Crop of an Invasive Snail Reveals a Rich Reservoir of Novel Genes; PLOS One, 2012, vol. 7, No. 11, e48505.

Chen et al., Peptidase Inhibitors Improve Recovery of Substance P and Calcitonin Gene-Related Peptide Release From Rat Spinal Cord Slices; Peptides, vol. 17, No. 1, pp. 31-37.

Chen et al., Inhibition of Carbonic Anhydrase-IX as a Novel Strategy to Overcome Hypoxia Mediated Drug Resistance in FLT3/ITD Mutated Acute Myeloid Leukemia; Blood, 2017, 1-page.

Fishel et al., Impact of APE1/Ref-1 Redox Inhibition of Pancreatic Tumor Growth; Mol Cancer Ther., 2011, vol. 10, No. 9, pp. 1698-1708.

Kelley et al., Identification and Characterization of New Chemical Entities Targeting Apurinic/Apyrimidinic Endonuclease 1 for the Prevention of Chemotherapy-Induced Peripheral Neuropathy; The Journal of Pharmacology and Experimental Therapeutics; 2016, pp. 300-309.

Kelley et al., Challenges and opportunities identifying therapeutic targets for chemotherapy-induced peripheral neuropathy resulting from oxidative DNA damage; Neural Regen Res., 2017, vol. 12, No. 1, pp. 72-74.

Konig et al., Inhibition of Carbonic Anhydrase IX as a Novel Strategy to Target FLT3/ITD Mutated AML Cells Under Hypoxic Conditions; Poster Presentations; Experimental Hematology, 2017, vol. 53, pp. S54-S136.

Kramer et al., Causal analysis approaches in Ingenuity Pathways Analysis; Bioinformatics, 2014, pp. 1-8.

Lindblom et al., Tesalitazar, a Dual PPAR-α/γ Agonist, Hamster Carcinogenicity, Investigative Animal and Clinical Studies; Toxicologic Pathology, 2012, vol. 40, pp. 18-32.

Logsdon et al., Regulation of HIF1α under Hypoxia by APE1/Ref-1 Impacts CA9 Expression; Dual-Targeting in Patient-Derived 3D Pancreatic Cancer Models; American Association for Cancer Research; 33-pages.

Masood et al., Small Molecule Inhibitors of Bcl-2 Family Proteins for Pancreatic Cancer Therapy; Cancers, 2011, vol. 3, pp. 1527-1549.

Mcelyea e al., Abstract 5183: Efficacy study of APX3330, a Ref-1 redox inhibitor, and Gemcitabine in a mouse pancreatic ductal adenocarcinoma model; Cancer Research, Tumor Biology; 4-pages.

McHugh M.L, Multiple comparison analysis testing in Anova; Lessons in Biostatistics; 2011, Biochemia Medica, vol. 21, No. 3, pp. 203-209.

Ren et al., Sequential treatment with AT-101 enhances cisplatin chemosensitivity in human non-small cell lung cancer cells through inhibition of apurinic/apyrimidinic endonuclease 1-activated IL-6/STAT3 signaling pathway; Drug Design, Development and Therapy, 2014, vol. 8, pp. 2517-2529.

Sempere et al., A novel 3-dimensional culture system uncovers growth stimulatory actions by TGFβ in pancreatic cancer cells; Cancer Biology & Therapy; vol. 12, No. 3; 2011, pp. 198-207.

Shah et al., Exploiting the Ref-1-APE1 node in cancer signaling and other diseases: from bench to clinic; Precision Oncology; 19-pages.

Stevens et al., A comparison of multiple testing adjustment methods with block-correlation positively-dependent tests; PLOS/ONE; 12-pages.

Su et al., Interactions of APE1 with a redox inhibitor: Evidence for an alternate conformation of the enzyme; Biochemistry, 2011, vol. 50, No. 1, pp. 82-92.

Zhang et al., Inhibition of Apurinic/Apyrimidinic Endonuclease I's Redox Activity Revisited; Biochemistry; 2013; vol. 52, pp. 2955-2966.

WPI Database, 2017, Clarivate Analytics, 2-pages.

Lou et al., Aberrant expression of redox protein Ape1 in colon cancer stem cells; Oncology Letters, 2014, vol. 7, pp. 1078-1082.

Opydo-Chanek et al., Combined action of obatoclax and resveratrol on MOLT-4 cells; Department of Experimntal Hematology, Jagiellonian University in Krakow; 1-page.

(56) References Cited

OTHER PUBLICATIONS

Suzuki et al., Drug-induced Apoptosis and p53, BCL-2 and BAX Expression in Breast Cancer Tissues in Vivo and in Fibroblast Cells in Vitro; Jpn J Clin Oncol, 1999, vol. 29, No. 7, pp. 323-331.

Yang et al., Alterations in the expression of the apurinic/apyrimidinic endonuclease-1/redox factor-1 (APE/Ref-1) in human melanoma and identification of the therapeutic potential of resveratrol as an APE/Ref-1 inhibitor; Mol Cancer Ther, 2005, 14-pages.

Zhang et al., Inhibition of Apurinic/apyrimidinic endonuclease I's redox activity revisited; Biochemistry, 2013, vol. 52, No. 17, pp. 2955-2966.

Bray et al., Bcl-2 Modulation to Activate Apoptosis in Prostate Cancer; Mol. Cancer Res, 2009, 11-pages.

Luo et al., Inhibition of the human apurinic/apyrimidinic endonuclease DNA base excision repair enzyme/redox factor (APE1/Ref-1) using small molecule redox and repair inhibitors: Therapeutic implications; Experimental and Molecular Therapeutics 29: Novel Therapeutic Agents II; 3-pages.

Li et al., Inhibition of APE1/Ref-1 redox activity rescues human retinal pigment epithelial cells from oxidative stress and reduces choroidal neovascularization, Jan. 2014, Redox Biology; vol. 2, pp. 485-494.

Gampala et al., Ref-1 redox activity allers cancer cell metabolism in pancreatic cancer: Exploiting the novel finding as a potential target; J. Exp. Clin. Cancer Res., Aug. 2021, vol. 40, No. 1, pp. 251.

Hartman et al., Inhibition of APE1/Ref-1 for Neovascular Eye Diseases: From Biology to Therapy, Int. J. Mol. Sci., Oct. 2021, vol. 22, No. 19, pp. 10279.

Kelley et al., Functional Analysis of Novel Analogues of E3330 That Block the Redox Signaling Activity of the Multifunctional AP Endonuclease/Redox Signaling Enzyme APEZ1/Ref-1, Antioxidants & Redox Signaling, 2011, vol. 14, No. 8, pp. 1387-1401.

Logsdon et al., Blocking HIF signaling via novel inhibitors of CA9 and APE1/Ref-1 dramatically affects pancreatic cancer cell survival; Sci. Rep., 2018, vol. 8, pp. 13759.

Luo et al., Role of the multifunctional DNA repair and redox signaling protein APE1/Ref-1 in cancer and endothelial cells: Small-molecule inhibition of the redox function of APE1. Redox Signal, 2008, vol. 10, pp. 1853-1867.

Nyland et al., Design and synthesis of novel quinone inhibitors targeted to the redox function of apurinic/apyrimidinic endonuclease 1/redox enhancing factor-1 (Ape1/ref-1). J. Med. Chem., 2010, vol. 53, pp. 1200-1210.

Pasha et al., Ref-1/APE1 Inhibition with Novel Small Molecules Blocks Ocular Neovasclariztion, J. Pharmacol., Exp. Ther., 2018, vol. 367, No. 1., pp. 108-118.

Jiang et al., Inhibition of APE1/Ref-1 redox activity with ZPX3330 blocks retinal angiogenesis in vitor and in vivo. Vision Research, 2011, vol. 51, pp. 93-100.

\* cited by examiner

Figures 6B - 6E
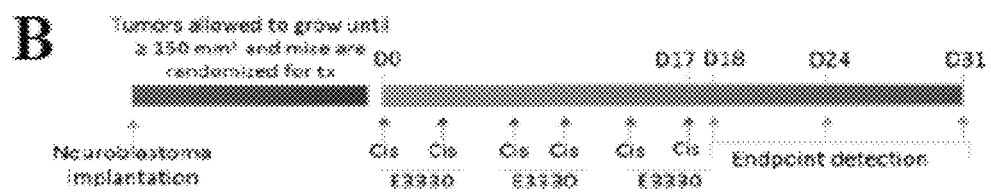
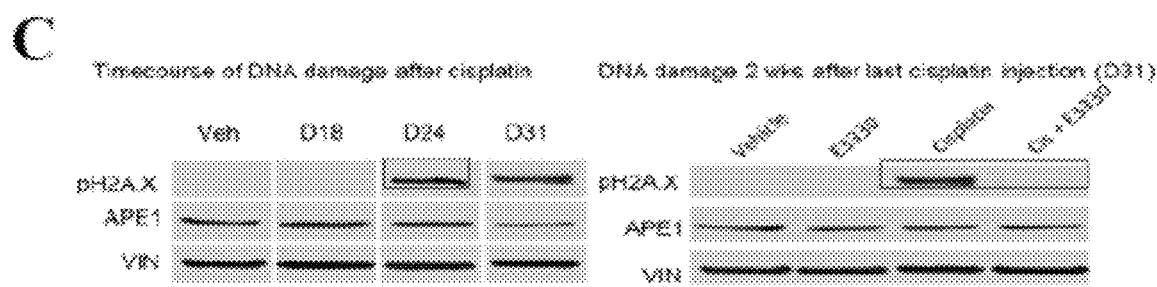
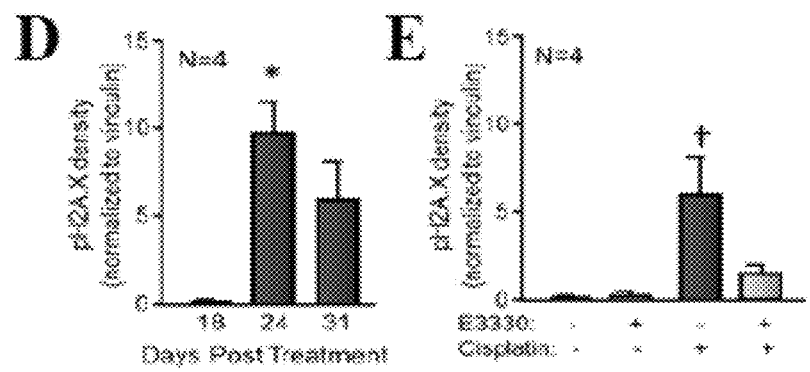

| Gene affected | Pathway/Role | Fold change | Significance (Adj. p-value) |
|---|---|---|---|
| BCRP | ATP-binding cassette transport | 12.9 | 0.011 |
| CIRBP | Cold Shock response | 0.20 | $7.92 \times 10^{-5}$ |
| ITGA1 | Virus Entry via Endocytic Pathways | 0.15 | 0.015 |
| NOTCH3 | Notch Signaling | 0.09 | $4.87 \times 10^{-5}$ |
| PPIF | Mitochondrial Protein folding and permeability | 4.48 | 0.038 |
| PRDX5 | Mitochondrial Dysfunction pathway | 0.28 | $6.86 \times 10^{-3}$ |
| RAB3D | Intracellular transport | 0.11 | $1.29 \times 10^{-5}$ |
| SIPA1 | GTPase Activation | 0.17 | $1.33 \times 10^{-5}$ |
| TAPBP | Peptide Loading complex, antigen presentation pathway | 0.25 | $1.81 \times 10^{-10}$ |

B

| Genes | SCR/siAPE1 Fold change | SCR/siAPE1 Significance (Adj. p-value) | Detectable siAPE1/undetectable siAPE zero Fold change | Detectable siAPE1/undetectable siAPE zero Significance (Adj. p-value) | SCR/detectable siAPE1/undetectable siAPE zero Significance (Adj. p-value) |
|---|---|---|---|---|---|
| COMMD7 | 0.16 | 0.003 | 0.06 | 0.038 | $6.18 \times 10^{-5}$ |
| ISYNA1 | 0.2 | 0.013 | 0.019 | 0.046 | 0.005 |
| TNFAIP2 | 0.09 | 0.004 | 0.01 | 0.034 | $5.15 \times 10^{-5}$ |

C

D

A

B

A                                                                 B

A

B

C

D

A

B

A

B

A

B

A

A

B

C

E3330: 68;
+50 uM CPI-613: 32
+75 uM CPI-613: 11

CPI-613: 85

D

E

Synergistic (50 uM CPI-613) at 50-75 uM E3330

Synergistic (75 uM CPI-613) at 12.5-75 uM E3330

B

C

A

B

A

B

A

B

A

B

A

B

SEQUENCE LISTING

```
Sequence total quantity: 33
SEQ ID NO: 1            moltype = RNA  length = 21
FEATURE                 Location/Qualifiers
source                  1..21
                        mol_type = other RNA
                        organism = synthetic construct
```

```
SEQUENCE: 1
ccatgaggtc agcatggtct g                                                    21

SEQ ID NO: 2              moltype = RNA    length = 21
FEATURE                   Location/Qualifiers
source                    1..21
                          mol_type = other RNA
                          organism = synthetic construct
SEQUENCE: 2
gtctggtacg actggagtac c                                                    21

SEQ ID NO: 3              moltype = RNA    length = 21
FEATURE                   Location/Qualifiers
source                    1..21
                          mol_type = other RNA
                          organism = synthetic construct
SEQUENCE: 3
tactccagtc gtaccagacc t                                                    21

SEQ ID NO: 4              moltype = DNA    length = 22
FEATURE                   Location/Qualifiers
source                    1..22
                          mol_type = other DNA
                          organism = synthetic construct
SEQUENCE: 4
caccattggc aatgagcggt tc                                                   22

SEQ ID NO: 5              moltype = DNA    length = 22
FEATURE                   Location/Qualifiers
source                    1..22
                          mol_type = other DNA
                          organism = synthetic construct
SEQUENCE: 5
aggtctttgc ggatgtccac gt                                                   22

SEQ ID NO: 6              moltype = DNA    length = 22
FEATURE                   Location/Qualifiers
source                    1..22
                          mol_type = other DNA
                          organism = synthetic construct
SEQUENCE: 6
attgcttata gaccggaagc cg                                                   22

SEQ ID NO: 7              moltype = DNA    length = 22
FEATURE                   Location/Qualifiers
source                    1..22
                          mol_type = other DNA
                          organism = synthetic construct
SEQUENCE: 7
aactttttca cccgccatct tg                                                   22

SEQ ID NO: 8              moltype = DNA    length = 22
FEATURE                   Location/Qualifiers
source                    1..22
                          mol_type = other DNA
                          organism = synthetic construct
SEQUENCE: 8
gttctcagca gctcttcggc tt                                                   22

SEQ ID NO: 9              moltype = DNA    length = 22
FEATURE                   Location/Qualifiers
source                    1..22
                          mol_type = other DNA
                          organism = synthetic construct
SEQUENCE: 9
tcctccagac acaccacgga ta                                                   22

SEQ ID NO: 10             moltype = DNA    length = 21
FEATURE                   Location/Qualifiers
source                    1..21
                          mol_type = other DNA
                          organism = synthetic construct
SEQUENCE: 10
gtcagagtgg tggctacagt g                                                    21

SEQ ID NO: 11             moltype = DNA    length = 20
FEATURE                   Location/Qualifiers
source                    1..20
                          mol_type = other DNA
```

```
                        organism = synthetic construct
SEQUENCE: 11
gccctcggag tgtgacttac                                                 20

SEQ ID NO: 12           moltype = DNA   length = 23
FEATURE                 Location/Qualifiers
source                  1..23
                        mol_type = other DNA
                        organism = synthetic construct
SEQUENCE: 12
gagcagcgaa ttggagaaag tgg                                             23

SEQ ID NO: 13           moltype = DNA   length = 22
FEATURE                 Location/Qualifiers
source                  1..22
                        mol_type = other DNA
                        organism = synthetic construct
SEQUENCE: 13
tccatctcgt gcaggaagct gt                                              22

SEQ ID NO: 14           moltype = DNA   length = 22
FEATURE                 Location/Qualifiers
source                  1..22
                        mol_type = other DNA
                        organism = synthetic construct
SEQUENCE: 14
gccagaccaa agtcaagtcc gt                                              22

SEQ ID NO: 15           moltype = DNA   length = 22
FEATURE                 Location/Qualifiers
source                  1..22
                        mol_type = other DNA
                        organism = synthetic construct
SEQUENCE: 15
cttagagcgg aactgcaatg gc                                              22

SEQ ID NO: 16           moltype = DNA   length = 22
FEATURE                 Location/Qualifiers
source                  1..22
                        mol_type = other DNA
                        organism = synthetic construct
SEQUENCE: 16
ccgaagaggt acttgttgca gc                                              22

SEQ ID NO: 17           moltype = DNA   length = 22
FEATURE                 Location/Qualifiers
source                  1..22
                        mol_type = other DNA
                        organism = synthetic construct
SEQUENCE: 17
ggcttccgtg aatgcctcct tt                                              22

SEQ ID NO: 18           moltype = DNA   length = 19
FEATURE                 Location/Qualifiers
source                  1..19
                        mol_type = other DNA
                        organism = synthetic construct
SEQUENCE: 18
ccagatggct tcaccccgc                                                  19

SEQ ID NO: 19           moltype = DNA   length = 20
FEATURE                 Location/Qualifiers
source                  1..20
                        mol_type = other DNA
                        organism = synthetic construct
SEQUENCE: 19
tcagttggca ttggctccag                                                 20

SEQ ID NO: 20           moltype = DNA   length = 22
FEATURE                 Location/Qualifiers
source                  1..22
                        mol_type = other DNA
                        organism = synthetic construct
SEQUENCE: 20
cgacttcacc aaccacaatg gc                                              22

SEQ ID NO: 21           moltype = DNA   length = 22
FEATURE                 Location/Qualifiers
source                  1..22
```

```
                            mol_type = other DNA
                            organism = synthetic construct
SEQUENCE: 21
ggtgttagga ccagcattag cc                                                    22

SEQ ID NO: 22               moltype = DNA  length = 22
FEATURE                     Location/Qualifiers
source                      1..22
                            mol_type = other DNA
                            organism = synthetic construct
SEQUENCE: 22
tgatgccttt gtgactggcg ag                                                    22

SEQ ID NO: 23               moltype = DNA  length = 23
FEATURE                     Location/Qualifiers
source                      1..23
                            mol_type = other DNA
                            organism = synthetic construct
SEQUENCE: 23
ccaaagatgg acaccagcga atc                                                   23

SEQ ID NO: 24               moltype = DNA  length = 22
FEATURE                     Location/Qualifiers
source                      1..22
                            mol_type = other DNA
                            organism = synthetic construct
SEQUENCE: 24
acgtgttgtg cctgctgagg at                                                    22

SEQ ID NO: 25               moltype = DNA  length = 22
FEATURE                     Location/Qualifiers
source                      1..22
                            mol_type = other DNA
                            organism = synthetic construct
SEQUENCE: 25
cttctcgcag atgacatcca cc                                                    22

SEQ ID NO: 26               moltype = DNA  length = 22
FEATURE                     Location/Qualifiers
source                      1..22
                            mol_type = other DNA
                            organism = synthetic construct
SEQUENCE: 26
gtgtccacga tgctgcctta ca                                                    22

SEQ ID NO: 27               moltype = DNA  length = 21
FEATURE                     Location/Qualifiers
source                      1..21
                            mol_type = other DNA
                            organism = synthetic construct
SEQUENCE: 27
cttgctgcca ggctcctgga a                                                     21

SEQ ID NO: 28               moltype = DNA  length = 22
FEATURE                     Location/Qualifiers
source                      1..22
                            mol_type = other DNA
                            organism = synthetic construct
SEQUENCE: 28
gagcctgttc tcatcaccat gg                                                    22

SEQ ID NO: 29               moltype = DNA  length = 22
FEATURE                     Location/Qualifiers
source                      1..22
                            mol_type = other DNA
                            organism = synthetic construct
SEQUENCE: 29
gtaggcaaag ctcaagtcca gc                                                    22

SEQ ID NO: 30               moltype = DNA  length = 22
FEATURE                     Location/Qualifiers
source                      1..22
                            mol_type = other DNA
                            organism = synthetic construct
SEQUENCE: 30
tgctccagaa cctgcatgag ga                                                    22

SEQ ID NO: 31               moltype = DNA  length = 22
FEATURE                     Location/Qualifiers
```

```
source                  1..22
                        mol_type = other DNA
                        organism = synthetic construct
SEQUENCE: 31
aactcaggca gcctcgtgtc ta                                          22

SEQ ID NO: 32           moltype = DNA  length = 20
FEATURE                 Location/Qualifiers
source                  1..20
                        mol_type = other DNA
                        organism = synthetic construct
SEQUENCE: 32
ctcactccac ccccatccta                                             20

SEQ ID NO: 33           moltype = DNA  length = 20
FEATURE                 Location/Qualifiers
source                  1..20
                        mol_type = other DNA
                        organism = synthetic construct
SEQUENCE: 33
ggaccgaggg agacaactag                                             20
```

USE OF APE1/REF-1 INHIBITORS FOR TREATMENT OF RETINAL DISEASES

CROSS-REFERENCE TO RELATED APPLICATIONS

This application is a continuation application of U.S. patent application Ser. No. 17/026,671, filed Sep. 21, 2020, which is a continuation application of U.S. patent application Ser. No. 16/092,812, filed Oct. 11, 2018, which is a U.S. National Phase Application of PCT/US2018/023346 (published as WO2018/175429), filed Mar. 20, 2018, which claims priority to U.S. Provisional Application No. 62/473,528 filed on Mar. 20, 2017, and U.S. Provisional Application No. 62/521,082 filed on Jun. 16, 2017, all of which are hereby incorporated by reference in their entireties.

STATEMENT IN SUPPORT FOR FILING A SEQUENCE LISTING

A computer readable form of the Sequence Listing XML containing the file named "3003527.0528 Sequence Listing.xml," which is 30,061 bytes in size (as measured in MICROSOFT WINDOWS® EXPLORER) and was created on Mar. 23, 2023, is provided herein and is herein incorporated by reference. This Sequence Listing consists of SEQ ID NOs: 1-33.

BACKGROUND OF THE DISCLOSURE

The present disclosure relates generally to the use of an Apurinic/Apyrimidinic Endonuclease/reduction-oxidation (redox) Factor-1 (APE1/Ref-1) inhibitor in a combination therapy to treat various cancers. Particularly, the disclosure relates to the use of APX3330 (formerly known as E3330), a highly selective inhibitor of APE1/Ref-1's redox activity (also referred to herein as "Ref-1"), in a combination therapy to treat cancers such as prostate cancer, colon cancer, ovarian cancer, bladder cancer, non-small cell lung carcinoma, malignant peripheral nerve sheath tumors, leukemia, as well as other angiogenesis-mediated diseases (e.g., retinal diseases, cardiovascular diseases).

Apurinic/Apyrimidinic Endonuclease/reduction-oxidation (Redox) Factor-1 (APE1/Ref-1) was originally identified as an endonuclease that plays a key role in the Base Excision Repair (BER) pathway's repair of oxidative and alkylating damage. Later, APE1/Ref-1 was recognized as a redox signaling protein that modulates the activity of certain transcription factors. Since then, additional functions of APE1/Ref-1 have been uncovered. APE1/Ref-1's duality and pivotal positions in repair and redox activities make it a unique target for therapeutic modulation.

APE1/Ref-1 endonuclease activity is vital to the DNA damage response in all cells, making APE1/Ref-1 a crucial factor in cellular function and survival. The repair function has been conserved from $E.\ coli$ to humans; however, the redox signaling function is observed only in mammals.

APE1/Ref-1 redox signaling affects numerous transcription factors including STAT3, HIF-1α, NF-κB, AP-1, p53, and a few others. APE1/Ref-1 redox signaling is a highly regulated process that reduces oxidized cysteine residues in specific transcription factors as part of their transactivation (FIG. 1). APE1/Ref-1 expression is increased in many tumor types, and that change is associated with increased growth, migration, and drug resistance in tumor cells as well as decreased patient survival.

Because of the pathways it affects, APE1/Ref-1 is seen as a critical node in tumor signaling (FIG. 2), and thus, is a prime target for anticancer therapy However, teasing apart APE1/Ref-1's activities to create a specific inhibitor that targets only its endonuclease or redox function is challenging. Particularly, a number of compounds isolated from natural sources have been proposed as Ref-1 redox signaling inhibitors, but none have been shown to directly or specifically inhibit Ref-1 redox signaling. An example of these natural compounds, resveratrol, is typical of the other compounds; it's in vivo efficacy is sporadic at best due to widely varying bioavailability and low molecular specificity. Another presumed natural Ref-1 redox inhibitor, curcumin, has been established as a promiscuous compound, interacting with a variety of molecules to give false-positive results in numerous biological assays. Thus, these are not specific or viable APE1/Ref-1 redox inhibitors.

Recently, however, the compound APX3330 (formerly called E3330) has been identified as a specific APE1/Ref-1 redox inhibitor. APX3330 has been extensively characterized as a direct, highly selective inhibitor of Ref-1 redox activity that does not affect the protein's endonuclease activity (FIG. 6). Treatment with APX3330 has shown tumor growth and progression, with limited toxicity, in both in vitro and in vivo models.

It would be advantageous to further evaluate targets such as APE1/Ref-1 and rationally design combination therapies, including the correlative biomarker research, such to provide treatment for cancer patients whose therapeutic options remain limited. Moreover, it would be further beneficial to identify synthetic combination therapies of two targets whose co-inhibition leads to dramatic enhancement of cell death compared to their effect when administered alone.

BRIEF DESCRIPTION

The present disclosure relates generally to the use of selective APE1/Ref-1 inhibitors, APX3330, and compounds derived therefrom (e.g., APX2009 and APX2014), in a combination therapy to treat various cancers. The combination therapies are found to treat cancers such as prostate cancer, colon cancer, ovarian cancer, non-small cell lung carcinoma, malignant peripheral nerve sheath tumors, leukemia, as well as other angiogenesis-mediated diseases (e.g., retinal diseases, cardiovascular diseases).

Accordingly, in one aspect, the present disclosure is directed to a combination therapy comprising an Apurinic/Apyrimidinic Endonuclease/reduction-oxidation (redox) Factor-1 (APE1/Ref-1) inhibitor, wherein the APE1/Ref-1 inhibitor inhibits the redox function of APE1/Ref-1 and a second therapeutic agent.

In another aspect, the present disclosure is directed to use of a combination therapy for the treatment of cancer, the combination therapy comprising an Apurinic/Apyrimidinic Endonuclease/reduction-oxidation (redox) Factor-1 (APE1/Ref-1) inhibitor, wherein the APE1/Ref-1 inhibitor inhibits the redox function of APE1/Ref-1 and a second therapeutic agent.

In yet another aspect, the present disclosure is directed to use of a combination therapy for the treatment of retinal disease in a subject in need thereof, the combination therapy comprising an Apurinic/Apyrimidinic Endonuclease/reduction-oxidation (redox) Factor-1 (APE1/Ref-1) inhibitor, wherein the APE1/Ref-1 inhibitor inhibits the endonuclease or redox function of APE1/Ref-1 and a second therapeutic agent.

In yet another aspect, the present disclosure is directed to use of a combination therapy for the treatment of a disease selected from the group consisting of a cardiovascular disease, bacterial infection, gastric inflammatory disorder, and neurodegenerative disease.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3A shows Pa03C low passage patient derived tumor cells grown in 3D cultures in the presence and absence of CAFs. Spheroids were treated with Ruxolitinib alone and in combination with APX3330 (40 uM), and the area of tumor (red channel) and CAF19 #1 (green channel) were quantified following 12 days in culture, n=4, fold change refers to comparison of drug-treated vs media only in the tumor alone spheroids. FIG. 3B depicts the confirmation of inhibition of STAT3 activation via immunoblotting for pSTAT3 Y705 residue after 4 hours of Ruxolitinib treatment (12.5 uM) in the 3D assay 8-10 days post plating. Total STAT3 protein is provided as a loading control and reference for the levels of STAT3 in both cell types. Representative western blot is shown from an n of 3.

FIGS. 6A-6E depict the differential role of APE1 Redox Inhibition in Sensory Neurons vs. Tumor Cells. In tumor cells, Ref-1 redox inhibition has multiple downstream effects on tumor growth, survival, migration and tumor inflammation. In sensory neuron cells such as DRG neurons, the addition of APX3330 does not have a negative effect on the cells and promotes survival and functional protection through enhancement of Ref-1 DNA repair activity against oxidative DNA damaging agents (e.g. cisplatin, oxaliplatin) that invoked the DNA BER pathway (FIG. 6A). In the lower right panel, APX3330 attenuates neurotoxicity induced by systemic administration of cisplatin to tumor-bearing mice. FIG. 6B depicts that the treatment paradigm for investigation of the effects of cisplatin and APX3330 on DNA damage within DRG. Neuroblastoma cells were implanted subcutaneously into the right flanks of 6-wk old male NSG mice and allowed to proliferate until tumor volumes ≥150 mm$^3$. Mice were then randomized for treatment with cisplatin±APX3330 treatment. Cisplatin and APX3330 were administered concurrently for 3 weeks (Day 0-Day 17) and endpoints of neuronal toxicity were assessed within the DRG of mice at several time points following the last dose of cisplatin. FIG. 6C are representative blots demonstrating pH2A.X immunoreactivity at D24 and D31. FIGS. 6D & 6E depict quantification of pH2A.X immunoreactivity. An asterisk indicates statistical significance between D18 and D24 as determined by a one-way ANOVA with Tukey's posttest with $p<0.05$. A cross indicates statistical significance between Veh/Veh group and the Veh/C is group, as determined by a two-way ANOVA with Bonferroni's posttest with $p<0.05$.

FIG. 8A is a representative Western Blot and densitometry analysis of Pa03C cells following APE1 knockdown using 20 nM siRNA. Vinculin is used as a loading control. siAPE1 samples had 10% APE1 levels in comparison to the SCR control sample. FIG. 8B depicts Principal Components Analysis of Uncorrected Gene Expression Data. FIG. 8C depicts Principal Components Analysis of Corrected Gene Expression Data. Following corrections for batch effects using cell cycle-annotated genes, the SCR1 and SCR2 groups come together along the x-axis to form a single SCR group.

FIG. 9A is a Violin Plot illustrating the differences in APE1 RNA expression counts per million (CPM) reads in the SCR, Detectable siAPE1 and Undetectable siAPE1 samples. FIG. 9B depicts Mean Expression and Fold Change Plot using SCR and siAPE1 cells as the two groups in the analysis. FIG. 9C depicts Mean Expression and Fold Change Plot using SCR, detectable siAPE1 and undetectable siAPE1 cells in the analysis. Note that while the analysis uses three separate groups, this plot uses SCR and siAPE1 for calculation of the Mean Expression and Fold Change due to the limitations of the graph.

FIG. 10A is a venn diagram showing the three analyses performed on the scRNA-Seq data and the overlapping genes between them.

Six genes were significantly changed in all three analyses, (FIG. 10B) TMEM45A, (FIG. 10C) TMEM126A, (FIG. 10D) TMEM154, (FIG. 10E) COMMD7, (FIG. 10F) ISYNA1 and (FIG. 10G) TNFAIP2. These genes show increased changes in expression as APE1 levels are reduced further from SCR to detectable (but reduced) siAPE1 to undetectable siAPE1.

Figure 11A:
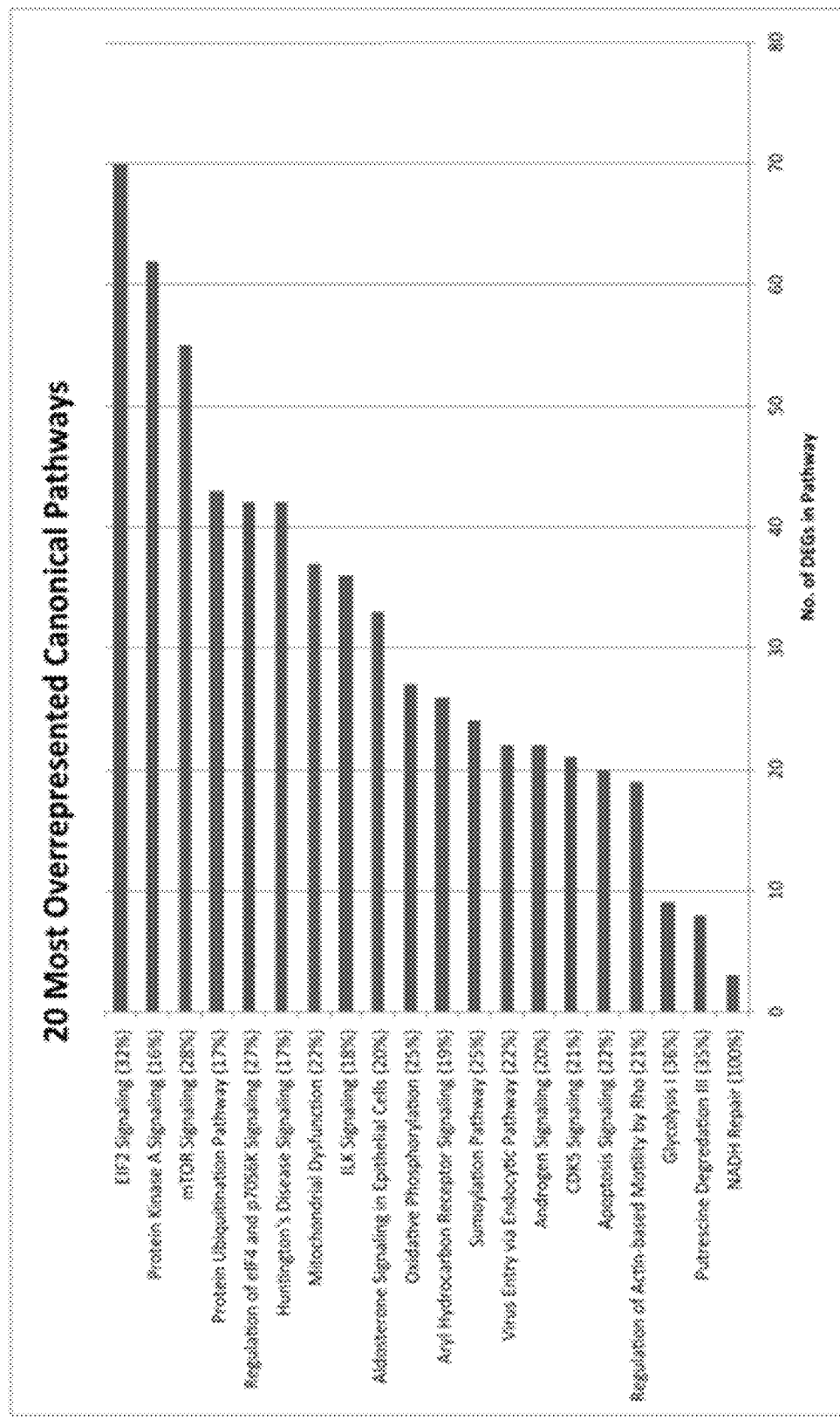
Figure 11B:
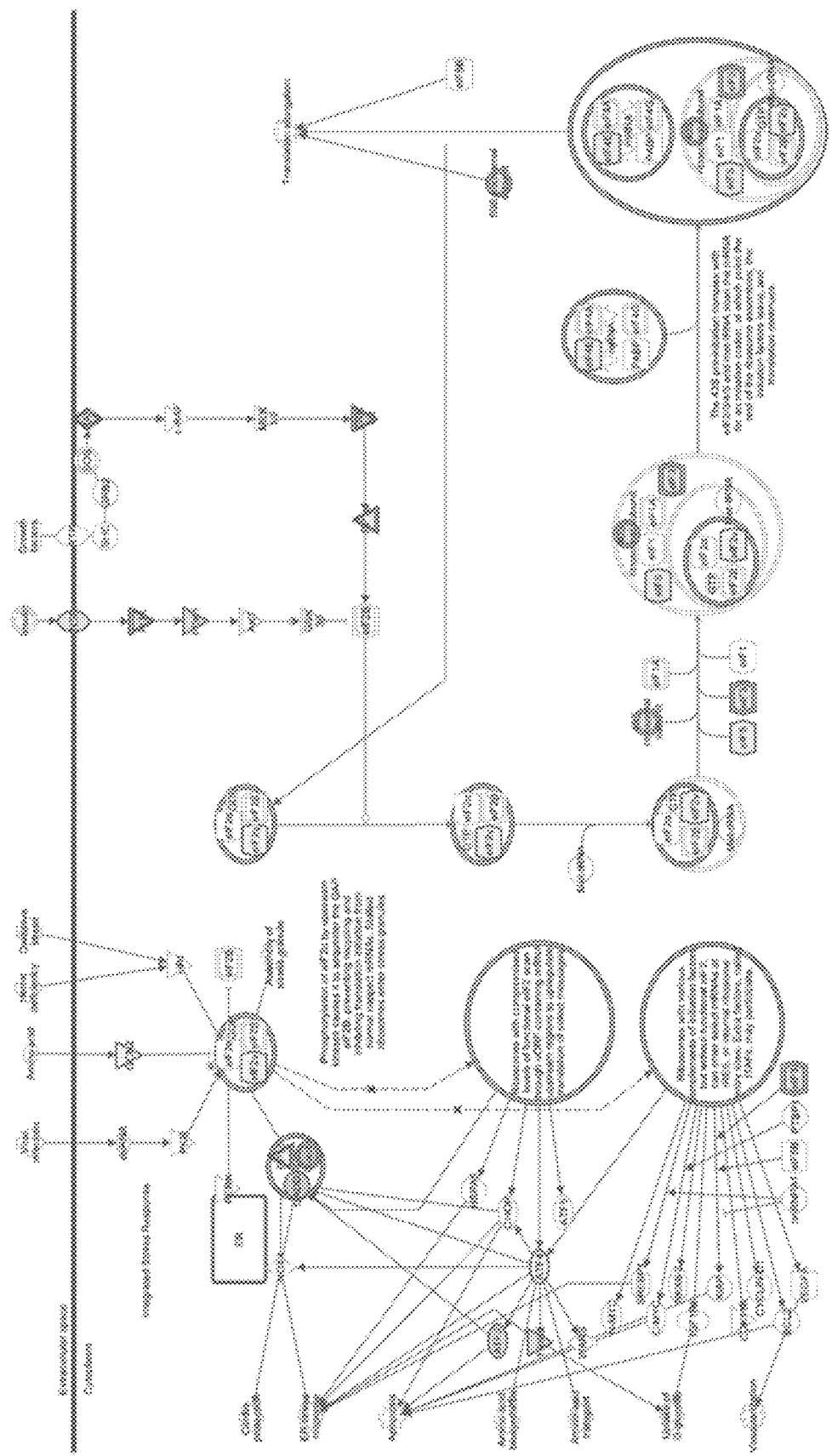
Figure 11C:
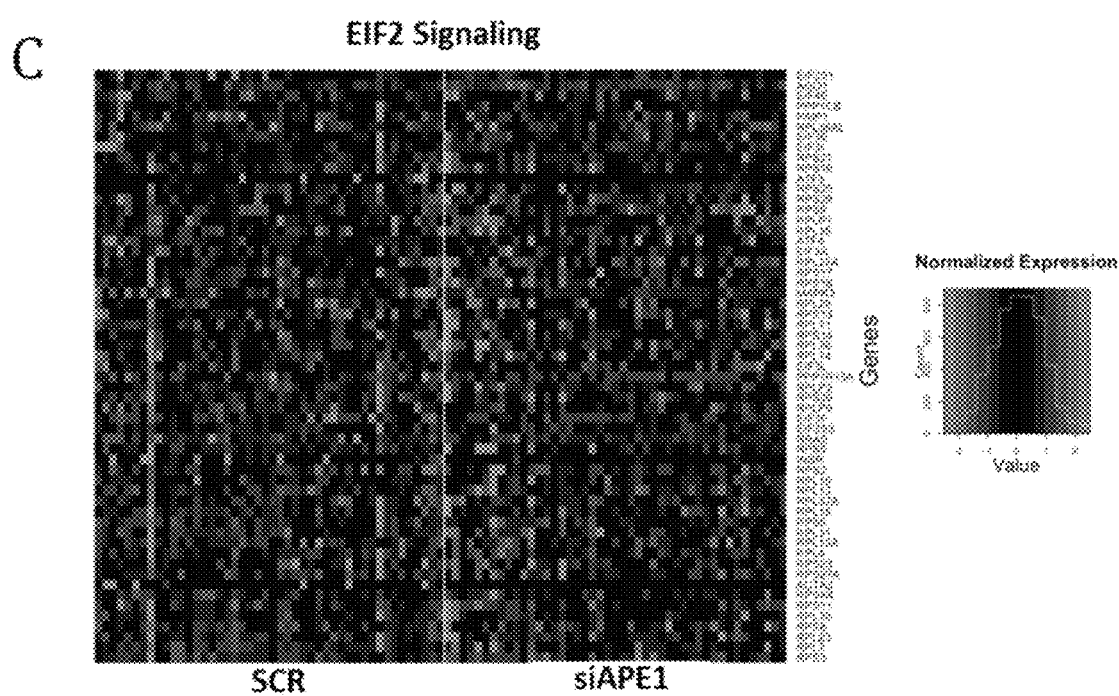

FIGS. 11A-11C depict overlapping overrepresented canonical pathways. FIG. 11A depicts the 20 most significantly overrepresented pathways following IPA analysis on the SCR/detectable siAPE1/undetectable siAPE1 results. The x-axis shows the number of genes that were differentially expressed and in the overrepresented pathways. The percentages next to the pathway labels on the y-axis show the percentage of genes in the pathway which are differentially expressed between SCR and siAPE1 cells. FIG. 11B depicts changes in the EIF2 pathway. The EIF2 pathway was the pathway most affected by APE1 knockdown with 70 DEGs. Genes that are more highly expressed in siAPE1 cells include eIF5 and eIF4E, whereas those that are more highly expressed in control cells include eIF2γ, eIF3, GADD34, G-actin, and 40S ribosomal subunit. Genes or complexes which were identified as differentially expressed are circled and in bold. FIG. 11C is a heatmap showing changes in expression of DEGs per cell involved in the EIF2 pathway. Box showing colors corresponding to normalized changed in expression shown.

Figure 12C:
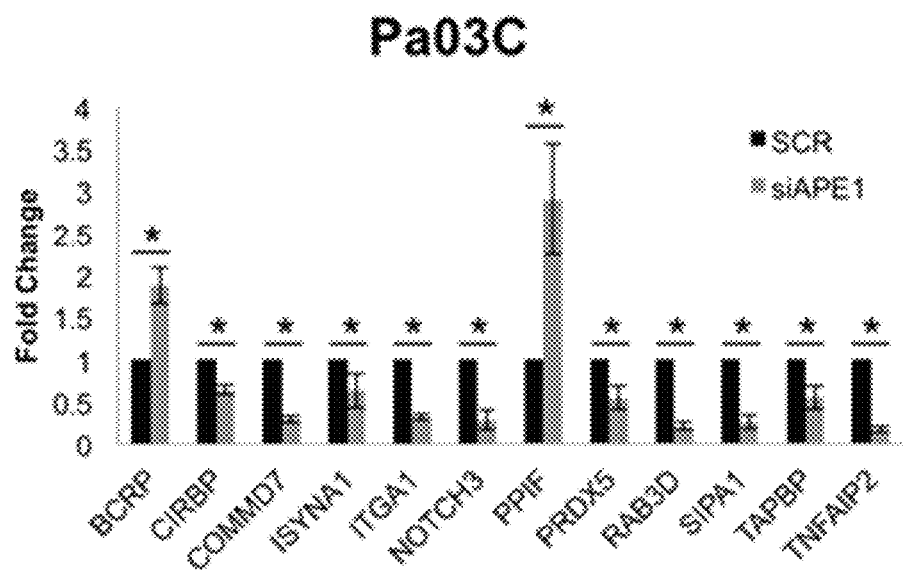
Figure 12D:
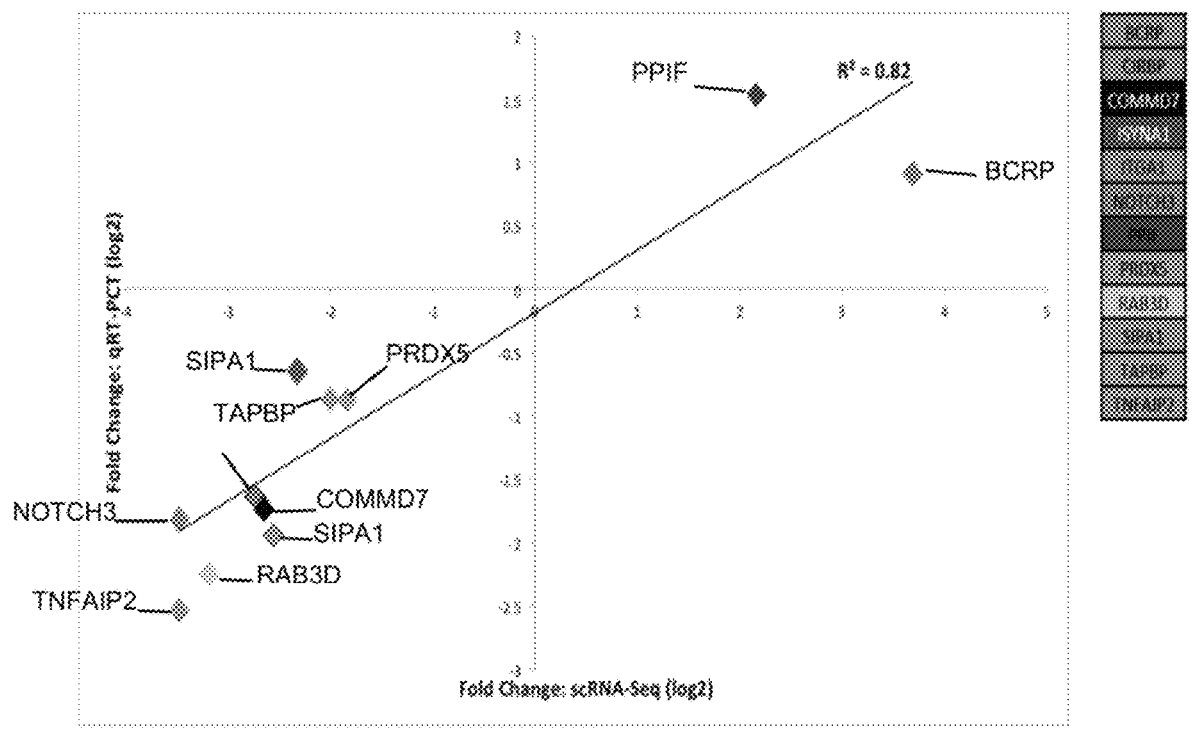

FIGS. 12A-12D depict the validation of scRNA-Seq by qRT-PCR in Pa03C cells. FIG. 12A depicts genes chosen for qRT-PCR validation following SCR/siAPE1 validation. FIG. 12B depicts genes statistically significant in all 3 analyses chosen for qRT-PCR validation. FIG. 12C shows the expression of selected genes assessed via qRT-PCR in Pa03C cells. The cells were collected after siRNA knockdown and assessed for a reduction in APE1 protein levels of 80% or greater. Each graph is the result of 3 independent experiments, showing average fold change in siAPE samples compared to SCR +/−SD. *p<0.05 (ANCOVA model). FIG. 12D depicts the validation analysis. Relation between log 2 fold changes following scRNA-Seq (x-axis) and qRT-PCR (y-axis). $R^2$=0.82. Linear Regression analysis of the slope provided p<0.0001.

Figure 13A:
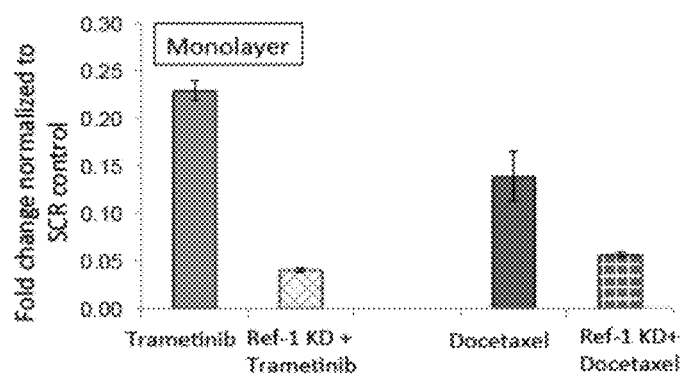
Figure 13B:
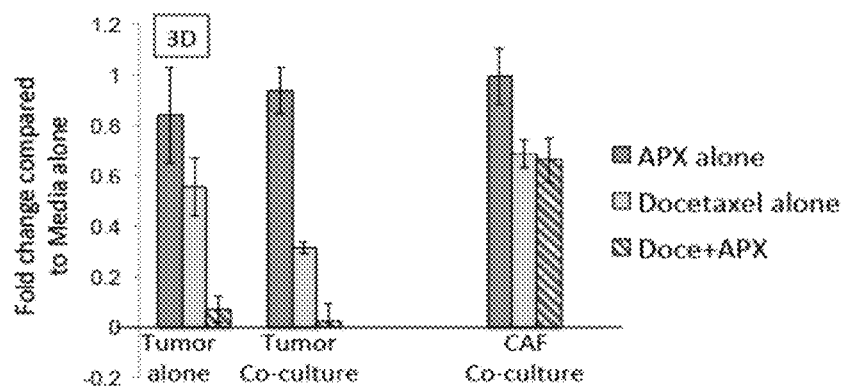

FIGS. 13A & 13B depict the effects of Ref-1 in combination with Docetaxel or Trametinib to PDAC cells and CAFs. In FIG. 13B, a higher dose of Docetaxel was used in co-culture due to the decreased potency in the presence of CAFs.

Figures 14A, 14B, 14C:
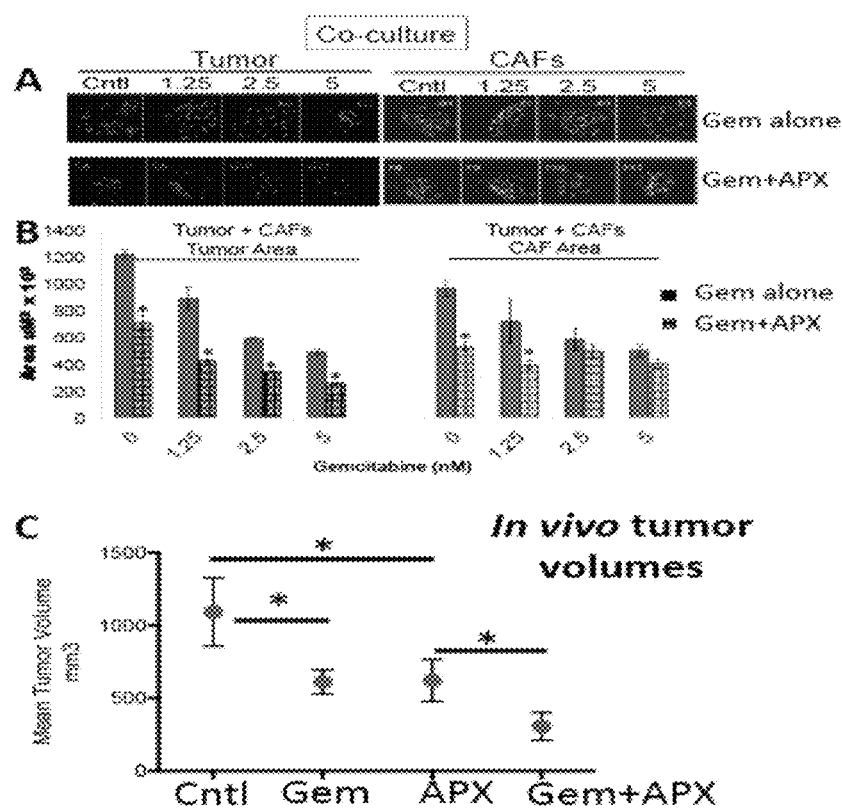

FIGS. 14A-14C depict 3D spheroid and in vivo combination studies with APX3330 and Gemcitabine (Gem). Low passage patient derived PDAC cells (Pa03C, FIG. 14A) in co-culture with cancer-associated fibroblasts (CAF19) treated with increasing amounts of Gem in combination with APX3330 (50 µM). FIG. 14B is a graphical representation: *All Gem+APX330 treatments significantly different from Gem alone in tumor (p<0.01). FIG. 14C depicts tumor volume 30 days following treatment. APX3330 (25 mg/kg) reduces tumor volume in both PaCa-2 and Panc253 patient derived cells in animal models as previously published.

Figures 15A, 15B:
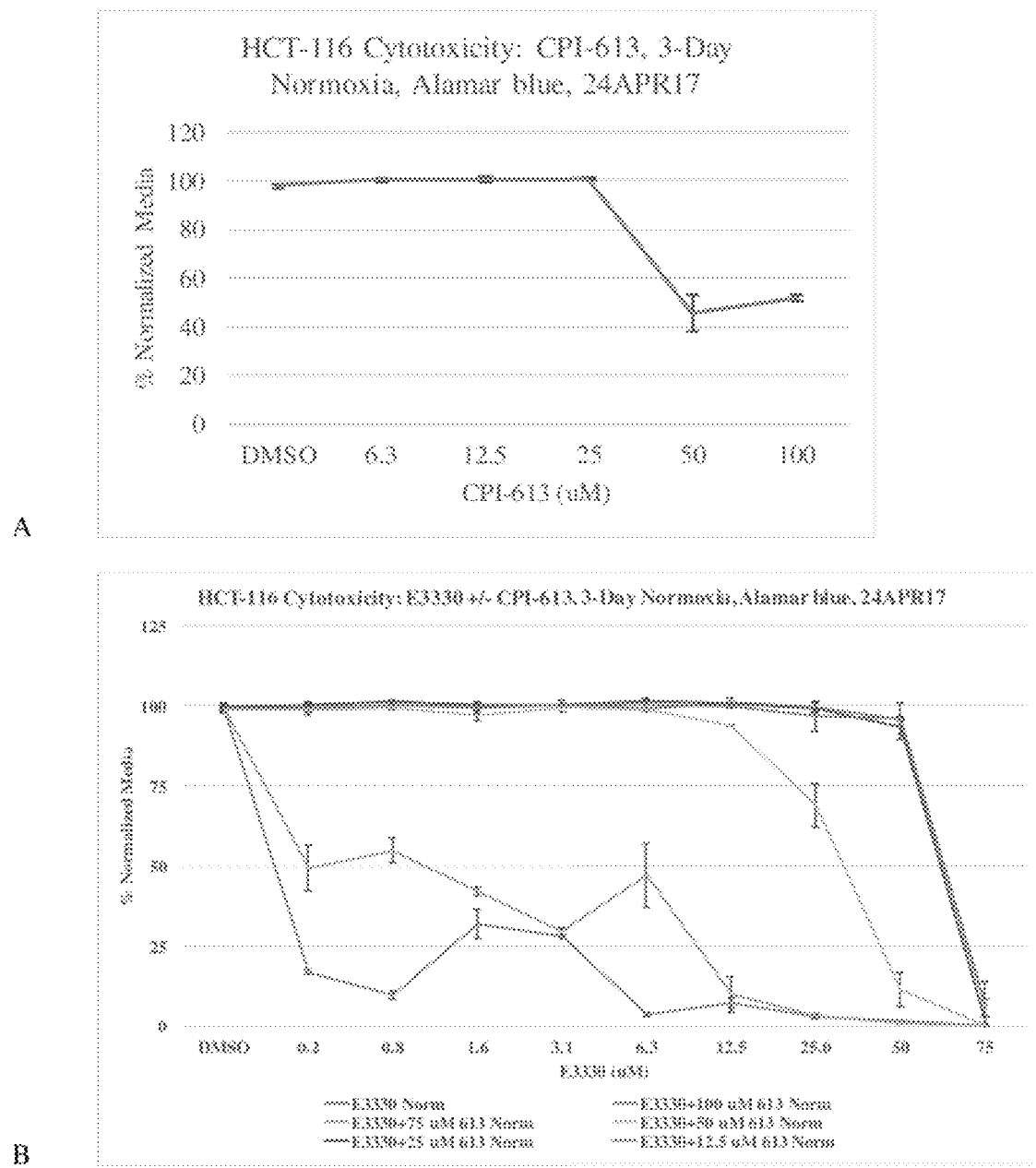
Figure 15C:
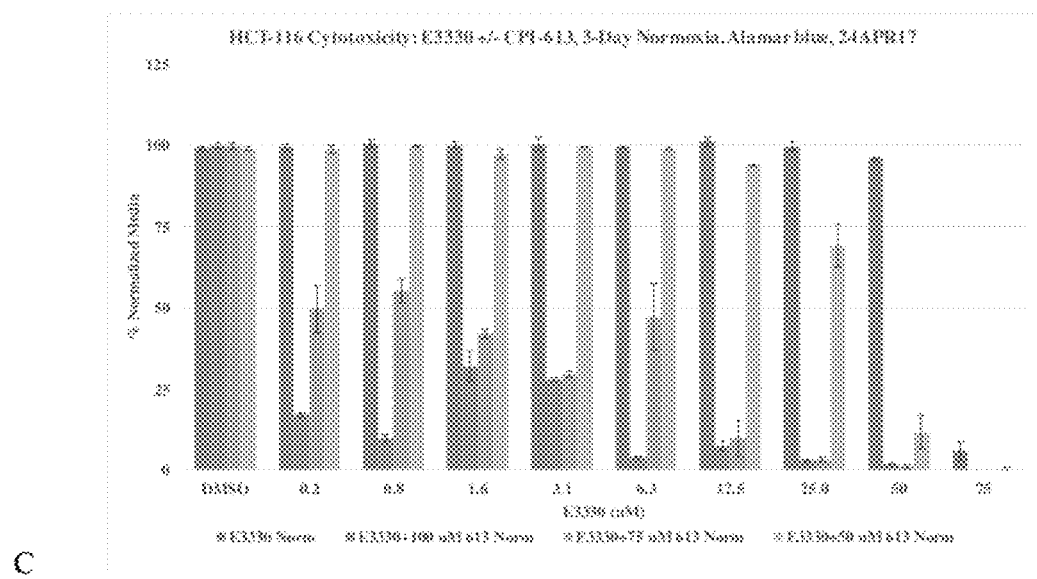

FIGS. 15A-15C depict the effect of APX3330 and CPI-613 on the HCT-116 cell line.

Figures 16A, 16B:
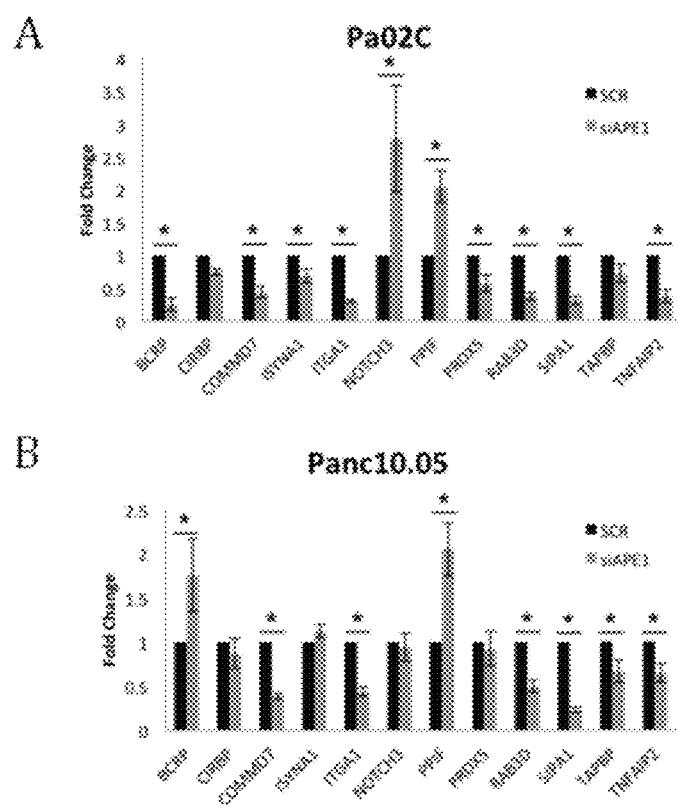
Figures 16C, 16D:
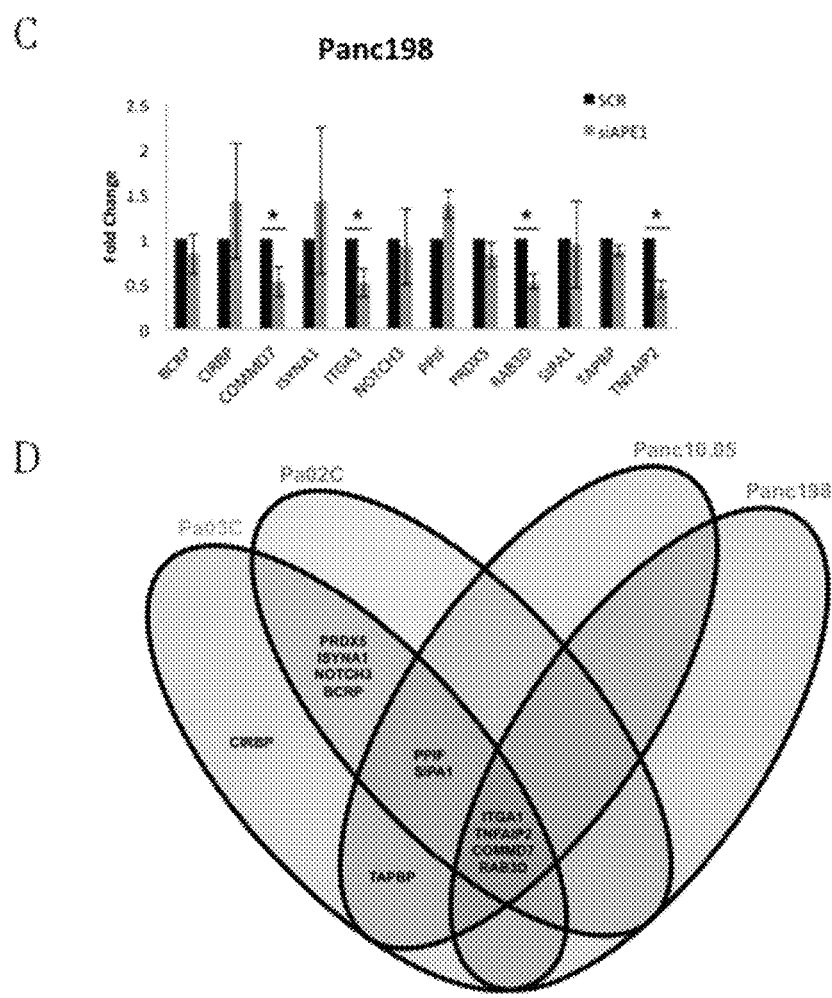

FIGS. 16A-16D depict the different PDAC cell lines exhibiting varied changes to expression of select genes following siRNA knockdown. Expression of selected genes assessed via qRT-PCR in (FIG. 16A) Pa02C cells, (FIG. 16B) Panc10.05 cells and (FIG. 16C) Panc198 cells. The cells were collected after siRNA knockdown and assessed for a reduction in APE1 protein levels of 80% or greater. Each graph is the result of 3 independent experiments, showing average fold change in siAPE samples compared to SCR+/−SD. *p<0.05 (ANCOVA model). FIG. 16D is a venn diagram showing the overlapping results of qRT-PCR between the 4 different PDAC cell lines. COMMD7, ITGA1, RAB3D and TNFAIP2 were significantly changed in all 4 cell lines. PPIF and SIPA1 were differentially expressed in Pa03C, Pa02C and Panc10.05 cells. TAPBP was differentially expressed in Pa03C and Panc10.05. PRDX5, ISYNA1, BCRP and NOTCH3 were common between Pa03C and Pa02C (with BCRP and NOTCH3 changing in opposite directions between the cell lines), while CIRBP was only differentially expressed in Pa03Cs.

Figure 17:
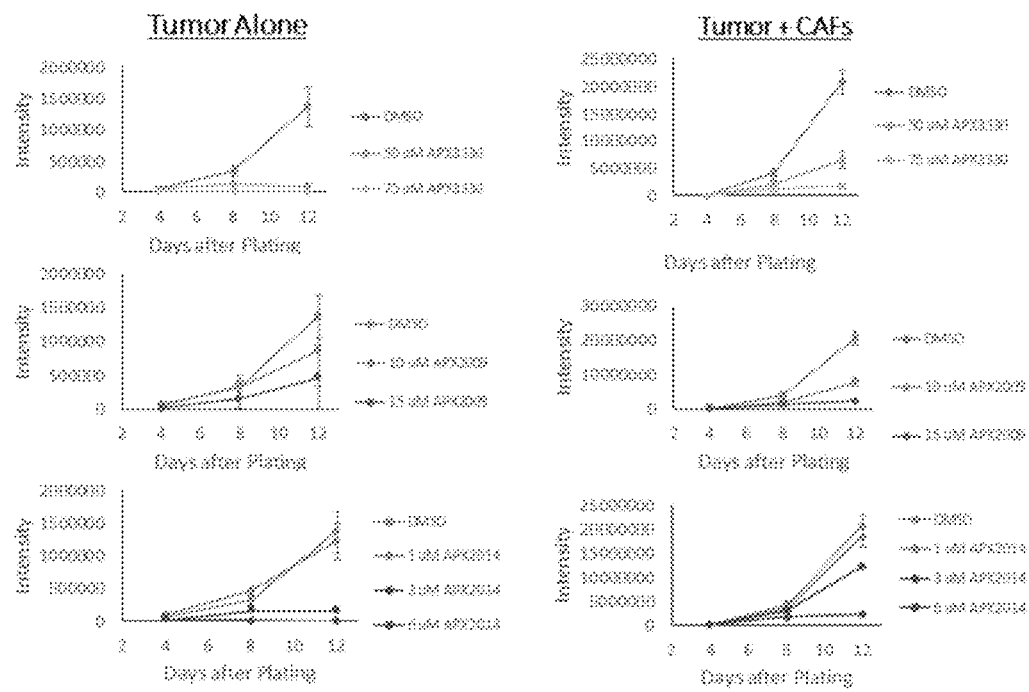

FIG. 17 depicts single agent efficacy of parent compound APX3330, as well as analog compounds APX2009 & APX2014, in 3D spheroid models of pancreatic cancer. Graphs are means with standard deviations of N=3.

Figure 18:
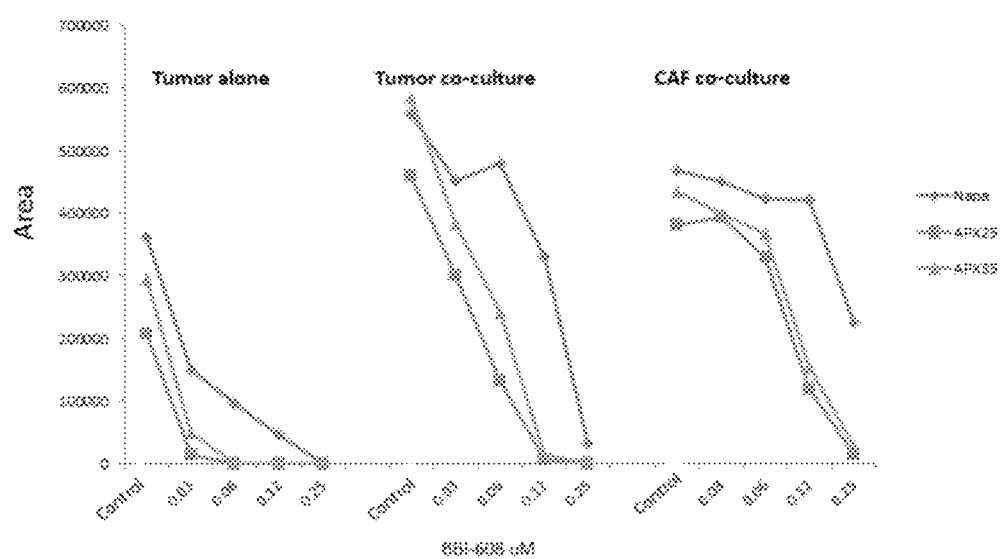

FIG. 18 shows that APX3330 and Napabucasin (BBI-608-STAT3 inhibitor) have synergistic tumor killing in patient-derived 3D spheroid model (Tumor+CAFs) of pancreatic cancer. Concentrations shown are in microMolar; Napa 0.125 uM, APX3330 25 or 35 uM, and APX2009 3.5 uM.

Figure 19:
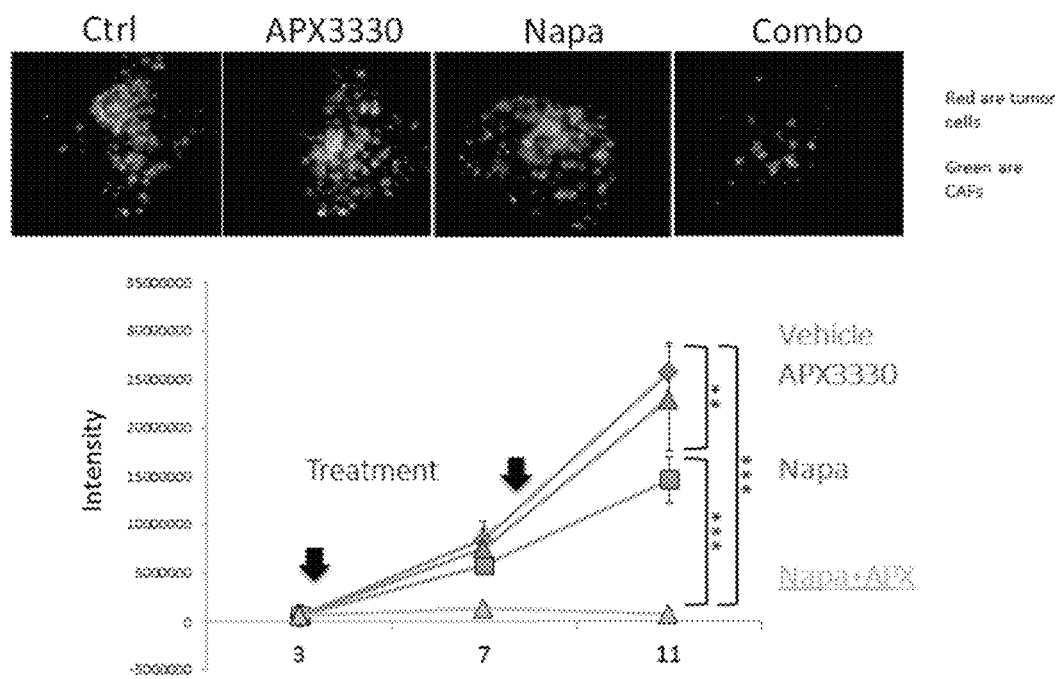

FIGS. 19A & 19B show that APX3330 in combination with STAT3i napabucasin in 3D spheroid model (tumor and CAF) had synergistic killing of pancreatic tumor cells.

Figures 20A, 20B:
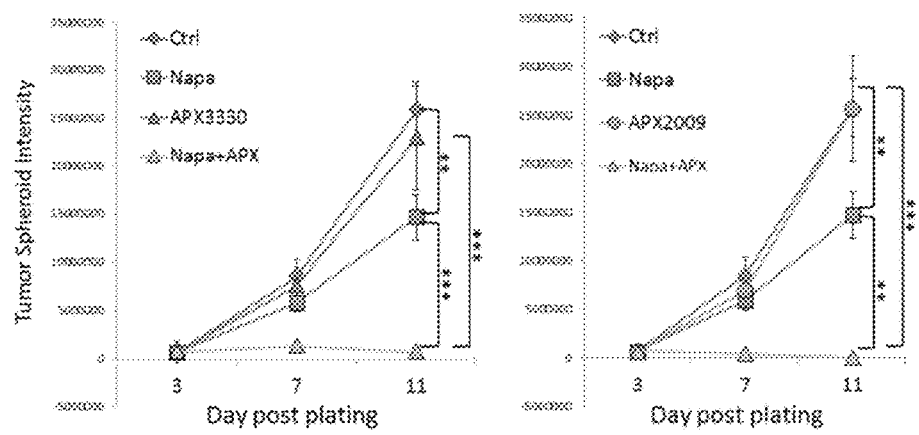

FIGS. 20A & 20B show that APX3330 and APX2009 in combination with STAT3i napabucasin in 3D spheroid model (tumor and CAF) demonstrated synergistic tumor cell killing. Concentrations shown are in microMolar; Napa 0.125 uM, APX3330 25 uM, and APX2009 3.5 uM.  p<0.01, * p<0.001.

Figures 21A, 21B:
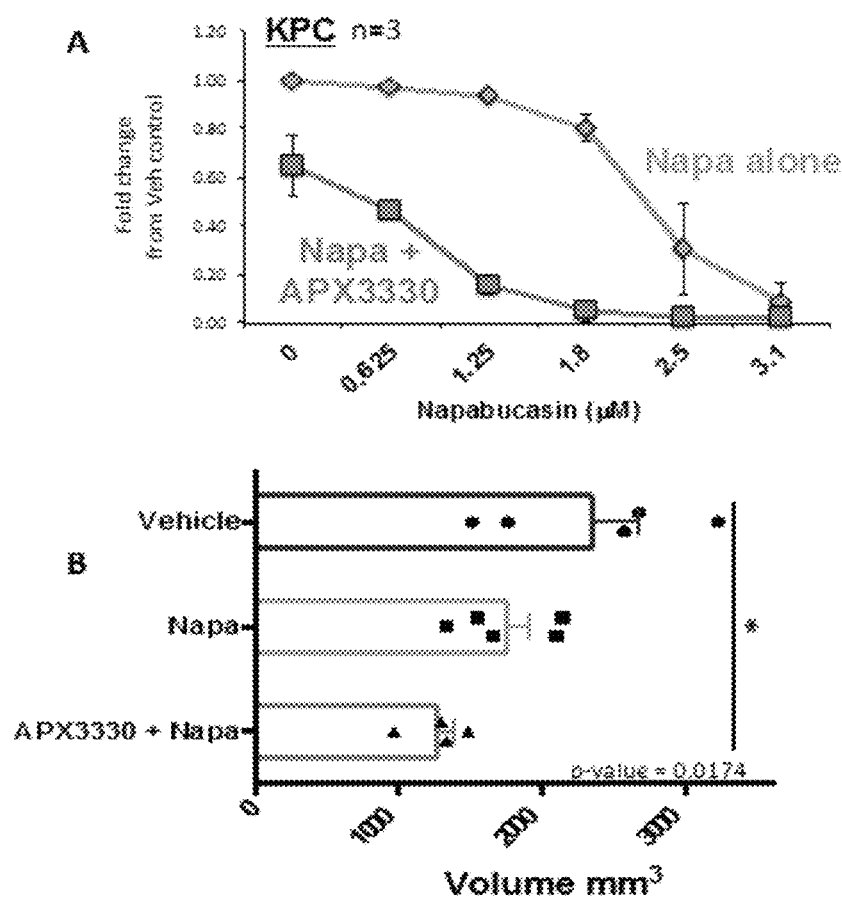

FIGS. 21A & 21B depict dual targeting of Ref-1 and STAT3 results in enhanced killing in genetic PDAC model in vitro (FIG. 21A) and in vivo (FIG. 21B).

Figures 22A, 22B, 22C:
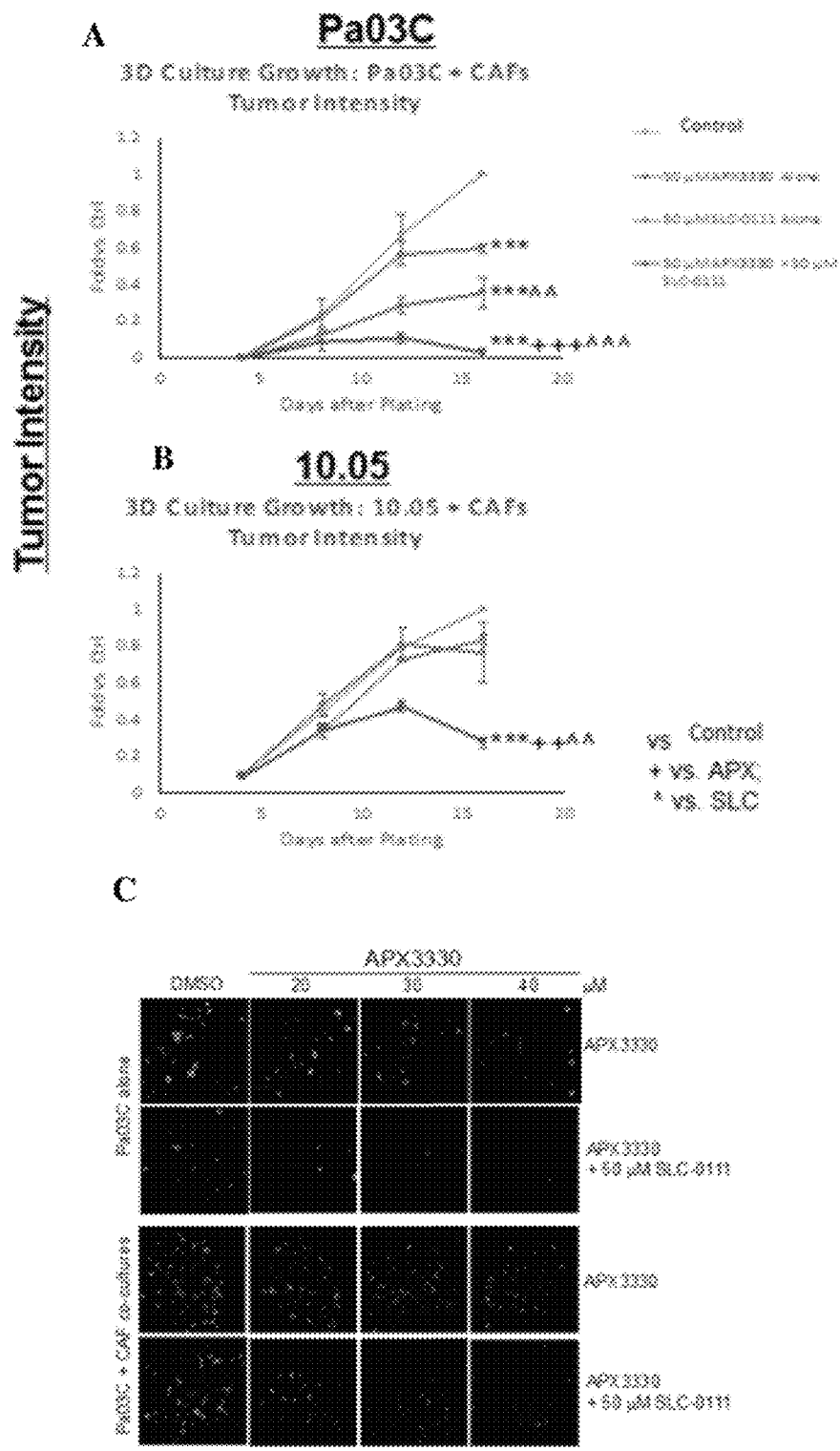

FIGS. 22A-22C show that dual-targeting of CA9 and APE1 kills PDAC tumors in a 3D co-culture pancreatic cancer tumor model.

Figure 23A:
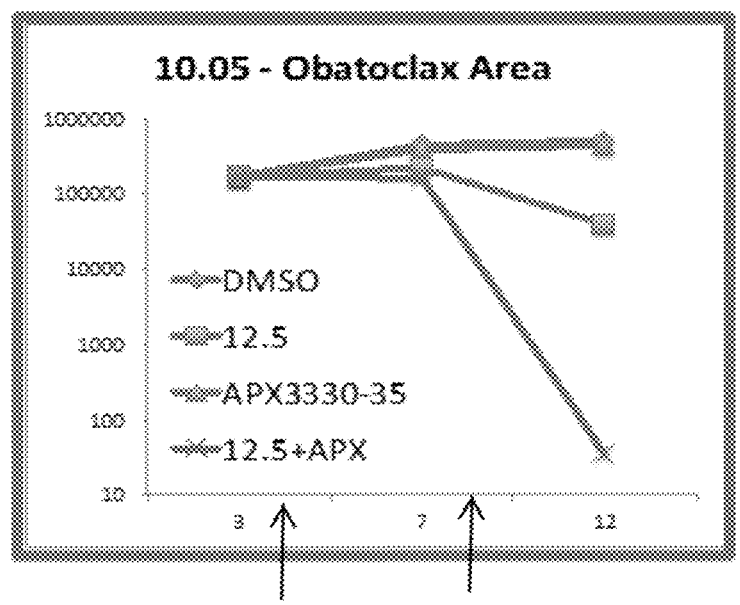
Figure 23B:
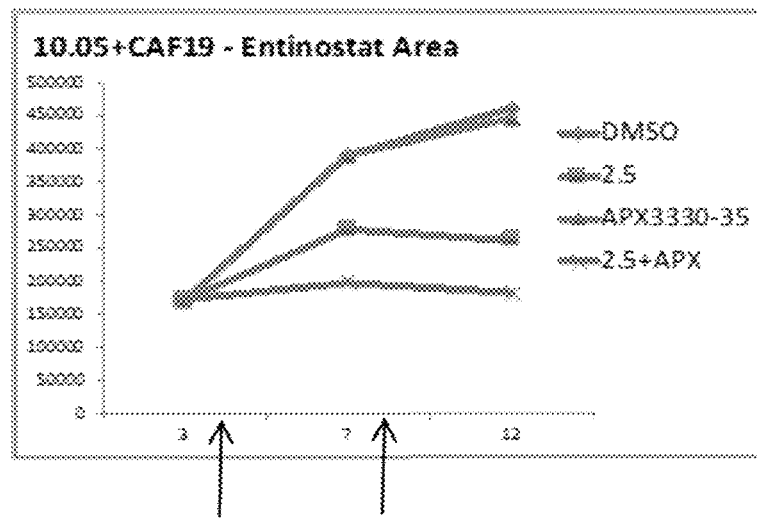
Figure 23C:
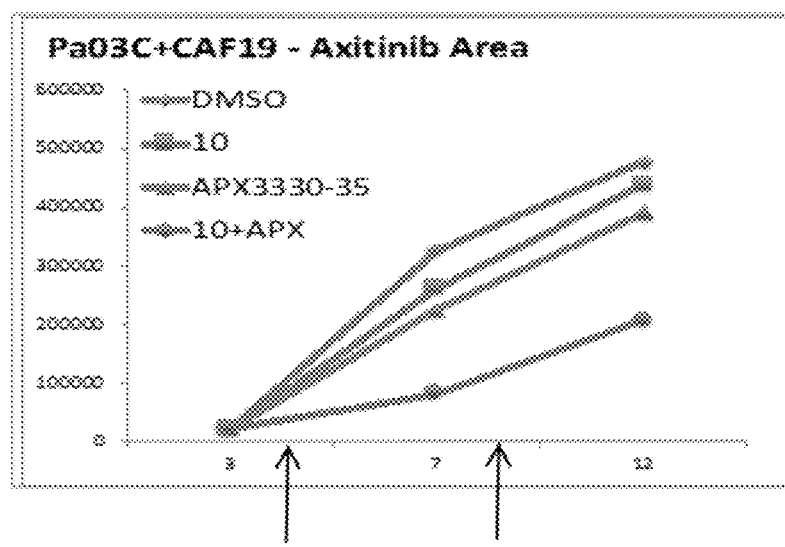
Figure 23D:
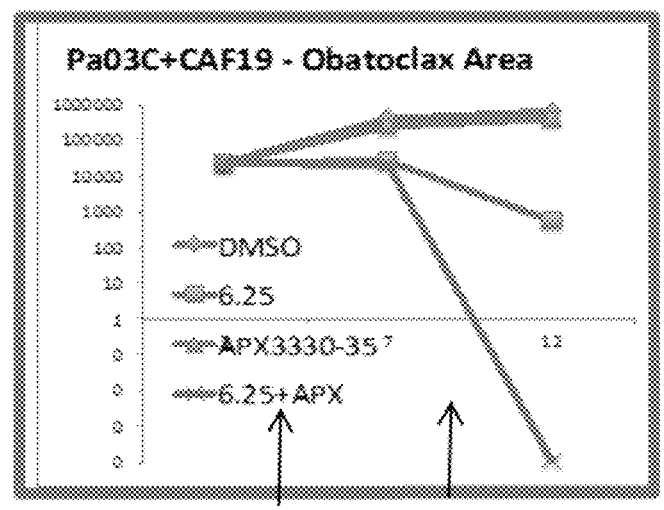
Figure 23E:
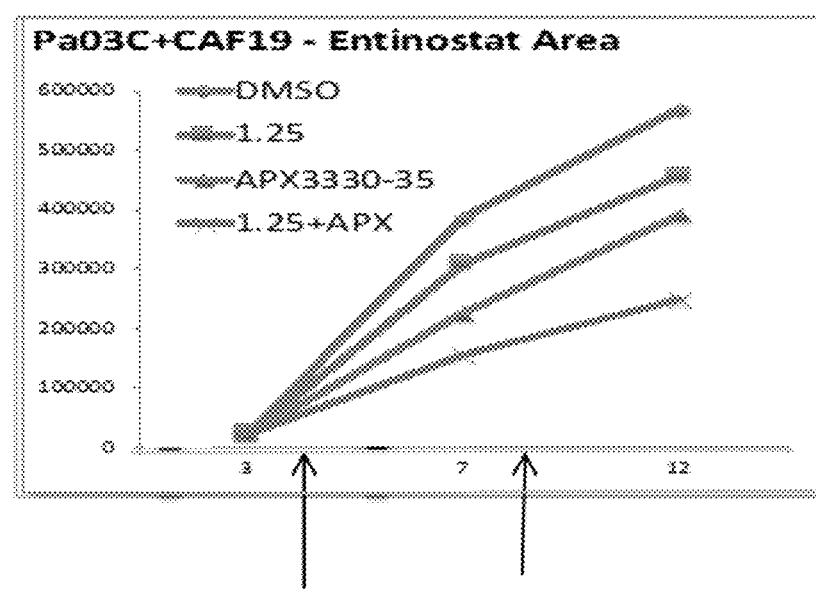

FIGS. 23A-23E depict combination therapy with APE1/Ref-1 inhibitors in a PDAC 3D co-culture model. FIG. 23A depicts the combination therapy of APX3330+Obatoclax (Bcl2 antagonist). FIG. 23B depicts the combination therapy of APX3330+Entinostat (HDAC 1 & 3 inhibitor). FIG. 23C depicts the combination therapy of APX3330+Axitinib (TKI inhibitor). FIG. 23D depicts the combination therapy of APX3330+Obatoclax (Bcl2 antagonist). FIG. 23E depicts the combination therapy of APX3330+Entinostat (HDAC 1 & 3 inhibitor).

Figure 24A:
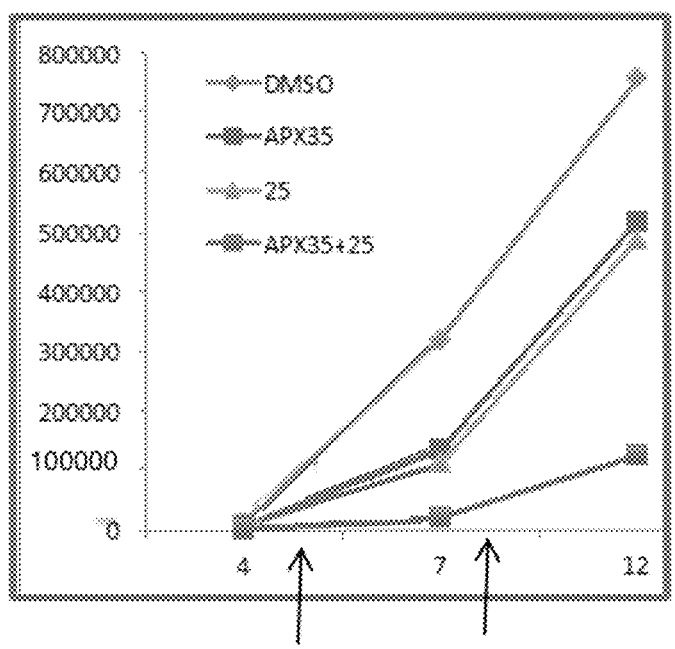
Figure 24B:
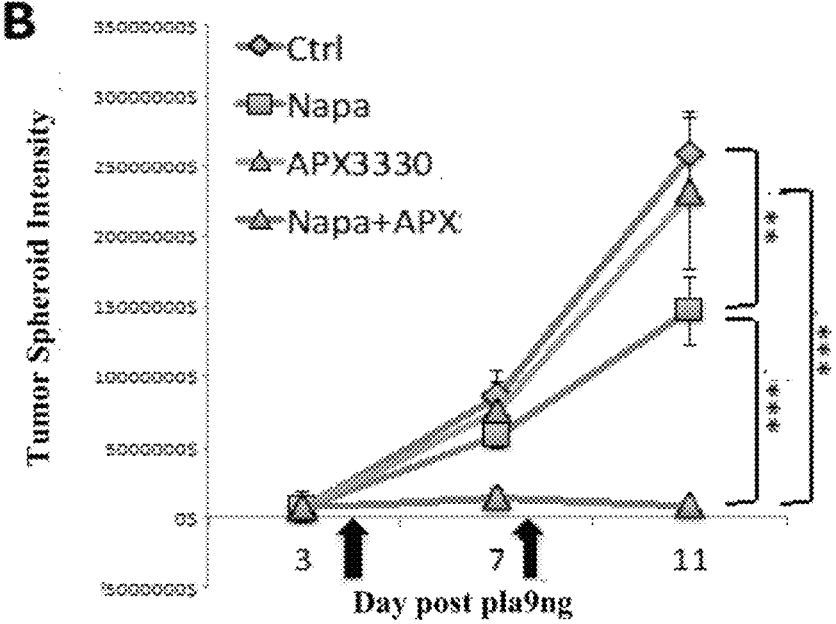
Figure 24C:
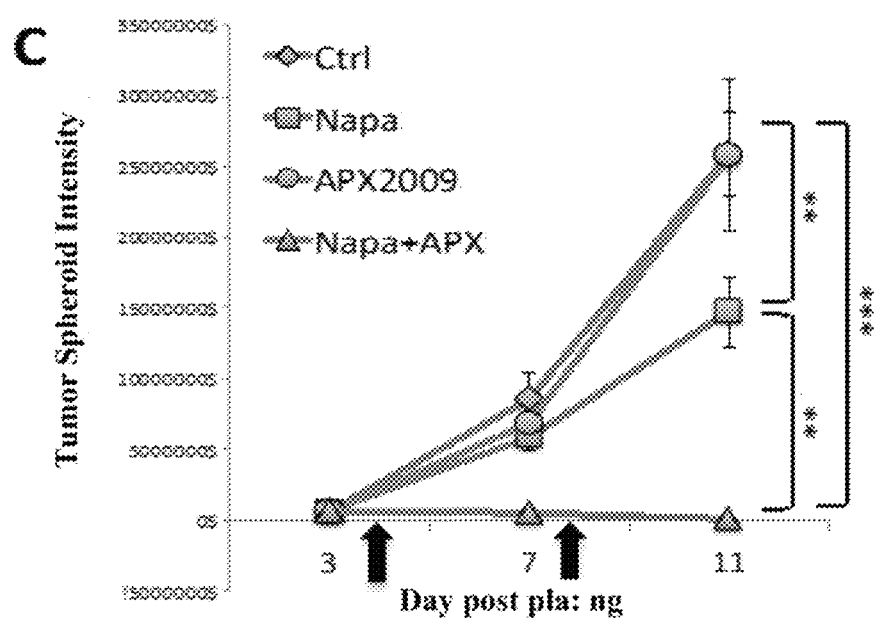

FIGS. 24A-24C depict combination therapy with APE1/Ref-1 inhibitors and CPI-613, a mito targeted TCA cycle inhibitor (FIG. 24A) or STAT3 inhibitor, napabucasin (FIGS. 24B & 24C), in a PDAC 3D co-culture model.

Figure 25:
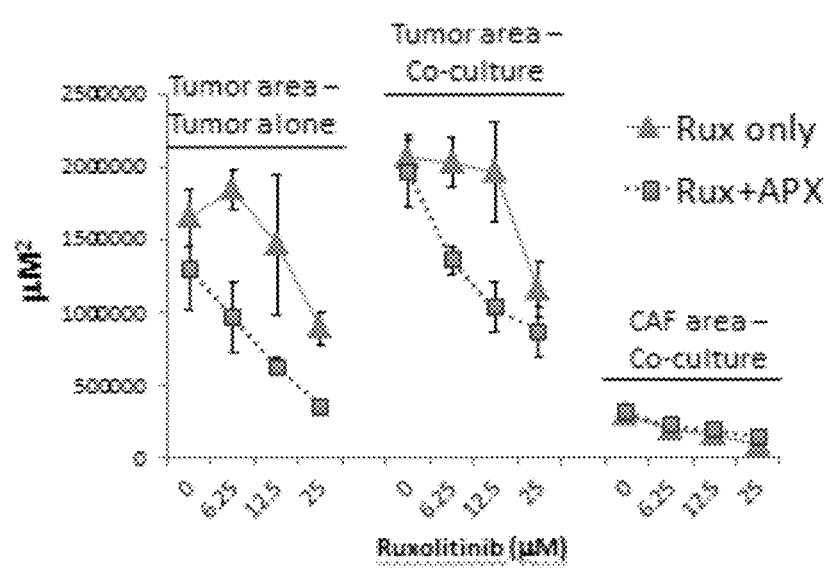

FIG. 25 depicts the effects of ruxolitinib in combination with APX3330 in a 3D model of pancreatic cancer.

Figure 26:
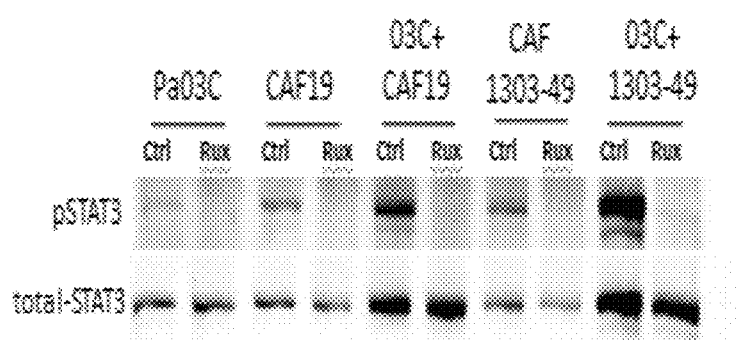

FIG. 26 depicts the effects of ruxolitinib on the phosphorylation of p-STAT3 (Y705) in the 3D co-culture model of pancreatic cancer. Particularly, the Western blot depicts p-STAT3 (Y705) after 4 hours of Ruxolitinib (12.5 mM).

Figure 27:
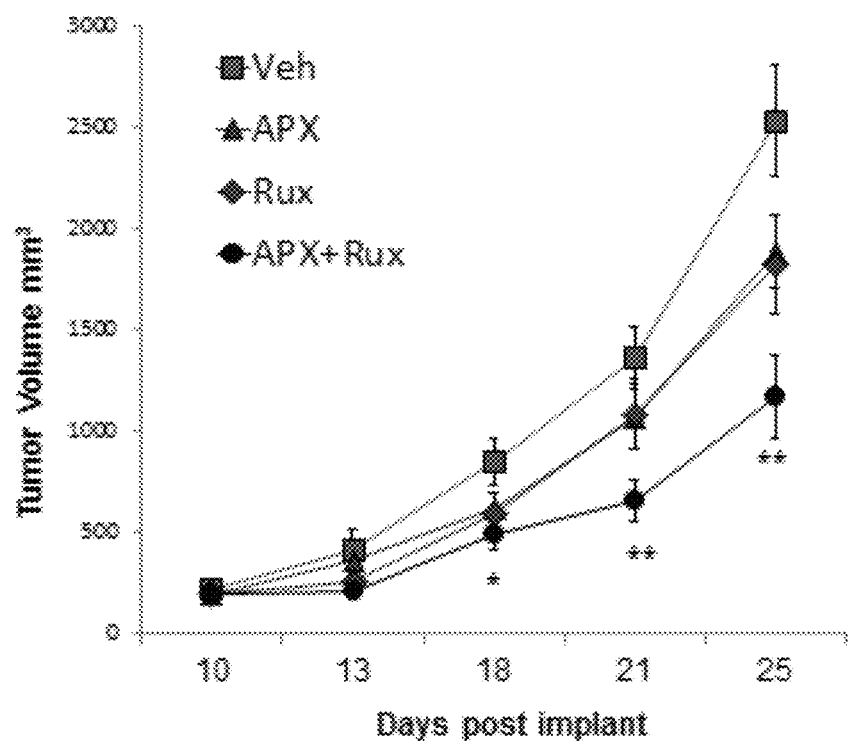

FIG. 27 depicts the effect of the combination treatment of Rux+APX in a flank co-culture model on tumor growth delay.

Figure 28A:
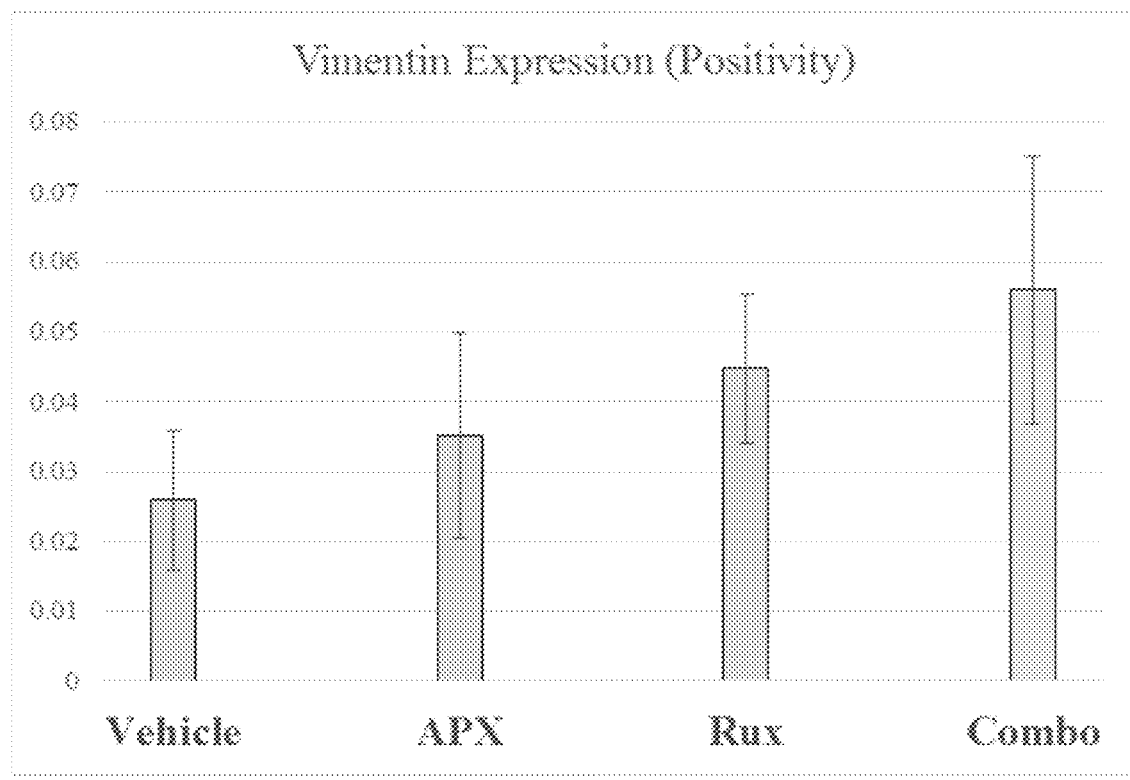
Figure 28B:
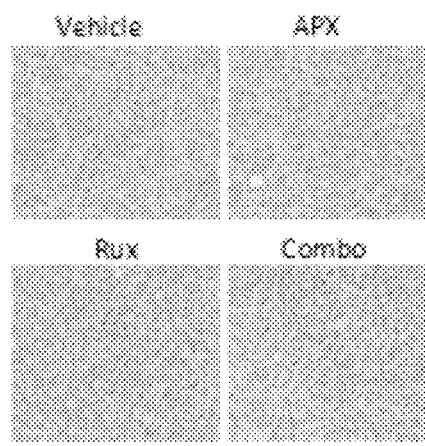

FIGS. 28A & 28B depict that combination treatment did not kill the CAFs in the co-cultured tumors.

FIGS. 29A-29G depict the anti-tumor efficacy of APX3330 in combination with oxaliplatin.

Figure 30A:
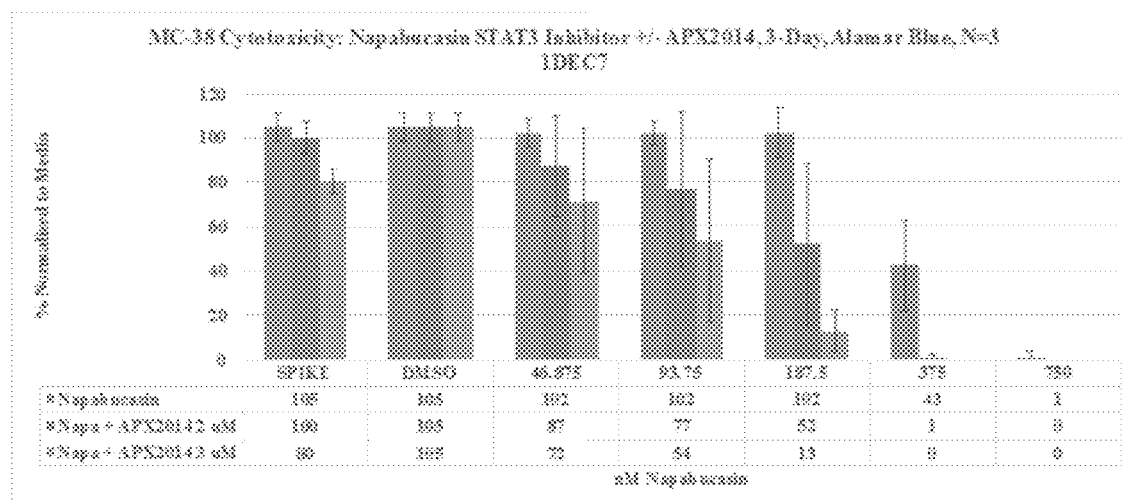
Figure 30B:
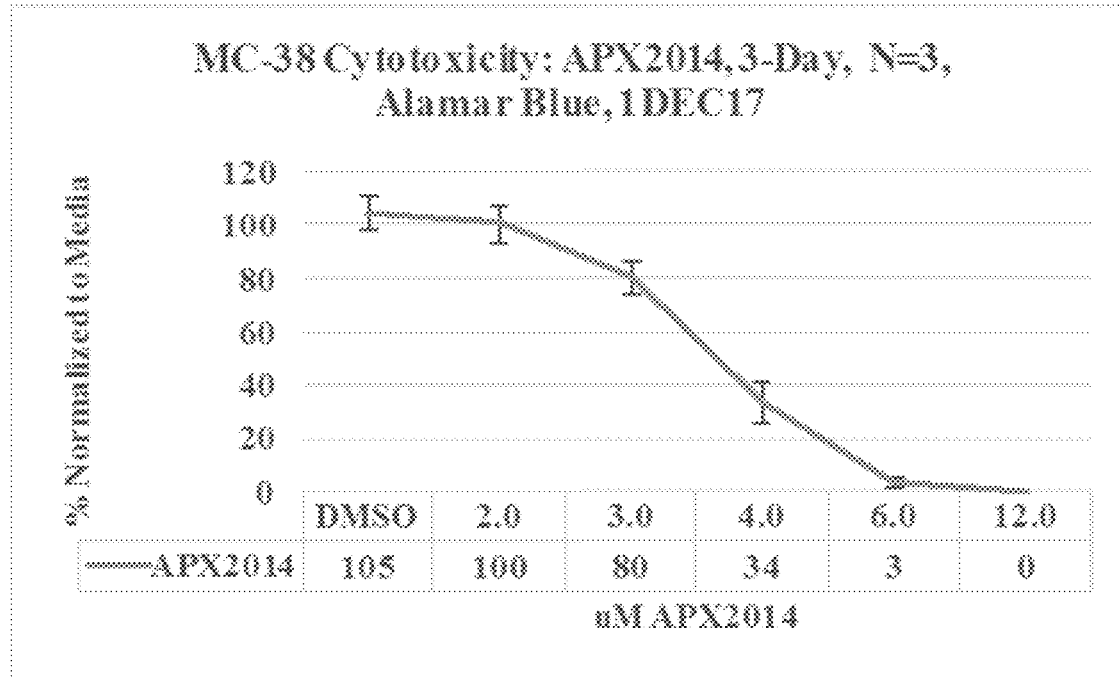

FIGS. 30A & 30B depict STAT3 inhibitor Napabucasin and Ape1 redox inhibitor APX2014 drug combination effects in mouse colon cell line MC-38.

Figure 31A:
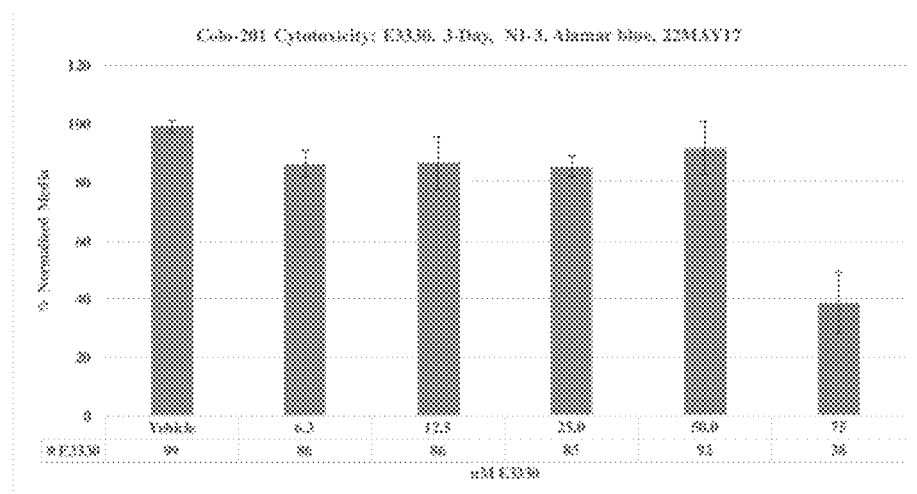
Figure 31A:
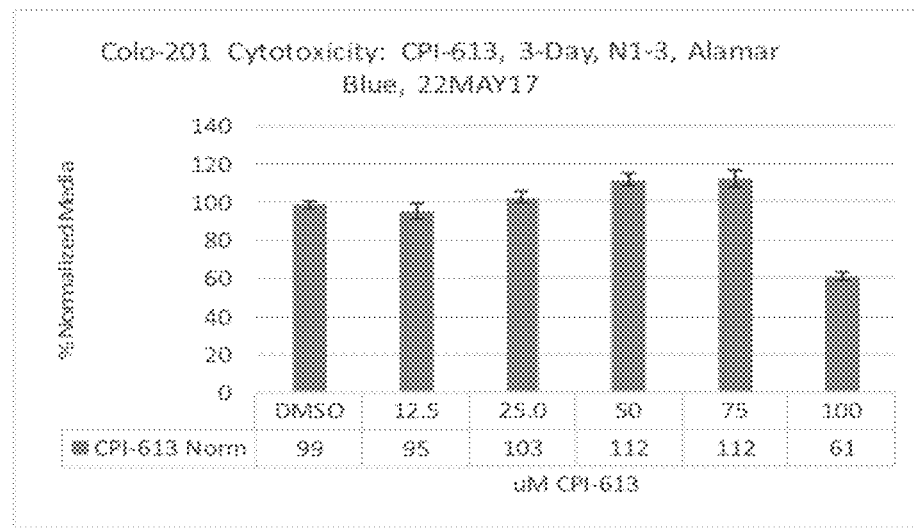
Figures 31B, 31C, 31D, 31E:
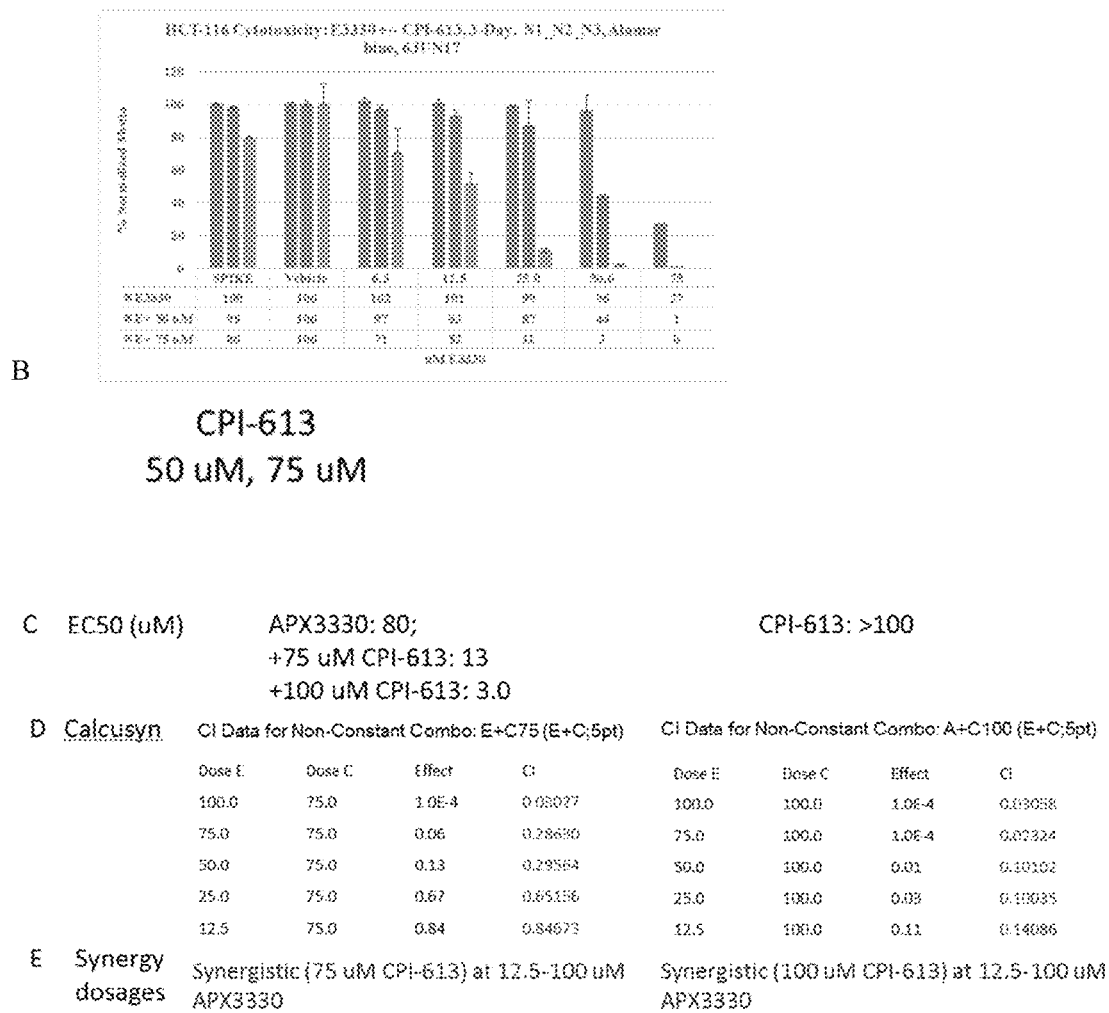

FIGS. 31A-31E depict PDH and alpha-KDH Metabolic inhibitor CPI-613 and Ape1 redox inhibitor APX3330 synergistic drug combination effects in human adenocarcinoma colon suspension cell line Colo-201. FIG. 31A depicts single agent effects. FIG. 31B depicts combination therapy effects. FIG. 31C depicts combination EC50 (μM). FIG. 31D depicts Chou-Talalay Index of dose combinations. FIG. 31E depicts synergy doses.

Figure 32A:
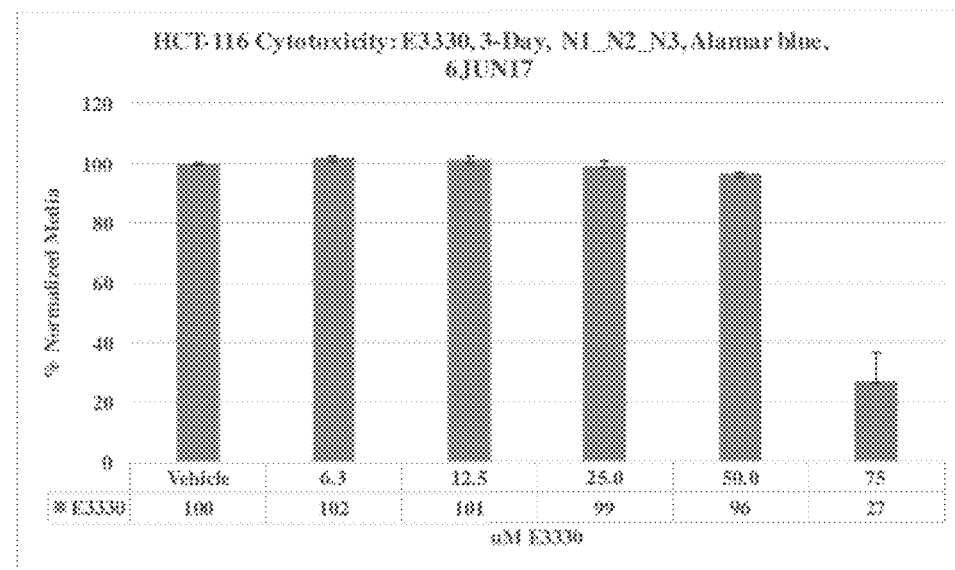
Figure 32A:
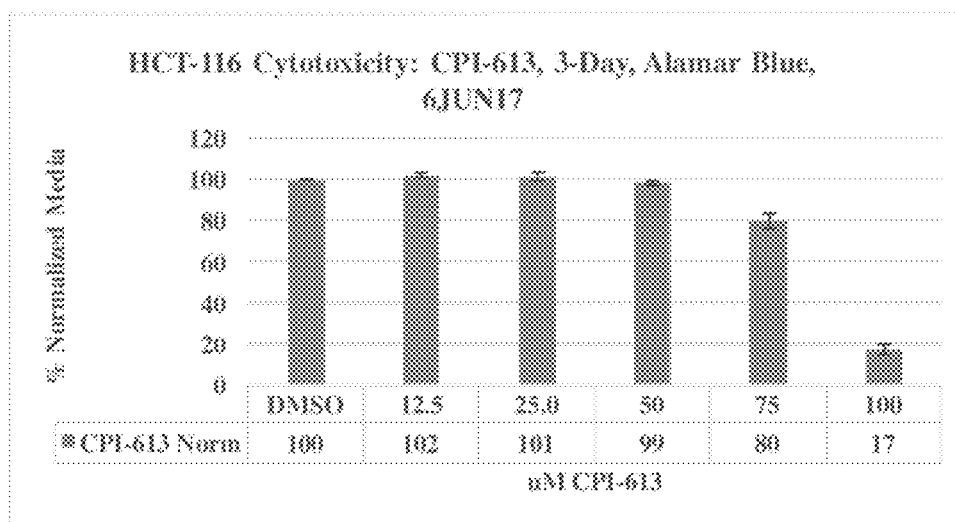
Figures 32B, 32C, 32D, 32E:
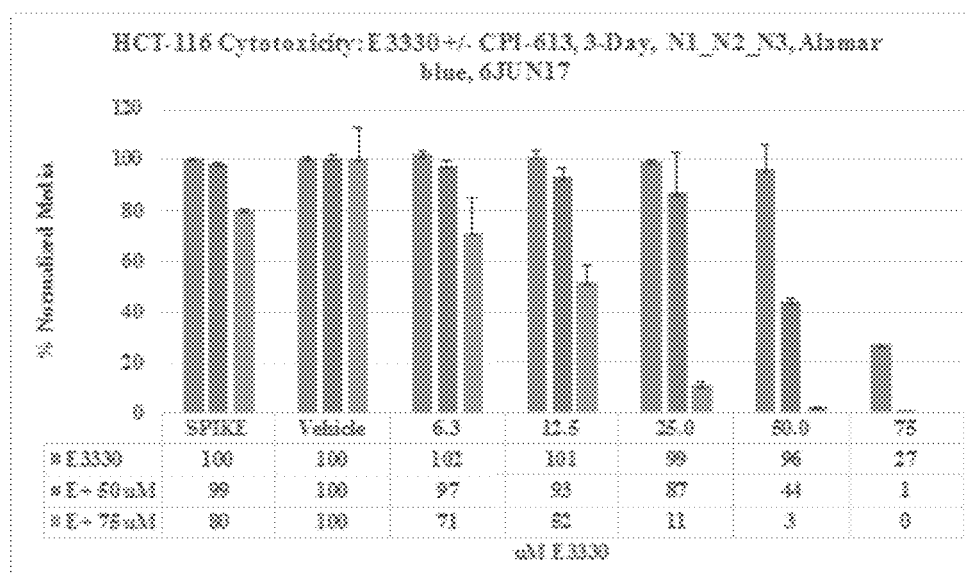

FIGS. 32A-32E depict PDH and alpha-KDH Metabolic inhibitor CPI-613 and Ape1 redox inhibitor APX3330 (also referred to herein as E3330) synergistic drug combination effects in human carcinoma colon cell line HCT-116. FIG. 32A depicts single agent effects. FIG. 32B depicts combination therapy effects. FIG. 32C depicts combination EC50 (μM). FIG. 32D depicts Chou-Talalay Index of dose combinations. FIG. 32E depicts synergy doses.

Figure 33A:
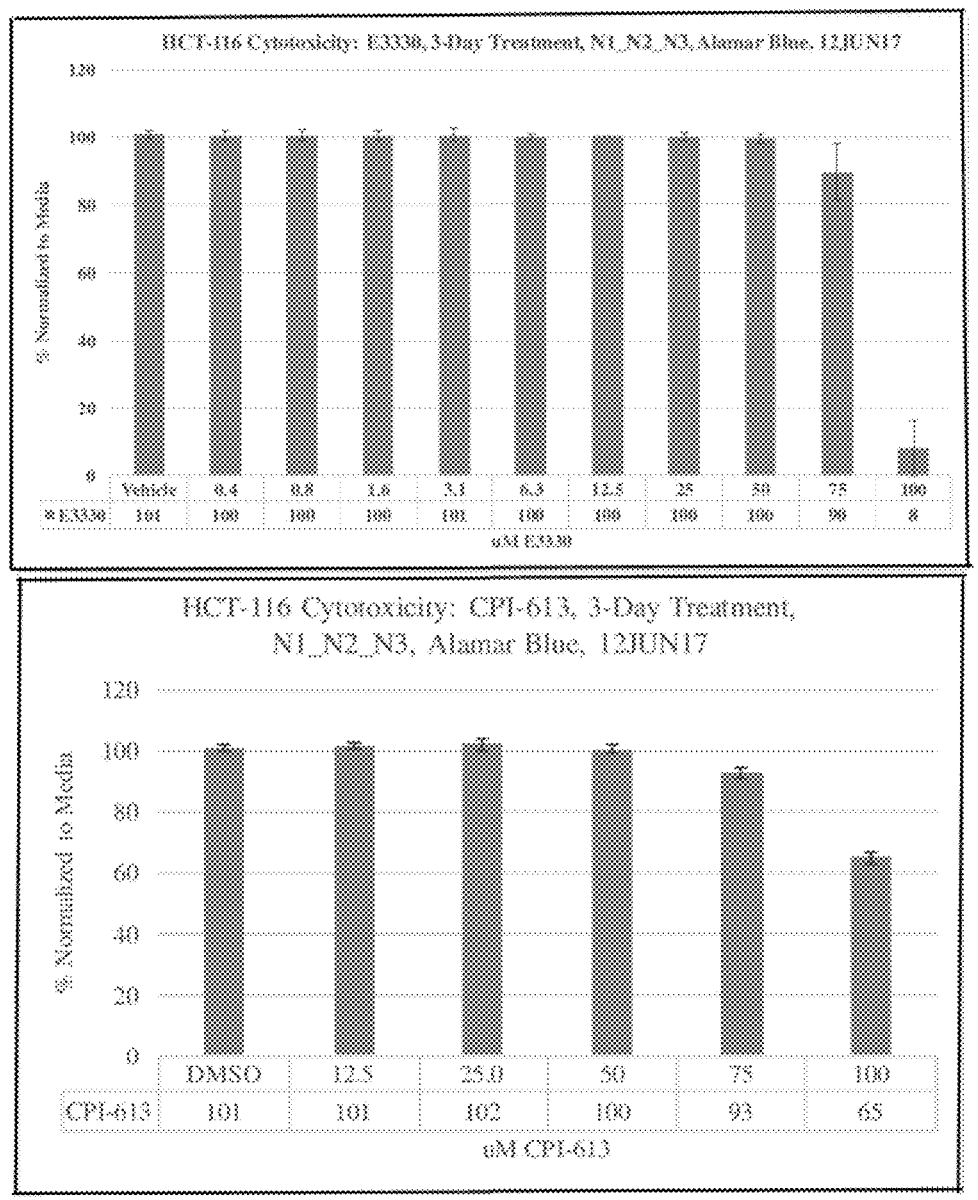
Figures 33B, 33C, 33D, 33E:
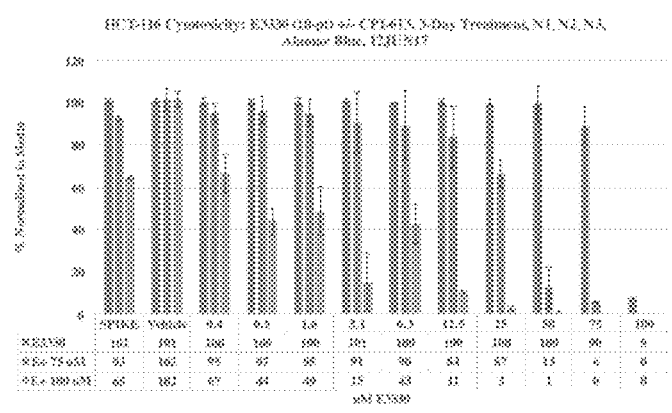

FIGS. 33A-33E depict PDH and alpha-KDH Metabolic inhibitor CPI-613 and Ape1 redox inhibitor APX3330 synergistic drug combination effects in human carcinoma colon cell line HCT-116. FIG. 33A depicts single agent effects. FIG. 33B depicts combination therapy effects. FIG. 33C depicts combination EC50 (μM). FIG. 33D depicts Chou-Talalay Index of dose combinations. FIG. 33E depicts synergy doses.

Figure 34A:
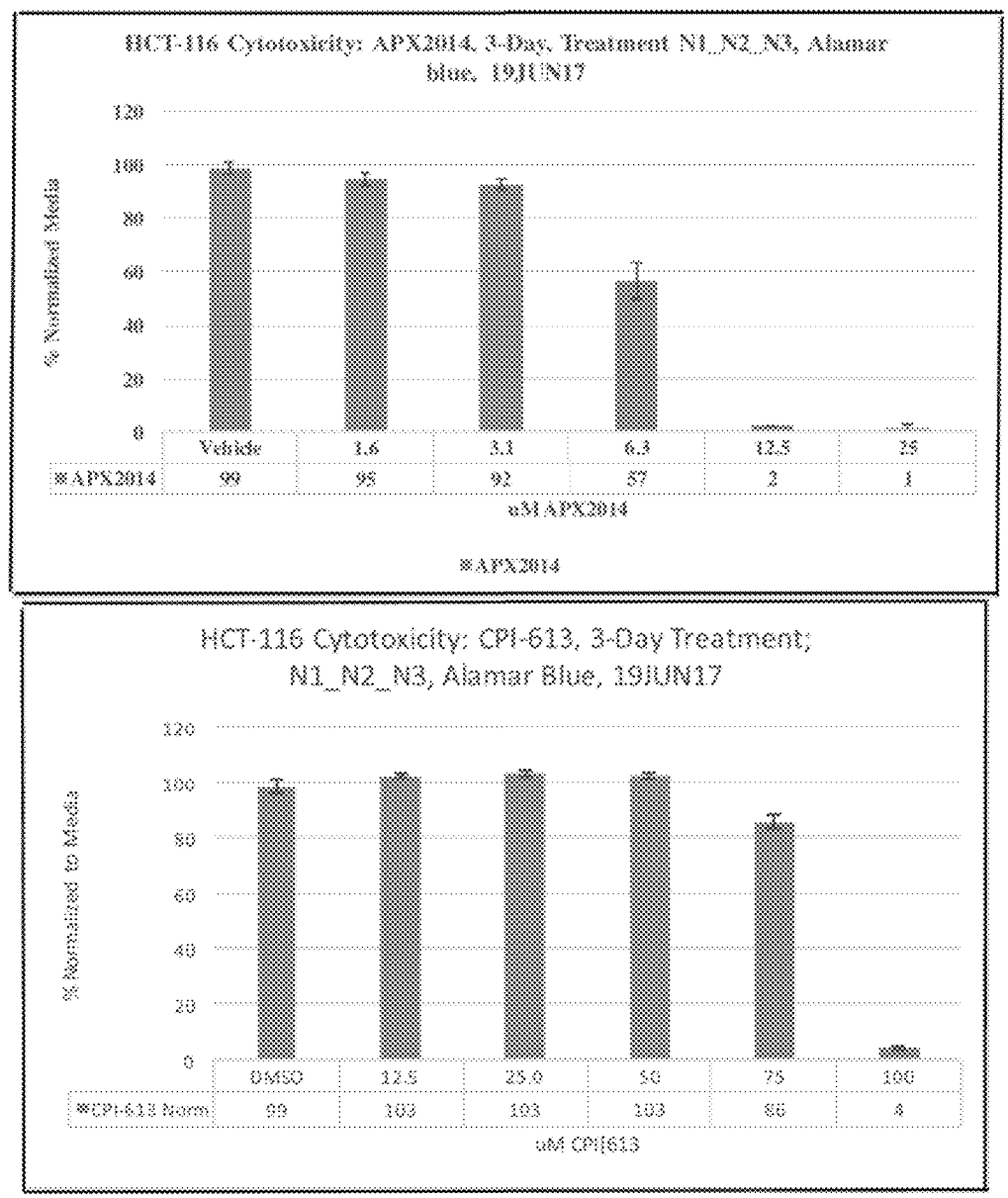
Figures 34B, 34C, 34D, 34E:
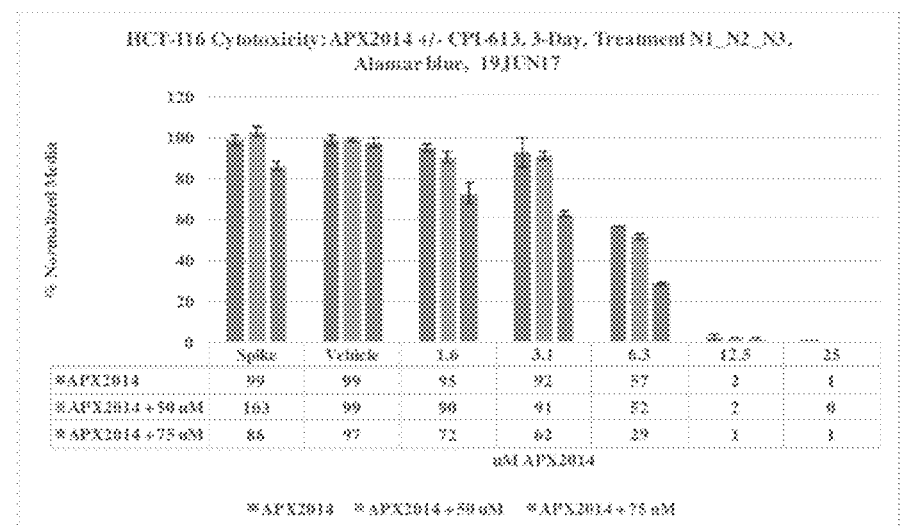

FIGS. 34A-34E depict PDH and alpha-KDH Metabolic inhibitor CPI-613 and Ape1 redox inhibitor APX2014 synergistic drug combination effects in human carcinoma colon cell line HCT-116. FIG. 34A depicts single agent effects. FIG. 34B depicts combination therapy effects. FIG. 34C depicts combination EC50 (μM). FIG. 34D depicts Chou-Talalay Index of dose combinations. FIG. 34E depicts synergy doses.

Figure 35:
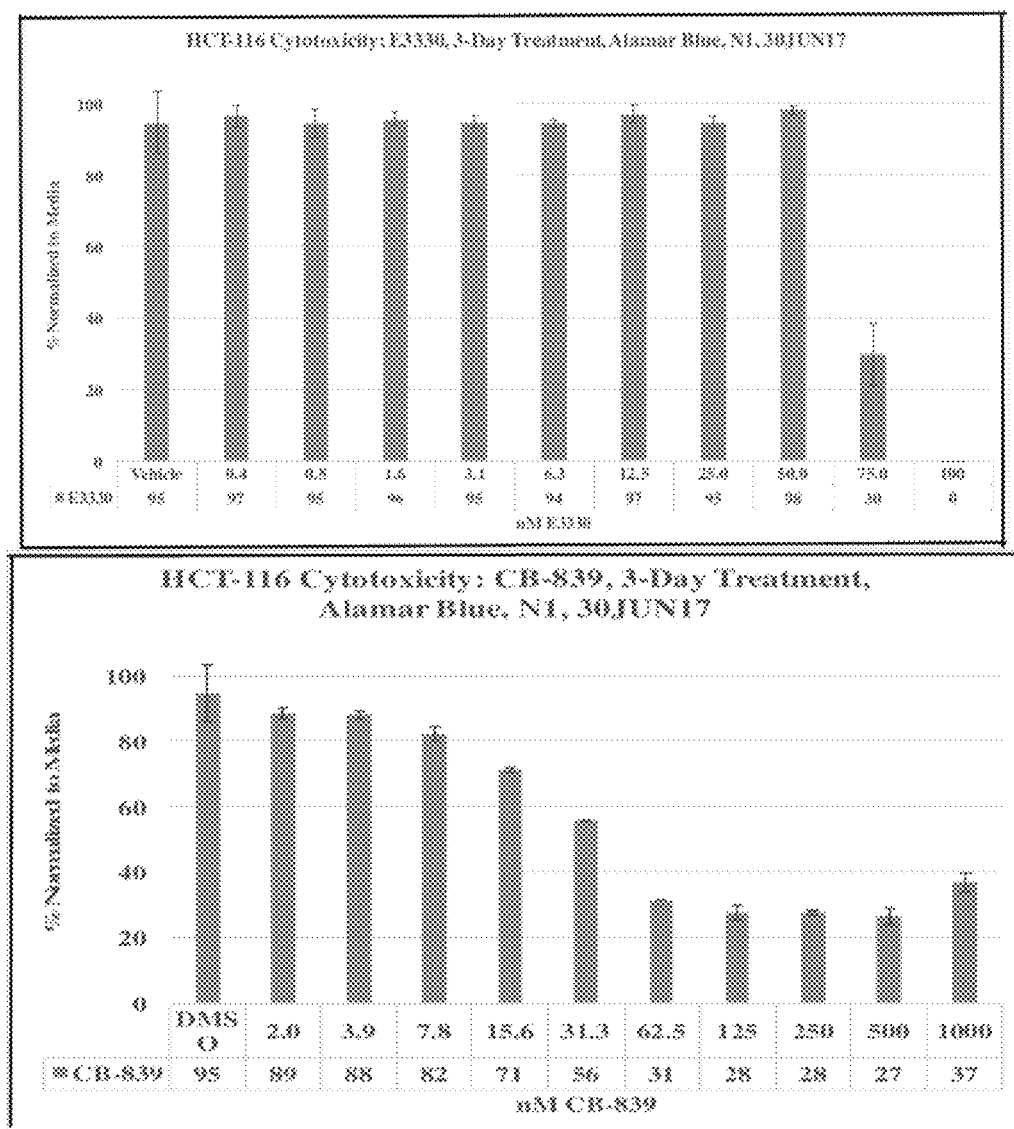
Figures 35B, 35C, 35D, 35E:
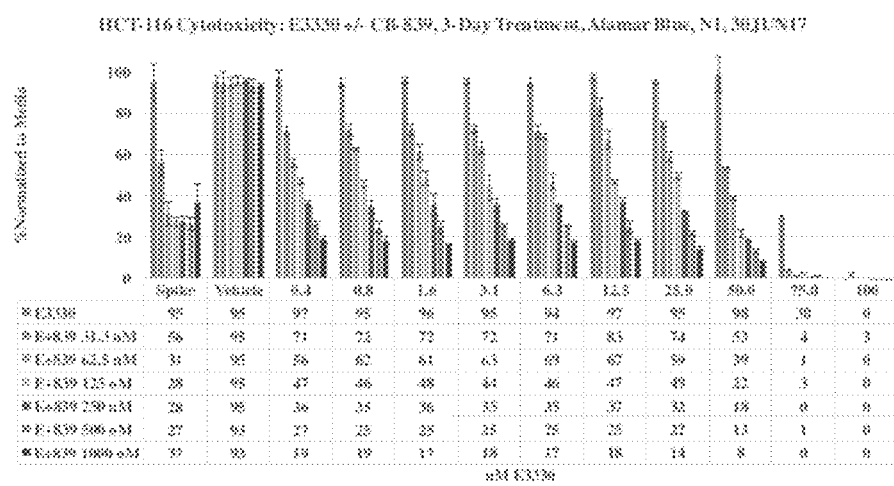

FIGS. 35A-35E depict GLS1 Metabolic inhibitor CB-839 and Ape1 redox inhibitor APX3330 synergistic drug combination effects in human carcinoma colon cell line HCT-116. FIG. 35A depicts single agent effects. FIG. 35B depicts combination therapy effects. FIG. 35C depicts combination EC50 (O4). FIG. 35D depicts Chou-Talalay Index of dose combinations. FIG. 35E depicts synergy doses.

Figure 36A:
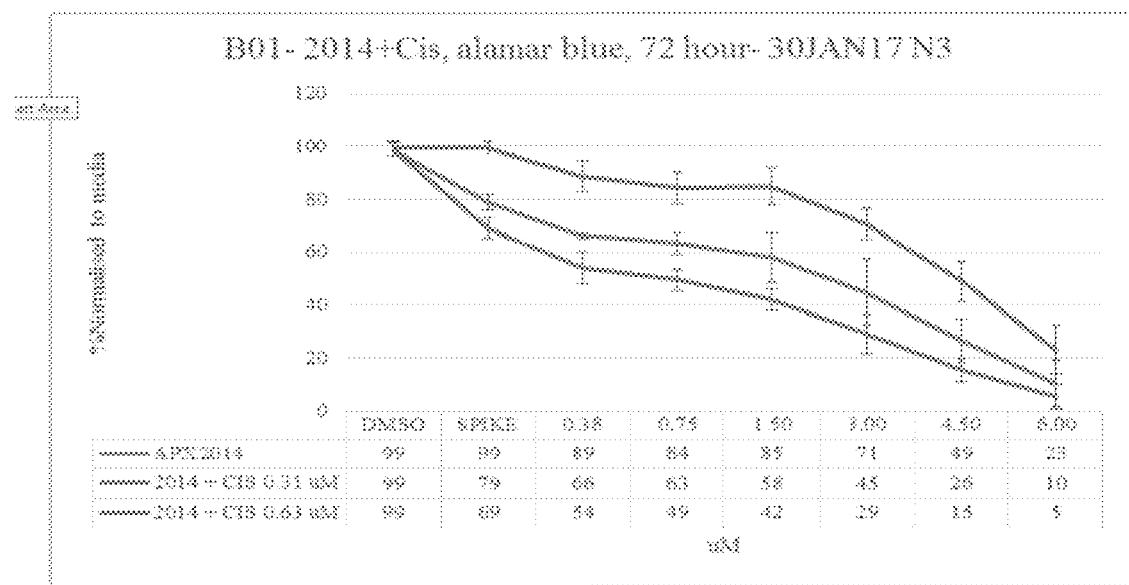
Figure 36B:
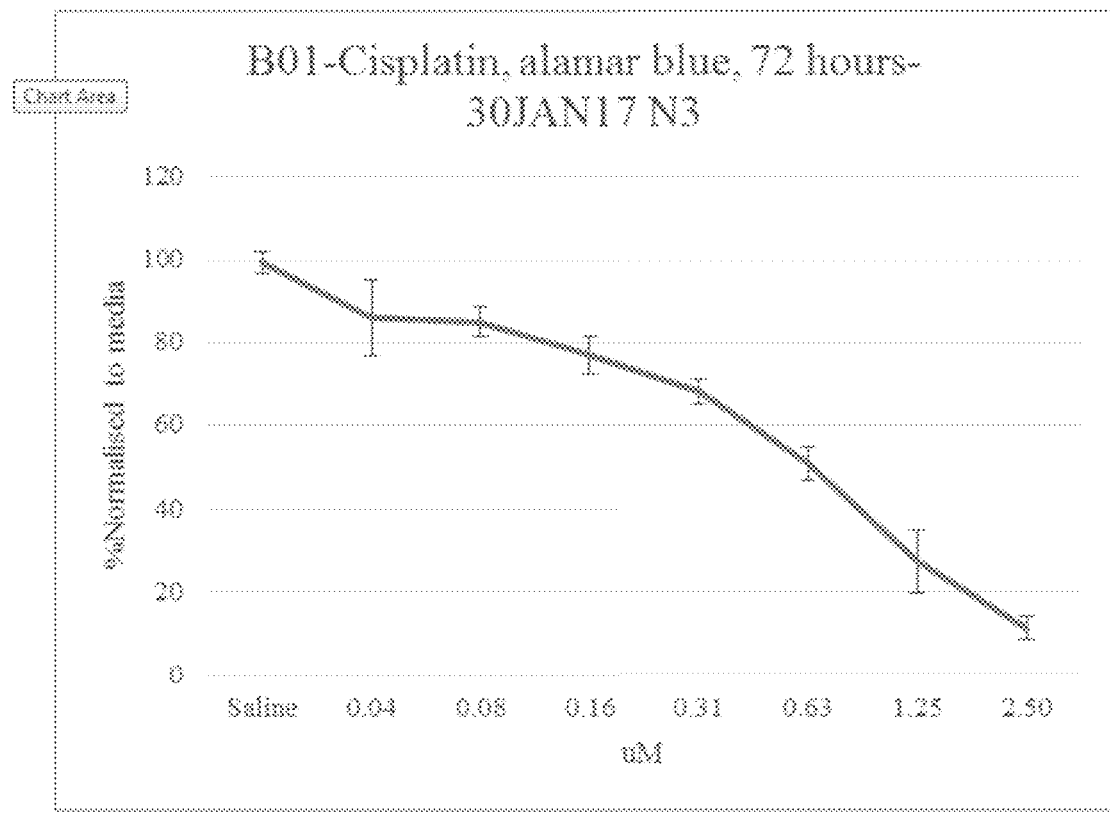

FIGS. 36A & 36B depict the effects of a 3-day treatment of APX2014+/− cisplatin on the cisplatin resistant bladder cell line, BLCAb001.

Figure 37A:
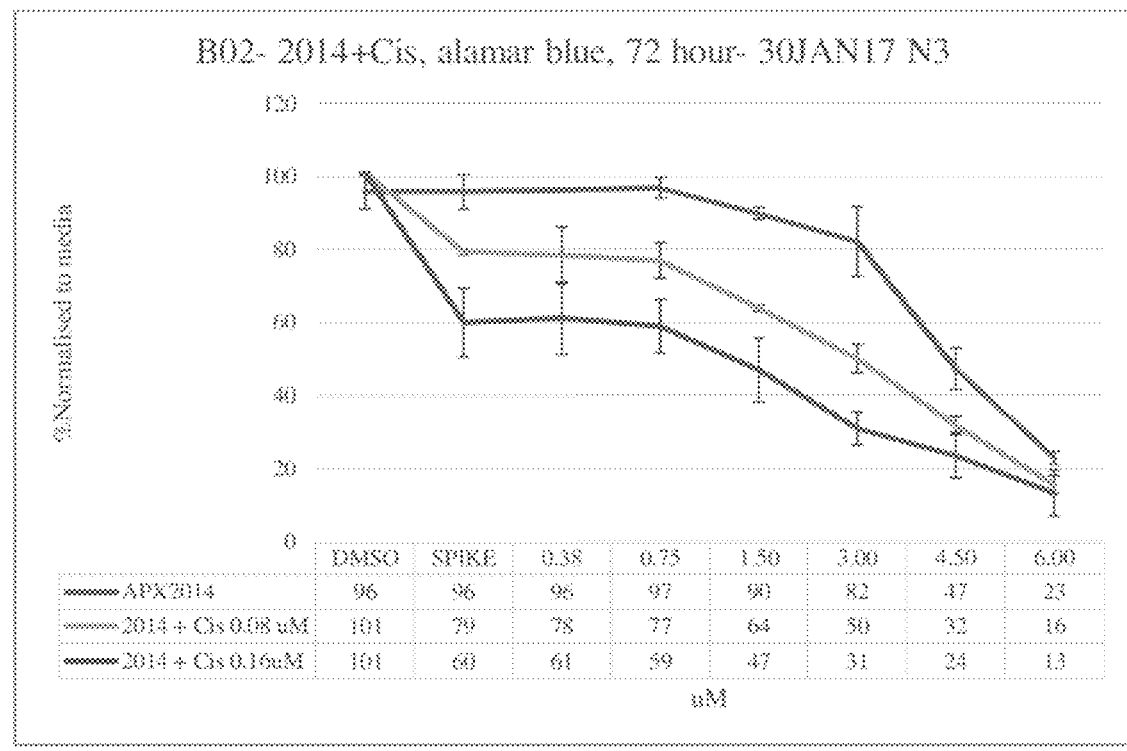
Figure 37B:
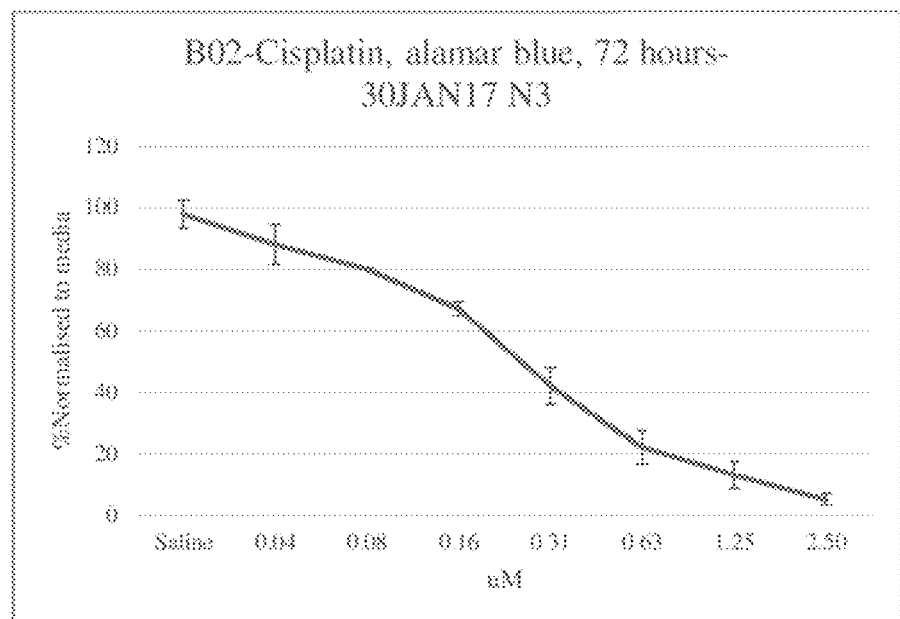

FIGS. 37A & 37B depict the effects of a 3-day treatment of APX2014+/− cisplatin on the cisplatin resistant bladder cell line, BLCAb002.

Figure 38A:
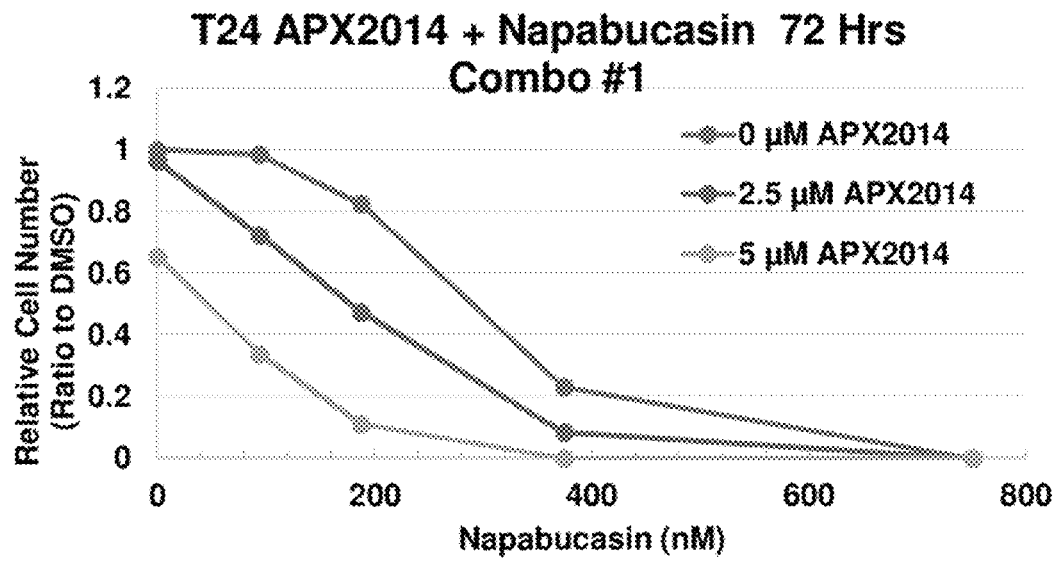
Figure 38B:
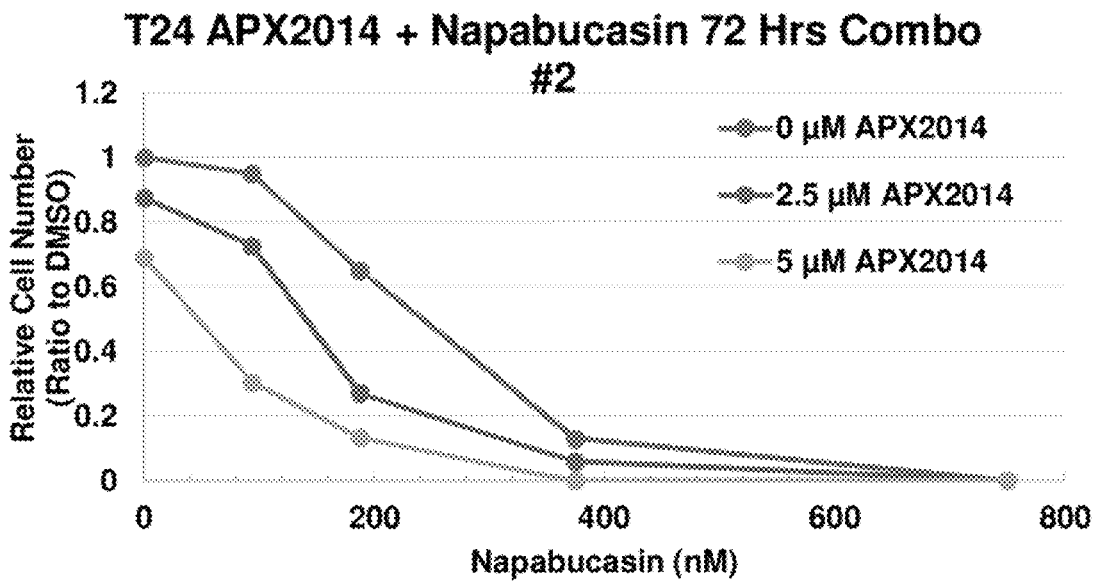

FIGS. 38A & 38B depict the effects of APX2014+/− napabucasin on the bladder cell line, T24.

Figure 39A:
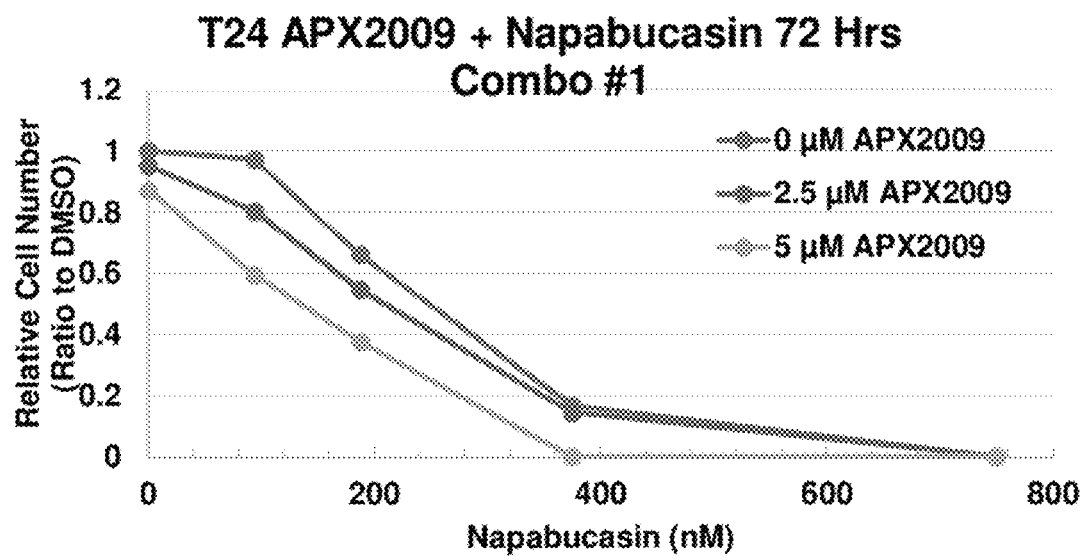
Figure 39B:
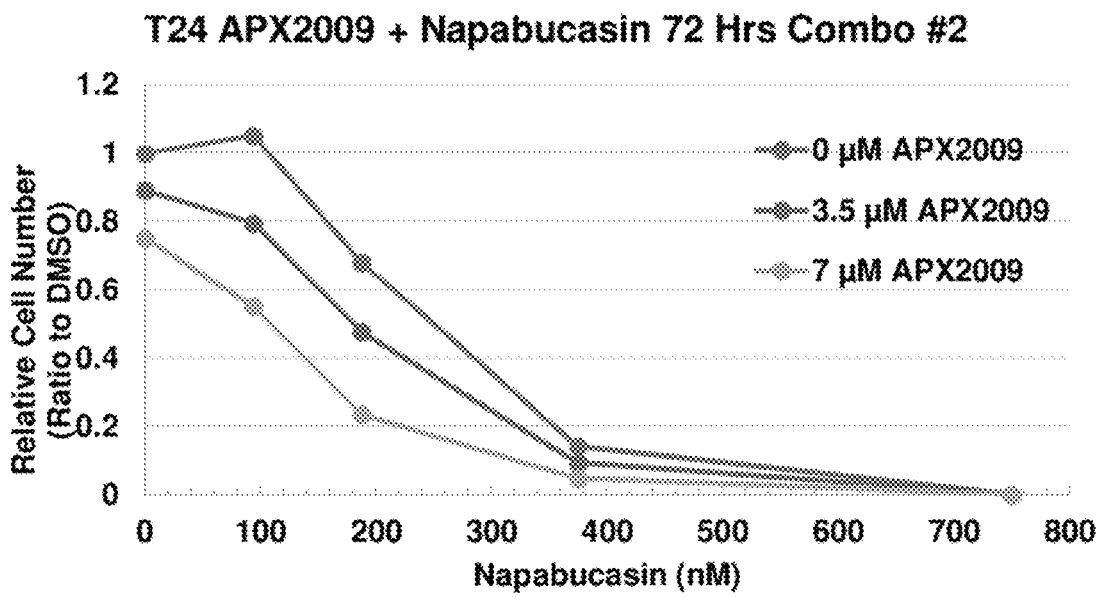

FIGS. 39A & 39B depict the effects of APX2009+/− napabucasin on the bladder cell line, T24.

Figure 40A:
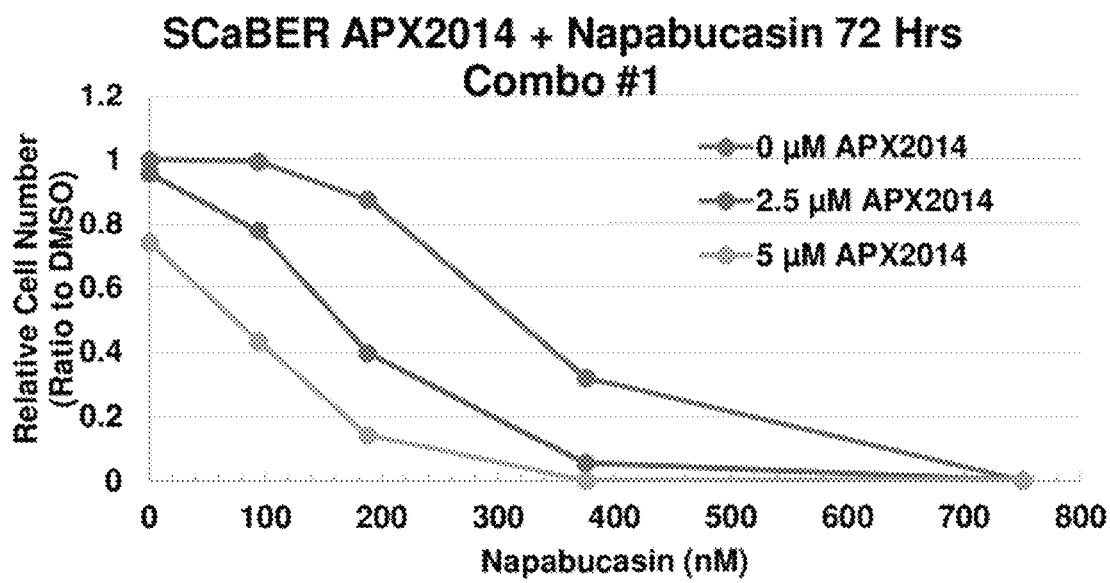
Figure 40B:
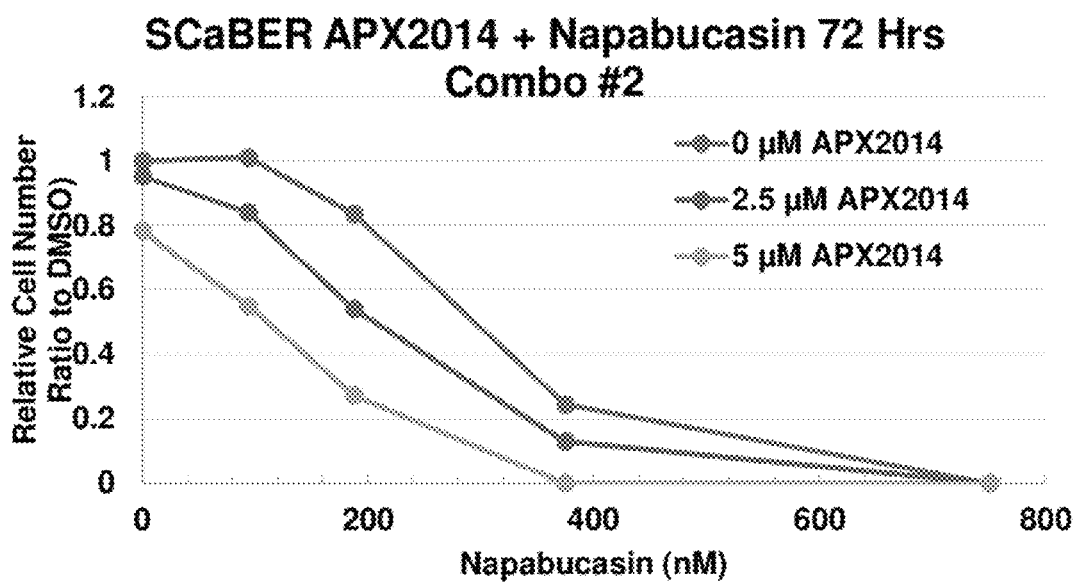

FIGS. 40A & 40B depict the effects of APX2014+/− napabucasin on the bladder cell line, SCaBER.

Figure 41A:
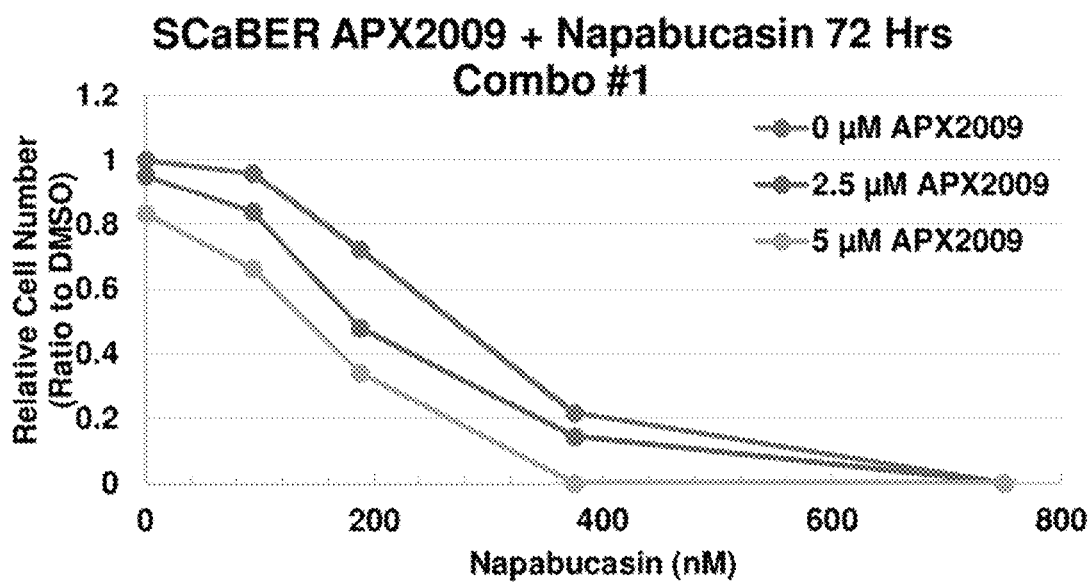
Figure 41B:
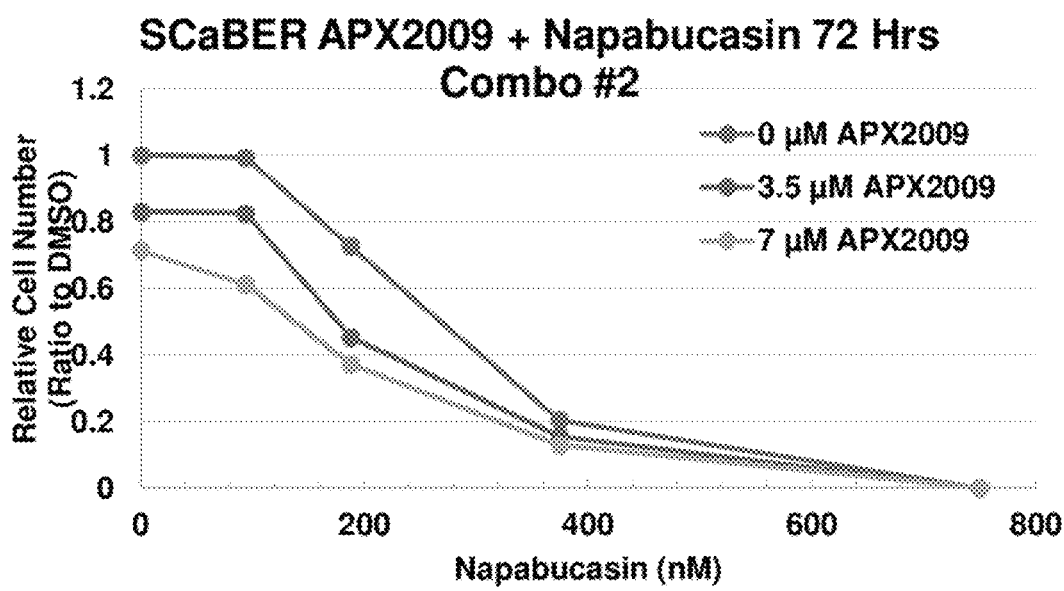

FIGS. 41A & 41B depict the effects of APX2009+/− napabucasin on the bladder cell line, SCaBER.

Figures 42A, 42B, 42C, 42D, 42E, 42F, 42G, 42H:
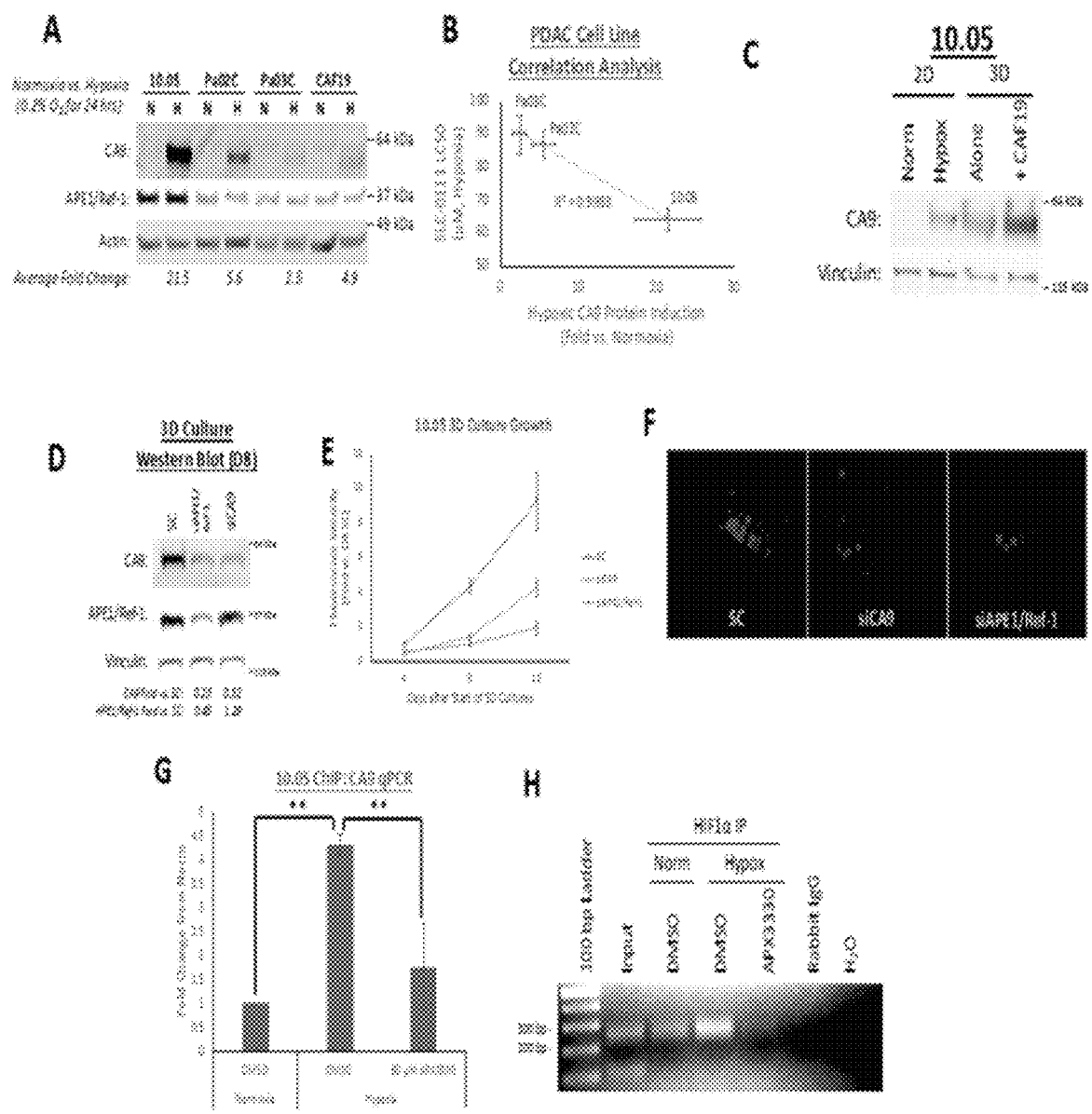

FIGS. 42A-42H depict the importance of the APE1/Ref-1-HIF-1-CA9 signaling axis in PDAC cells. FIG. 42A shows the patient-derived PDAC tumor cell lines 10.05, Pa02C, and Pa03C, as well as the pancreatic CAF cell line CAF19, exposed to 0.2% oxygen for 24 hours. CA9 protein levels were compared via western blot ($p<0.05$ for all cell line differences between normoxia and hypoxia). FIG. 42B shows that LC50 values for SLC-0111 in PDAC cell lines under hypoxic conditions (0.2% 02) are inversely correlated with CA9 induction in each cell line ($R2>0.99$). FIG. 42C depicts 10.05 cells grown in monolayer (2D) and cultured in normoxia or 0.2% 02 for 24 hours and collected for western blot analysis. 10.05 cells alone or in co-culture with CAF19 cells were grown in 3D cultures for 12 days and collected for western blot analysis. Equal amounts of protein were used from all four samples. CA9 levels in 3D cultures alone and with CAFs were 2.5 and 6.2-fold greater (respectively) than in hypoxia-exposed monolayer cultures. FIGS. 42D-42F show 10.05 cells transfected with the indicated siRNAs and cultured in 3D spheroids. Cells were collected for western blot analysis on D8 to confirm knock-down (FIG. 42D, $p<0.05$ for siAPE1/Ref-1 and siCA9 effects on CA9 as well as siAPE1/Ref-1 effects on APE1/Ref-1). Fluorescence intensity (FIG. 42E) and area (not shown) were measured on days 4, 8, and 12 of 3D culture growth ($p<0.001$ for differences between knockdown groups and SC on D12, $p<0.05$ for difference between siAPE1/Ref-1 and siCA9 on D12). Representative fluorescent images from each group were captured on day 12 (FIG. 42F). FIGS. 42G-42H depict 10.05 cells treated with APX3330 and exposed to 0.2% $O_2$ for 12 hours prior to protein-DNA cross-linking and collection. IPs of HIF1α and a control for non-specific binding (Rabbit IgG–performed on DMSO+Hypoxia sample) were performed using nuclear extracts. qPCR for the HBS-containing region of the CA9 promoter was performed. (FIG. 42G, **$p<0.01$). PCR for the HBS-containing region of the CA9 promoter was performed using IP samples as well as input DNA (1% of amount loaded into IPs–performed on DMSO+Hypoxia sample) and a negative control (H2O), and these samples were detected on a 1% agarose gel with ethidium bromide (FIG. 42H, expected product size=249 bp).

Figures 43A, 43B, 43C, 43D, 43E:
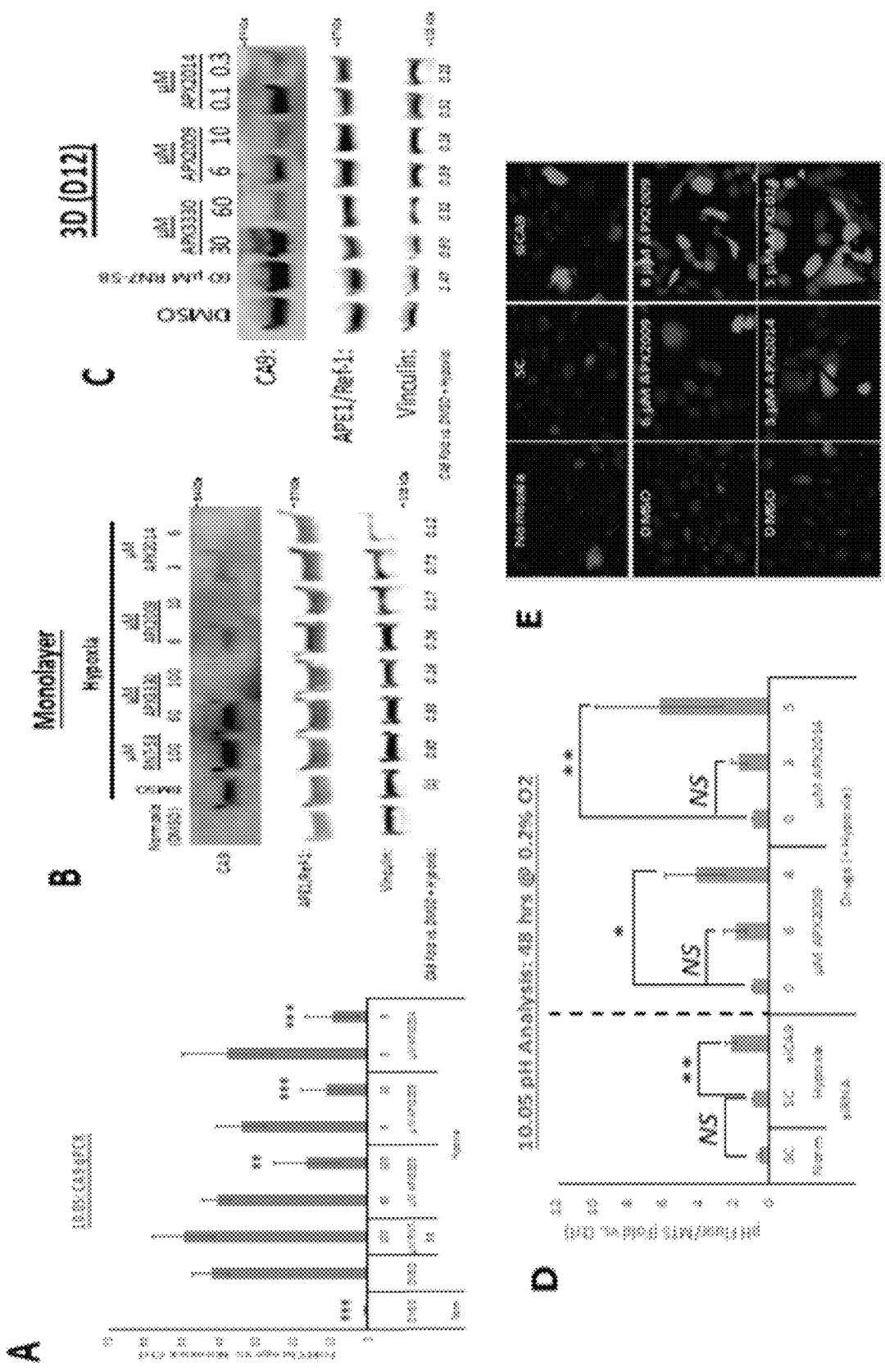
Figures 43F, 43G, 43H, 43I:
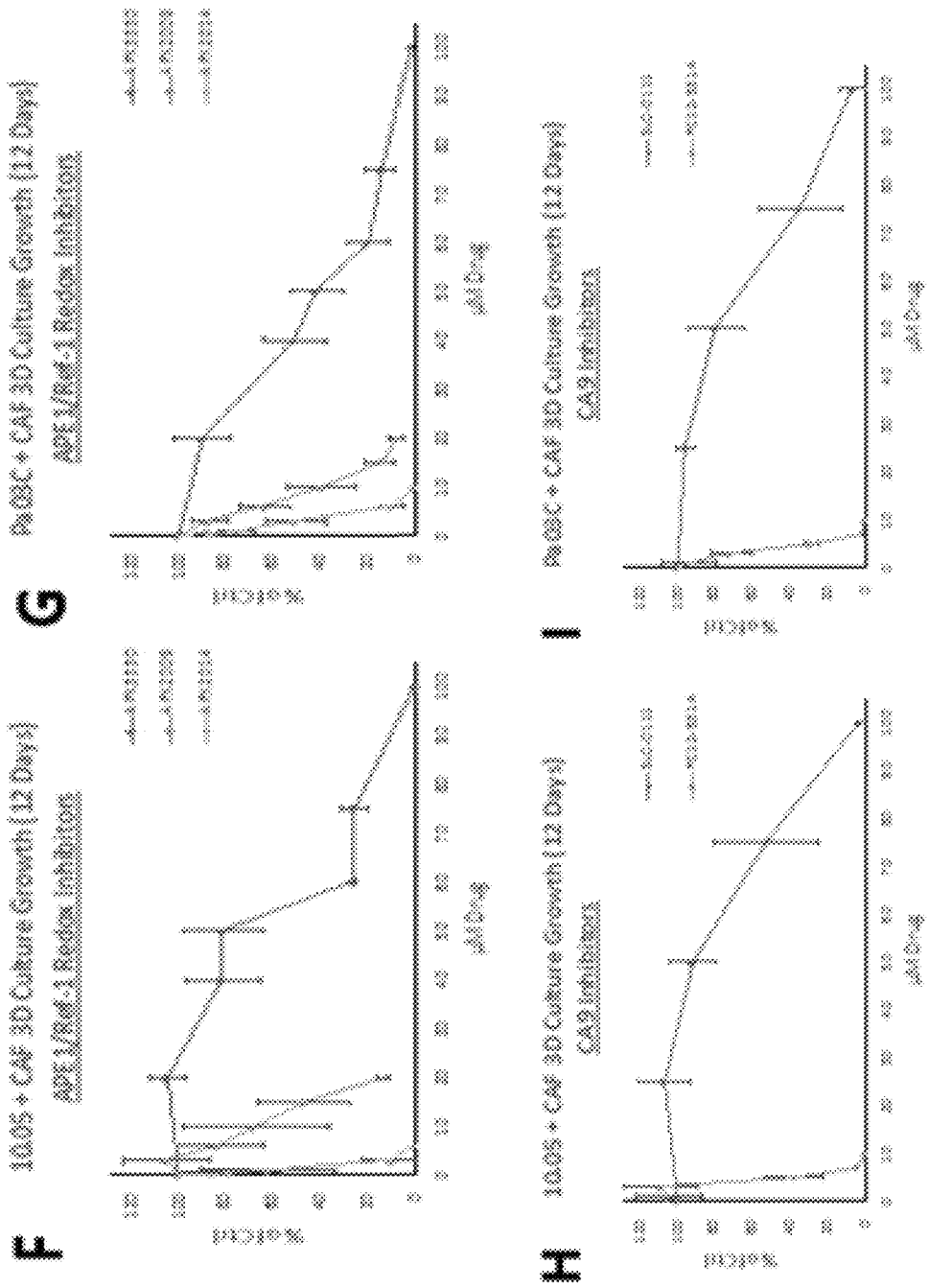

FIGS. 43A-43I depict blockade of CA9 via APE1/Ref-1 or CA9 inhibition. FIGS. 43A & 43B show 10.05 cells treated with APX3330, APX2009, APX2014, and the negative analog RN7-58 and exposed to 0.2% 02 for 24 hours prior to collection and analysis of CA9 mRNA (FIG. 43A) and protein (FIG. 43B) levels ($p<0.01$ for differences in CA9 mRNA and protein levels at the highest concentration tested of each APE1/Ref-1 inhibitor vs. DMSO). FIG. 43C show 10.05 cells cultured in 3D spheroids for 12 days prior to collection and Western Blot analysis. Cultures were treated with the indicated concentrations of APX3330, APX2009, APX2014, and the negative analog RN7-58 on days 4 and 8 ($p<0.05$ for differences in CA9 expression at the highest concentration tested of each APE1/Ref-1 inhibitor vs. DMSO). FIGS. 43D & 43E show 10.05 cells transfected with the indicated siRNAs or treated with the indicated concentrations of APX2009 or APX2014 and exposed to 0.2% $O_2$ for 48 hours. Changes in intracellular pH were quantified using a pH-sensitive fluorescent dye (pHrodo Red channel, FIG. 43D), and pH-mediated fluorescence changes were imaged by a blinded third party (FIG. 43E). FIGS. 43F-43I show 3D co-cultures with 10.05 (FIGS. 43F & 43H) or Pa03C (FIGS. 43G & 43I) tumor cells (+CAFs) were treated with increasing concentrations of APX3330, APX2009, and APX2014 (F-G) or SLC-0111 and FC12-531A (FIGS. 43H & 43I) for 12 days, and fluorescence intensity was measured.

FIGS. 44A-44F depict characterization of 3D cultures and effects of dual-targeting APE1/Ref-1 and CA9. FIGS. 44A-44F depict spheroids consisting of 10.05 or Pa03C cells cultured with CAFs for 12 days and collected for IHC. Slides with sections from these cultures were stained with the indicated antibodies/stains. Antibody stains (FIGS. 44B and 44D-44F) were counter-stained with hematoxylin. Images are 1,600× magnification.

Figures 45A, 45R:
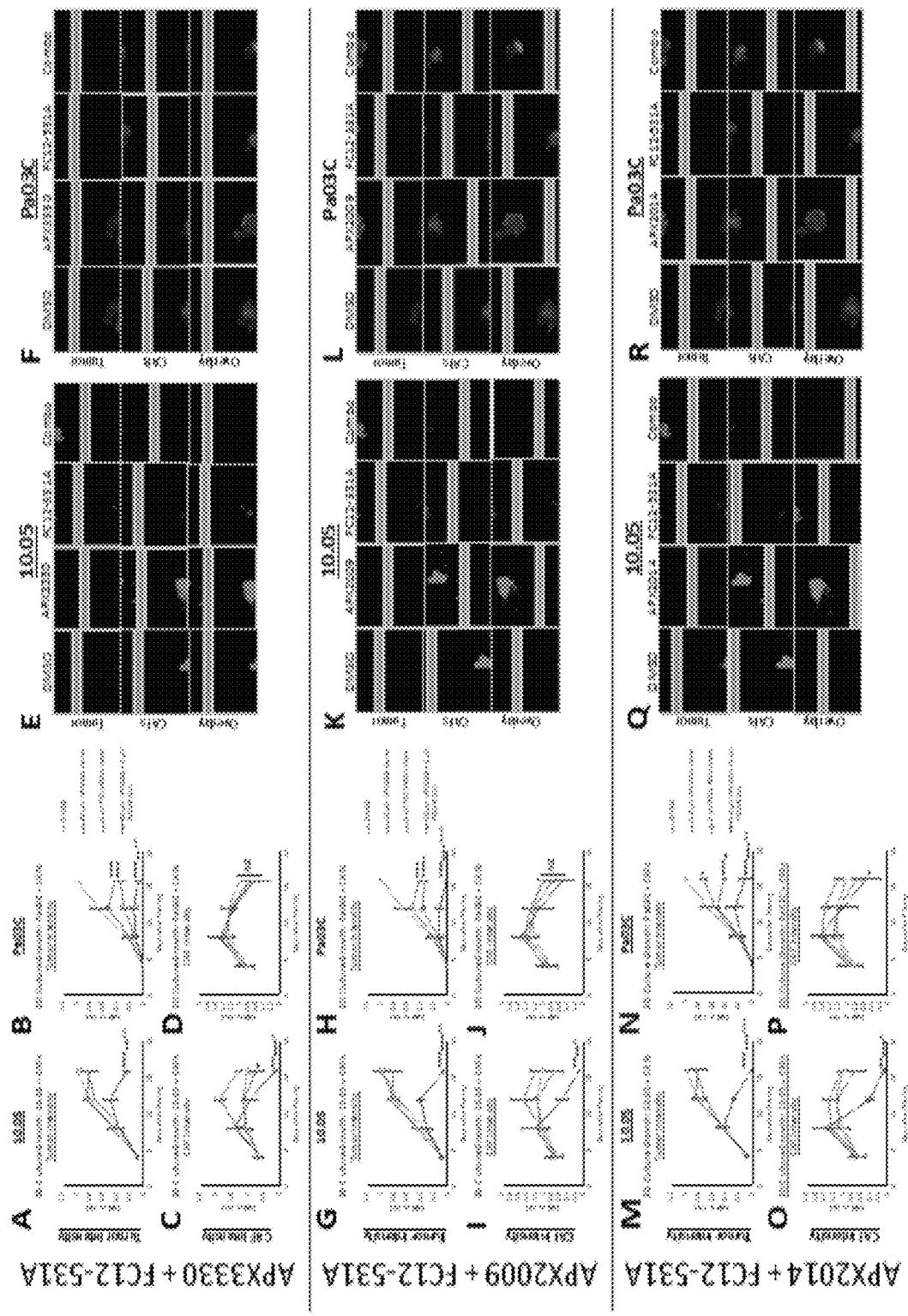

FIGS. 45A-45R depict APE1/Ref-1 redox signaling inhibition sensitizes 3D PDAC tumor spheroids to CA9 inhibition with second-generation inhibitors. 10.05 and Pa03C cells were plated into 3D cultures with CAF19 cells, and cell growth in these spheroids was measured via fluorescence intensity on days 4, 8, 12, and 16 after plating. The growth of tumor cells vs. CAF cells in the spheroid co-cultures was assessed separately using different fluorescent labels in the two cell types. 3D cultures were treated with FC12-531A+ APX3330 (FIGS. 45A-45F), APX2009 (FIGS. 45G-45L), or APX2014 (FIGS. 45M-45R) following measurements on days 4, 8, and 12. Fluorescence intensity data within each experiment were normalized to day 16 DMSO ctrl, and day 16 readings were compared. Differences between groups were determined using Tukey's multiple comparisons test: *$p<0.05$ vs. DMSO; $p<0.01$ vs. DMSO; *$p<0.001$ vs. DMSO; +$p<0.05$ vs. APE1/Ref-1 Inhibitor; ++$p<0.01$ vs. APE1/Ref-1 Inhibitor; +++$p<0.001$ vs. APE1/Ref-1 Inhibitor; ^$p<0.05$ vs. FC12-531A; ^^$p<0.01$ vs. FC12-531A; ^^^$p<0.001$ vs. FC12-531A. Graphs are means with standard deviations of N=3. Fluorescent images of Tumor (red channel) and CAF (green channel) cells in these spheroids were captured on day 16.

Figure 46:
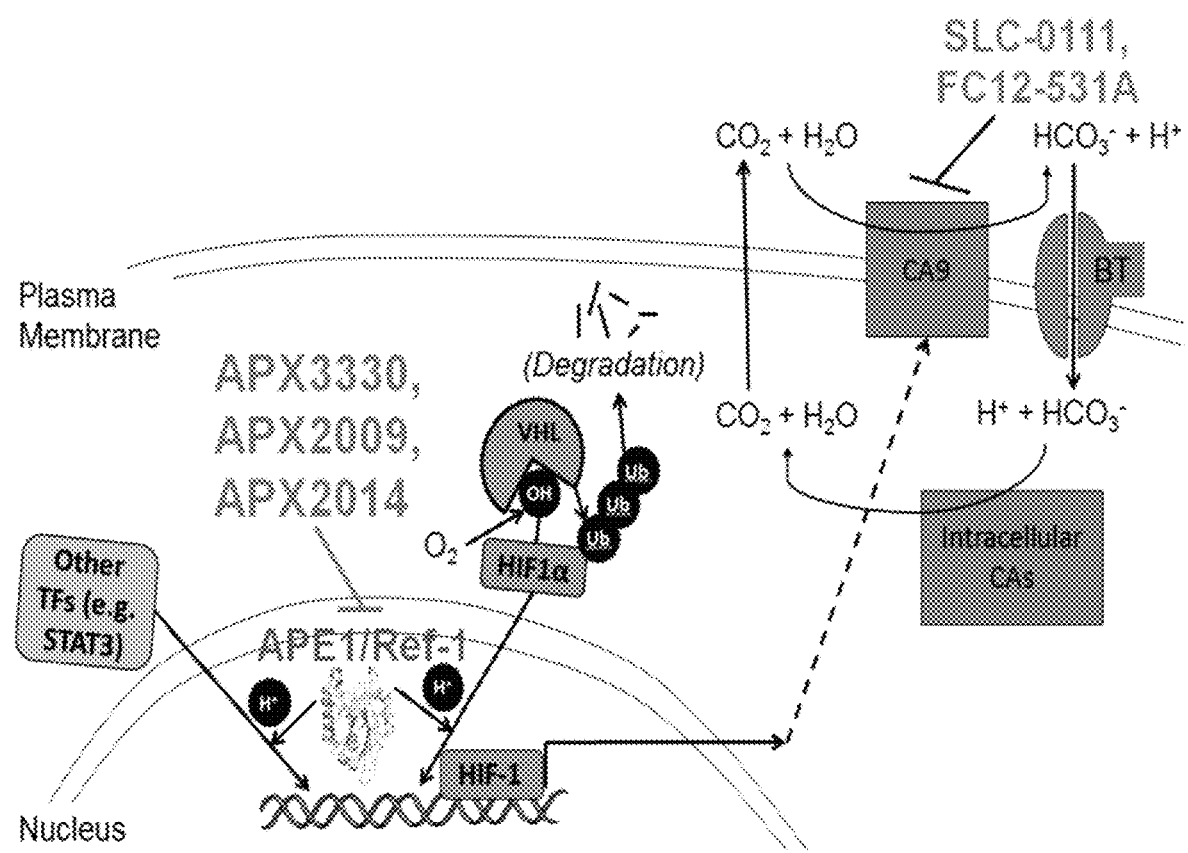

FIG. 46 is a pathway schematic. APE1/Ref-1 redox signaling contributes to the transactivation of HIF-1 and certain other transcription factors. HIF1α is stabilized under hypoxic conditions, leading to the formation of HIF-1 and subsequent expression of CA9. CA9 coordinates with the bicarbonate transporter and intracellular CAs to stabilize intracellular pH. APE1/Ref-1 redox signaling inhibition (with APX3330, APX2009, or APX2014) attenuates HIF-1-mediated CA9 expression, sensitizing tumor cells to CA9 inhibition (with SLC-0111 or FC12-531A).

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Cancer

The multi-functional nature of Ref-1 alludes to its expansive roles in disease, particularly cancers. Ref-1 is upregulated in many cancers (Table 1, FIG. 4). This increase is frequently associated with tumorigenesis, cancer aggressiveness, increased angiogenesis, radiotherapeutic and chemotherapeutic resistance, and overall poor prognosis. This makes Ref-1 and the transcription factors it regulates prime targets for anticancer therapies.

TABLE 1

| Tumor tissues/cells with increased Ref-1 expression Cancer with increased Ref-1 expression |
|---|
| Prostate |
| Pancreatic |
| Cervical |
| Ovarian |
| Osteosarcoma |
| Germ cell tumor |
| Colon/Colorectal |
| Bladder |
| Head and Neck |
| Gastric/Gastro-esophageal |
| Neuroectodermal tumors |

TABLE 1-continued

| Tumor tissues/cells with increased Ref-1 expression Cancer with increased Ref-1 expression |
|---|
| Rhabdomyosarcomas |
| Pancreaticobiliary |
| Adult gliomas |
| Non-Small Cell Lung |
| Hepatocellular |
| Multiple Myeloma |
| Esophageal |
| Breast |
| Pediatric Ependymoma |
| Melanoma |

Prostate Cancer

One of the most widely studied cancers that exhibits Ref-1 overexpression is prostate cancer. Overexpression is seen immunohistologically as a higher percentage of cells staining positive for Ref-1 in the cytoplasm and an increased intensity of Ref-1 nuclear staining.

One of the main targets of Ref-1 redox signaling in prostate cancer is STAT3, which is constitutively active in prostate cancer. STAT3 inhibition suppresses prostate cancer cell growth. Conversely, STAT3 activation negatively affects overall survival rates and shortens relapse-free survival (RFS). 95% of metastatic samples taken from patients who died of castration-resistant prostate cancer were positive for pSTAT3, with the highest expression seen in bone metastases samples. Collectively, this supports the crucial role of pSTAT3 in prostate cancer aggressiveness and progression.

A downstream target of STAT3 is survivin; its increased expression is also associated with prostate cancer aggressiveness. mRNA expression levels of survivin in prostate biopsy tissues show significantly higher survivin expression in cancerous tissue, which correlates with higher-grade cancer and aggressive phenotypes. siRNA knockdown of survivin in prostate cancer cell lines reduces cell proliferation and increases chemosensitivity to the apoptosis-inducing agent cisplatin. The effects of decreased survivin expression extend in vivo. Mice injected subcutaneously with siRNA survivin knockdown cells exhibit significantly smaller tumors compared with controls.

Interestingly, Ref-1 redox-specific inhibitors APX3330 and APX2009 decreased survivin mRNA and protein levels in prostate cancer cells by affecting NF-κB activity. These inhibitors also reduced cell proliferation. In vivo, APX2009 reduced survivin protein levels and cell proliferation.

Based on the evidence, both STAT3 and survivin present as prime targets for anti-prostate cancer therapies. However, to date they have been only moderately successful as single-agent therapies. Therefore, the potential combination of inhibiting both Ref-1 redox function and STAT3/survivin provides an avenue of targeting both the overarching regulator and downstream effector of an anti-apoptotic pathway integral to prostate cancer.

In one suitable embodiment, the present disclosure is directed to the combination of an APE1/Ref-1 inhibitor (5-(2,3-dimethoxy-6-methyl 1,4-benzoquinoyl)]-2-nonyl-2-propenoic acid (APX3330), [(2E)-2-[(3-methoxy-1,4-dioxo-1,4-dihydronaphthalen-2-yl)methylidene]-N,N-diethylpentanamide] (APX2009), (2E)-2-[(3-methoxy-1,4-dioxo-1,4-dihydronapthalen-2-yl)methylidene]-N-methoxypentanamide] (APX2014)) and a STAT3 inhibitor (e.g., napabucasin) for treating prostate cancer. In another embodiment, a combination of an APE1/Ref-1 inhibitor and a survivin inhibitor (e.g., YM155) for treating prostate cancer is disclosed.

Colon Cancer

Colon cancer, the second leading cause of cancer related death in the U.S., exhibits increased levels of cytoplasmic Ref-1. In liver tumor tissue of metastasized colorectal cancer, increased Ref-1 expression corresponds to poor patient outcome. In colony-forming assays, siRNA Ref-1 knockdown significantly increases the sensitivity of colon cancer cells to ionizing irradiation (IR). Furthermore, in vivo subcutaneous xenografts also show reduced tumor growth and radiosensitization following intratumoral Ref-1 siRNA treatment.

The importance of Ref-1 redox signaling in colon cancer is highlighted by the effects that the Ref-1 redox inhibitor APX3330 has on colon cancer stem cells (CCSCs). APX3330 (hereafter referred to as "APX") significantly reduces CCSC growth in vitro and enhances the cytotoxicity of 5-fluorouracil (5-FU), an anti-metabolite chemotherapeutic. In xenograft mice injected subcutaneously with CCSCs, intratumoral administration of APX3330 increases tumor response to 5-fluorouracil (5-FU) delivered intraperitoneally. This indicates that APX3330 could potentiate other colon cancer treatments by inhibiting Ref-1's crucial redox activity.

Additionally, as shown below, when APX3330 was combined with CPI-613, a lipoate analog known to inhibit the mitochondrial enzymes pyruvate dehydrogenase (PDH) and α-ketoglutarate dehydrogenase (KDGH), there was a significant killing effect in colon cancer cells.

In one suitable embodiment, the present disclosure is directed to the combination of an APE1/Ref-1 inhibitor (APX3330, APX2009 and APX2014) and a chemotherapeutic (e.g., 5-FU) for treating colon cancer. In another embodiment, a combination of an APE1/Ref-1 inhibitor and an inhibitor of PDH and/or KDGH (e.g., CPI-613) for treating colon cancer is disclosed.

Ovarian Cancer

Ref-1 expression in ovarian cancer has been studied widely. Ref-1 expression is increased in malignant patient tissue samples, but studies vary as to the location of this increase.

Some studies show increased expression primarily in the cytoplasm. In those studies, cytoplasmic localization of Ref-1 correlates with ovarian tumor progression. Additionally, patients with advanced (stage III/IV) cancer have significantly higher Ref-1 expression and lower overall survival rates than stage I/II patients. Patients with increased cytoplasmic Ref-1 are also more resistant to platinating chemotherapeutics. A different study observed increased Ref-1 nuclear expression, again with greater increases in stage III/IV compared to stage I/II patients. In other studies, both nuclear and cytoplasmic Ref-1 expression were increased, but no correlation was observed between Ref-1 expression and the cancer stage. Collectively, these studies highlight that, while Ref-1 expression clearly plays a role in ovarian cancer, the heterogeneity of tissue samples makes it hard to discern the roles of Ref-1 nuclear versus cytoplasmic localization.

However, reduced expression of Ref-1 has a clear effect on ovarian cancer cells. Ref-1 knockdown in A2780 (nuclear APE1) and CP70 (cytoplasmic APE1) cells sensitizes both to cisplatin. In SKOV3 and A2780 cells, Ref-1 siRNA significantly reduces cell proliferation, colony formation, migration and invasion. Similarly, Ref-1 siRNA treatment of SKOV-3× ovarian cancer cells significantly reduces their growth; the same occurs with APX3330 redox inhibition. Ref-1 siRNA cells implanted subcutaneously in mice show markedly reduced growth compared to control tumors: a 3.2-fold increase in tumor-doubling time (from 5 to more than 15 days). The tumors also exhibit reduced glucose metabolism. Taken together, a strong case can be made for targeting Ref-1 in ovarian cancer as a means to inhibit growth as well as enhance activity of other anticancer drugs.

Non-Small Cell Lung Carcinoma

Ref-1 has long been considered a prognostic marker in non-small-cell lung carcinoma (NSCLC), as Ref-1 protein levels are upregulated in patient tumor samples. Nuclear Ref-1 expression in tissue samples presents better survival chances for patients. Cytoplasmic Ref-1 and mRNA expression correlate strongly with poor patient survival and shorter RFS. Both immunohistochemistry and immunoblotting show increased cytoplasmic and reduced nuclear Ref-1 expression in patients with a recurrence of stage I NSCLC. Post-treatment serum Ref-1 levels are inversely associated with overall survival.

Ref-1 affects platinum-based drugs commonly used in NSCLC. An increase in Ref-1 expression in NSCLC confers resistance to cisplatin treatment, while Ref-1 siRNA knockdown in A549 cancer cells significantly enhances cisplatin cytotoxicity. Patients with tumors not expressing Ref-1 respond better to platinum-paclitaxel therapy and cisplatin-docetaxel-gemcitabine treatment, with longer time to progression and overall survival.

Evidence exists that reducing Ref-1 increases the efficacy of other anticancer treatments in NSCLC. Decreasing Ref-1 levels in A549 cells in vitro and in vivo increases the effectiveness of photodynamic therapy. Ref-1 knockdown with shRNA enhances the anti-tumor activity of oxymatrine, an alkaloid compound that inhibits proliferation of A549 cells.

Collectively, this demonstrates that Ref-1 plays a vital role in NSCLC progression, and targeting it might lead to better patient outcomes when combined with various chemotherapeutic treatments.

In one embodiment, the present disclosure is directed to a combination of an APE1/Ref-1 inhibitor (e.g., APX3330, APX 2009 and APX2014) and a chemotherapeutic agent (e.g., paclitaxel, cisplatin, docetaxel, gemcitabine) for treating NSCLC. In another embodiment, a combination of an APE1/Ref-1 inhibitor and a photodynamic therapy for treating NSCLC is disclosed.

Malignant Peripheral Nerve Sheath Tumors

Malignant Peripheral Nerve Sheath Tumor (MPNST) is an uncommon neural-origin cancer that can be deadly. Despite much research to date, existing chemotherapeutic agents have not been successful in MPNST treatment. Recent research implicates Ref-1 redox targets HIF-la and particularly STAT3 in driving MPNST.

Phosphorylated STAT3 expression may indicate aggressive disease at disease onset. A tissue microarray showed STAT3 expression in primary MPNST was associated with worse disease-specific overall survival and event-free survival. In a mouse model of EGFR overexpression, both a JAK/STAT3 inhibitor and STAT3 knockdown by shRNA prevented tumor formation.

In another study, inhibition of STAT3 activation in four MPNST lines resulted in decreased wound healing, cell migration, invasion, and tumor formation. It also reduced HIF-1α expression. Independent shRNA-mediated HIF-1α knockdown also decreased wound healing, cell migration, invasion, and tumor formation, showing that the STAT3/HIF-1 α signaling pathway is responsible for tumorigenesis in MPNST.

Furthermore, STAT3's downstream target survivin is amplified in MPNSTs. Survivin is highly expressed in MPNST tissue samples. Survivin knockdown via siRNA decreases cell growth, inhibits cell cycle progression and increases apoptosis. Additionally, survivin inhibitor YM155 represses MPNST xenograft growth and metastasis in vivo.

The role of the STAT3-HIF-1α pathway in MPNST supports the notion of STAT3 and/or HIF-1α inhibition as a potential way to treat MPNST. Downstream markers like survivin also present as potential targets. Ref-1 regulates STAT3 as well as HIF-1α; therefore, targeting Ref-1 would inhibit multiple targets, providing hope for a viable treatment for MPNST. Additionally, the possibility of dual targeting Ref-1 and either STAT3 or HIF-1α alludes to the potential of completely eliminating a pathway that is integral to MPNST progression.

In one embodiment, the present disclosure is directed to a combination of an APE1/Ref-1 inhibitor (e.g., APX3330, APX 2009 and APX2014) and a STAT3 inhibitor (e.g., napabucasin) for treating MPNST. In another embodiment, a combination of an APE1/Ref-1 inhibitor and a HIF-1α for treating MPNST is disclosed. In yet another embodiment, present disclosure is directed to a combination of an APE1/Ref-1 inhibitor and a survivin inhibitor (e.g., YM155) for treating MPNST.

Leukemia

Few studies have focused on the role of Ref-1 in leukemias. To date the only published studies have concentrated on the role of Ref-1 in acute promyelocytic leukemia (APL) and its relationship to all-trans retinoic acid (ATRA, or RA) and retinoic acid receptor (RAR) transcription factors. RAR alpha binds to its DNA binding site (RARE) in a redox-dependent fashion. Studies demonstrate that RAR-RARE binding is blocked through Ref-1 redox inhibition using APX3330. Additionally, the addition of APX3330 to ATRA increases apoptosis and cellular differentiation of APL cells by three-fold. These results indicate the potential of using APX3330 in combination treatment with ATRA. This could accomplish two things; first, a new treatment combination for leukemias where ATRA is used, and second, a reduction in the ATRA dose while maintaining similar or increased therapeutic effect. This latter point is important, as one should be able to avoid the toxicity of RA differentiation syndrome by being able to increase RA-induced promyeloblast differentiation, but with lower amounts of RA. Reducing the dose of RA has important clinical implications and could help to eliminate some of the undesirable side effects of this therapy, such as differentiation syndrome.

Recent studies show Ref-1 is highly expressed in T-cell acute lymphoblastic leukemia (T-ALL). Blockade of Ref-1 by the redox-specific inhibitor APX3330 potently inhibits viability of leukemia T-cells, including primary cells, relapsed and chemotherapy-resistant cells, and cells from a mouse model of T-ALL. Ref-1 redox inhibition promotes leukemia cell apoptosis, which is associated with downregulation of pro-survival genes. These data demonstrate a role for Ref-1 in the regulation of multiple transcriptional programs in T-cell ALL, and suggest that disruption of Ref-1 redox function represents an efficient strategy to target leukemia T-cells, including high-risk, relapsed leukemias.

Finally, investigators studying conversion of pre-leukemic acute myeloid leukemia (AML) cells with TET2 mutations to full-blown AML have identified a significant role of Ref-1 in this process. Tet2-deficient stem cells demonstrate resistance to inflammatory challenge as revealed by a higher repopulating and engraftment potential in both primary and secondary recipients compared to wildtype controls, which, when stressed, show a remarkable decline in overall engraftment. This process invokes the NF-κB pathway, which Ref-1 regulates. APX3330 blocks NF-κB function, which decreases inflammation and reverses the progression from pre-AML to frank AML in mice bearing AML-associated epigenetic mutations often observed in healthy individuals with clonal hematopoiesis. These data suggest that APX3330 treatment could clinically benefit normal individuals carrying TET2 mutations that show signs of clonal hematopoiesis, as well as patients with TET2 mutations who have acute myeloid leukemia, myeloproliferative disease and myelodysplastic syndrome.

In summary, while studies on Ref-1 in leukemia trail behind research performed on solid tumors, recent investigations are uncovering a critical role of Ref-1 redox signaling and effectiveness of APX3330 in those leukemias investigated.

In one embodiment, the present disclosure is directed to a combination of an APE1/Ref-1 inhibitor (e.g., APX3330, APX 2009 and APX2014) and a NF-κB inhibitor (e.g., napabucasin) for treating T-ALL. In some particular embodiments, the patient to be treated is carrying TET2 mutations that show signs of clonal hematopoiesis.

In some embodiments, the combination of an APE1/Ref-1 inhibitor (e.g., APX3330, APX 2009 and APX2014) and a NF-κB inhibitor can be used for treating patients with TET2 mutations who also have acute myeloid leukemia, myeloproliferative disease or myelodysplastic syndrome.

Retinal Diseases

Figure 4:
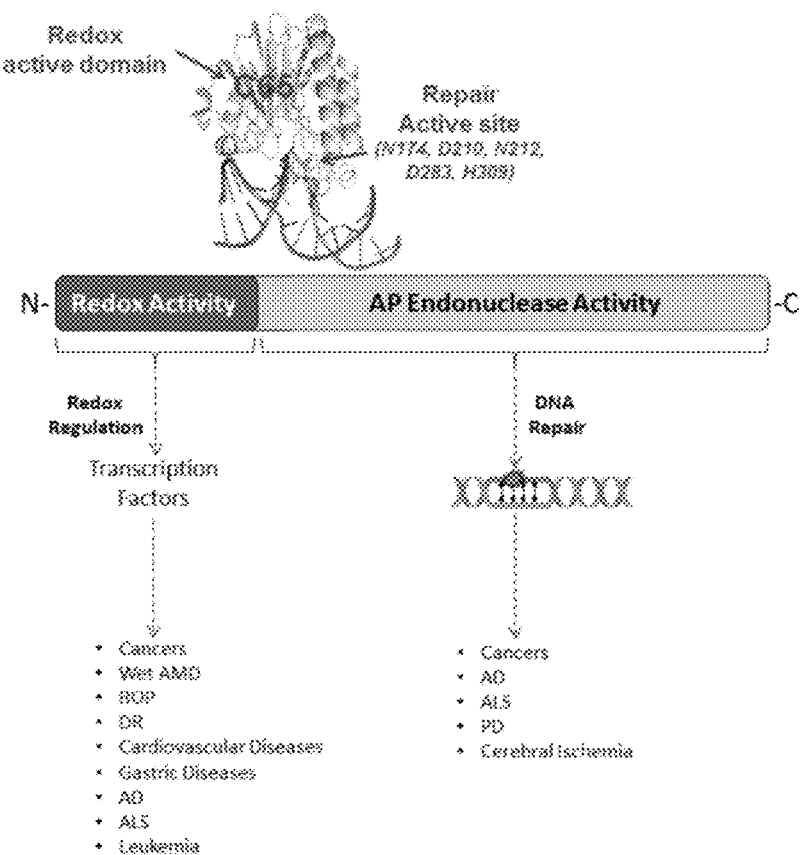
FIG. 4 depicts the effects of APE1/Ref-1 in human diseases due to its multi-functional nature, APE1/Ref-1 impacts a wide range of human diseases. Altered expression of Ref-1 affects its regulation of multiple transcriptional factors, leading to various cancers, retinal, cardiovascular, gastric and neurodegenerative diseases. Similarly, modified APE1 DNA repair function affects progression of different cancers and neurodegenerative diseases.

Increased levels of Ref-1 are not limited to cancers (FIG. 4). Elevated Ref-1 has been implicated in age-related cataracts. Ref-1 levels are higher in the lens epithelium cells of patients versus controls, and Ref-1 levels decrease as the opaque degree worsens.

Ref-1 is highly expressed in developing murine retinas, as well as retinal pigment epithelium (RPE) cells, retinal pericytes, choroid endothelial cells (CECs) and retinal vascular endothelial cells (RVECs). Using the Ref-1 inhibitor APX3330 shows that Ref-1 redox activity is required for RVEC proliferation, migration and angiogenesis in vitro. Similarly, APX3330 treatment reduced proliferation, migration and angiogenesis in CECs in primate cells in vitro and had an additive effect when combined with bevacizumab. RPEs stressed using oxidized low-density lipoproteins (oxLDLs) were rescued from proliferation decline and senescence by APX.

In adult human RPE cell lines, APX3330 reduced the transcriptional activity of NF-κB, a key factor associated with inflammation in angiogenesis. It also blocked activation of HIF-1a and reduced the expression of its downstream target VEGF. VEGF expression via NF-κB and HIF-1α is primarily responsible for choroidal neovascularization (CNV), a characteristic of neovascular Age-related Macular Degeneration (AMD), also known as wet AMD.

When very low density lipoprotein receptor (VLDLR) knockout mice are treated with a single intravitreal injection of APX, CNV is reduced. APX3330 also shows anti-angiogenic effects in mice with laser-induced CNV.

Angiogenesis is also a prime component of other retinal diseases, including Retinopathy of Prematurity (ROP) and Diabetic Retinopathy (DR). Ref-1 's redox ability to modulate angiogenesis makes it worth investigating in those diseases. Interestingly, both HIF-1α and VEGF are increased in ROP and DR. Retinal neovascularization, a marker of ROP and DR, is markedly reduced in mice with ischemic retinopathy when treated with siRNA targeting HIF-1α or VEGF.

However, the difficulties in creating druggable targets for HIF-1α have been discussed. Additionally, ocular anti- VEGF therapies are not always effective and may lead to unwanted side effects. Inhibiting the redox activity of Ref-1 may prove to be a more efficacious standalone or adjunctive treatment that can modulate HIF-1α and VEGF in retinal diseases like wet AMD, ROP and DR.

Other Diseases

Ref-1 has also been shown to play a role in several other diseases. Ref-1's involvement in cardiovascular disease and regulation of blood pressure is illustrated by aortic coarctation-induced hypersensitive rat models showing increased Ref-1 expression levels. Furthermore, heterozygous Ref-1+/− mice exhibit hypertension and diminished endothelium-dependent vasorelaxation. Ref-1 is part of the SET complex of proteins that are involved in HIV pathogenesis by inhibiting suicidal autointegration. Consequently, knocking down Ref-1 inhibits HIV infection.

Ref-1 is also implicated in gastric cellular response to *Helicobacter pylori* (*H. pylori*) infection. Ref-1 expression levels were elevated following *H. pylori* infection in human gastric epithelial cells. *H. pylori* induced ROS and downstream activated genes were higher in Ref-1 deficient cells compared to control, with Ref-1 overexpression reversing these effects. Additionally, Ref-1 siRNA knockdown inhibited *H. pylori* and TNF-α-induced AP-1 and NF-κB DNA binding, as well as IL-8 mRNA expression and protein secretion in gastric epithelial cells. Collectively, that implicates Ref-1 in gastric inflammatory disorders as well as sepsis.

Another area of particular interest is neurodegenerative disease (ND). NDs such as Alzheimer's disease (AD), Parkinson's disease (PD), amyotrophic lateral sclerosis (ALS) and cerebral ischemia are all affected by APE1/Ref-1 dysfunction.

Ref-1 protein levels are elevated in nuclear extracts from the midfrontal cortex and cerebral cortex of AD patients compared to controls, with Ref-1 redox activity being seen as a compensatory mechanism for increased oxidative stress. However, reduced APE1 endonuclease activity is seen in peripheral blood mononuclear cells of AD patients, suggesting impaired Base Excision Repair (BER). This highlights the different roles that Ref-1 can have within a particular disease. Similarly, Ref-1 levels are elevated in the central nervous system of patients with ALS, a disease exhibiting elevated oxidative stress and DNA damage. In PD, loss of Ref-1 function via gene variants suggests it is a risk factor, contributing to increased oxidative stress that leads to loss of dorsal root ganglion (DRG) neurons. Ref-1 is upregulated in cells treated with rotenone and MPP$^+$ (1-methyl-4-phenylpyridinium), both of which are used to simulate a PD model. Ref-1 upregulation protects against neuronal death in these cells.

After cerebral ischemia, upregulation of Ref-1 protects hippocampal neurons from cell loss and DNA fragmentation. Conversely, transgenic rats with DNA repair-compromised Ref-1 are not protected from ischemic injury. Ref-1 conditional knockout mice exhibit larger infract volume and diminished recovery of spatial and cognitive function following cerebral ischemia.

These findings highlight the wide range of diseases affected by Ref-1, indicating that it is a promising target for treating and managing numerous diseases.

Combination Therapies

Further, these findings support the use of Ref-1 specific inhibitors such as APX3330 and APX2009 in combination therapies with these second therapeutic agents. Specifically APX3330 and/or APX2009 can be combined with inhibitors of STAT3, HIF1α, CA9, VEGF, NFκB, JAK2, Bcl-2, PTEN, WNT/β-catenin, Endostatin, 5-fluorouracil (5-FU), and a photodynamic therapy (PDT), and the like, and combinations thereof. More particularly, exemplary combinations include APX3330 and/or APX2009 with one or more of a second therapeutic agent selected from those in Tables 2 & 3.

TABLE 2

| | |
|---|---|
| Bortezomib | Ispinesib Mesylate |
| SN-38 | Topotecan |
| Paclitaxel | Bryostatin 1 |
| Trametinib | LAQ824 |
| Vinblastine | BEZ235 |
| Panobinostat | Methotrexate |
| Temsirolimus | FK866 |
| Afatinib | Tozasertib |
| Irinotecan | GSK2126458 |

Suitable dosages of the Ref-1 inhibitor (e.g., APX3330) and second therapeutic agent for use in the combination therapies of the present disclosure will depend upon a number of factors including, for example, age and weight of an individual, at least one precise cancer/disease requiring treatment, severity of a disease, specific Ref-1 inhibitor and/or second therapeutic agent to be combined, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

Additionally, in some suitable embodiments, the combination therapies can include pharmaceutically acceptable carriers, for example, excipients, vehicles, diluents, and combinations thereof. For example, where the combination therapies are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compounds (i.e., APX3330 and second therapeutic agent) may be mixed with any conventional additive, such as an excipient, a binder, a disintegrating agent, a lubricant, a corrigent, a solubilizing agent, a suspension aid, an emulsifying agent, a coating agent, or combinations thereof.

The combination therapies including the Ref-1 inhibitor and second therapeutic agent and/or pharmaceutical carriers of the present disclosure can be administered to a subset of individuals in need. In one embodiment, as used herein, an "individual in need" refers to an individual at risk for or having cancer, and in particular, prostate cancer, breast cancer, ovarian cancer, cervical cancer, osteosarcoma, colon cancer, bladder cancer, pancreatic cancer, gliomas, and the like as listed in Table 1. In other embodiments, an "individual in need" refers to an individual at risk for or having a retinal disease (e.g., choroidal neovascularization (CNV), age-related macular degeneration (AMD), retinopathy of prematurity (ROP), diabetic retinopathy (DR)). In yet other embodiments, an "individual in need" refers to an individual at risk for or having cardiovascular disease, bacterial infection, gastric inflammatory disorders, neurodegenerative diseases (e.g., Alzheimer's disease (AD), Parkinson's disease (PD), amyotrophic lateral sclerosis (ALS), cerebral ischemia). Additionally, an "individual in need" is also used herein to refer to an individual at risk for or diagnosed by a medical professional as having any one of these diseases and/or disorders. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Identification of Additional Pathways for Combinatorial Drug Approach

A proposed factor in the limited success of molecular therapies has been the heterogeneity found in tumor samples, especially aggressive ones such as pancreatic tumors or glioblastomas. This underscores the need for strategies that target nodal proteins capable of affecting multiple pathways, such as Ref-1. The evaluation of novel targets including Ref-1 and rationally designed combination therapy, including correlative biomarker research, is critical in cancer because therapeutic options for some cancer patients remain limited.

To elucidate increased lethal pairs of chemotherapeutic agents, two general approaches are utilized. They include rational, hypothesis-driven combinations based on the mechanism of action of the compounds as well as application of "big data" that reveal specific gene expression profiles or proteomic signatures that would render cancer cells vulnerable when used in combination. Combination therapy that involves Ref-1 modulation that results in increased lethality is focused on herein.

Many studies have investigated the potentiation of DNA-damaging agents in combination with Ref-1 inhibition. Presumably the predominant mechanism of potentiation in these studies was due to blockade of Ref-1's DNA repair function, which led to cellular inability to respond to the DNA damage caused by the chemotherapeutic agent. Hereinafter, published studies of inhibition of Ref-1 redox function or treatment with Ref-1 siRNA (Table 3) are discussed.

Pairing Therapeutic Agents with Ref-1 Based on its Known Functions in Cancer Cells First, a hypothesis-driven approach is used to test chemotherapeutic agents in combination with Ref-1 inhibitors to screen for increased lethality. This approach involves simultaneously impinging upon Ref-1 signaling in conjunction with another key pathway that interacts with or depends upon Ref-1 function for tumor cell survival. The combination of the two should create an increased lethality, dramatically enhancing cell death compared to their effect when administered alone.

TABLE 3

| Molecular target/therapeutic agent paired with Ref-1 | Pathways affected | Model System |
| --- | --- | --- |
| Doxorubicin | Hypoxia/ABC transporter expression | Colon Cancer |

TABLE 3-continued

| Molecular target/therapeutic agent paired with Ref-1 | Pathways affected | Model System |
| --- | --- | --- |
| STAT3 | Viability/Migration | PDAC |
| Avastin | Angiogenesis | Retinopathy |
| DNA damage (cisplatin)/Bcl-2 inhibitor | Proliferation/Migration/Apoptosis | NSCLC |
| Platinating agents (cisplatin/oxaliplatin/carboplatin) | Attenuation of vasodilatation of sensory neurons | Chemotherapy-induced neuropathy |
| CA9 | Hypoxia | PDAC |
| WNT/β-catenin | ROS/Proliferation | PDAC |
| Endostatin | Angiogenesis | Osteosarcoma |
| 5-FU | Proliferation/Tumor growth | Colon Cancer |
| CPI-613 | Energy production pathways; mitochondrial metabolism pathways | Colon and Pancreatic Cancer |
| Notch3 (γ-secretase inhibitors, DLL4-inhibiting antibodies) | Notch signaling pathway - cell survival, proliferation, differentiation, development, homeostasis | Pancreatic Cancer |
| Retinoic Acid | Differentiation | Promyelocytic leukemia |
| Photodynamic Therapy (PDT) | Proliferation/TFAM (Transcription Factor A, mitochondria) binding | NSCLC |

Figure 3A:
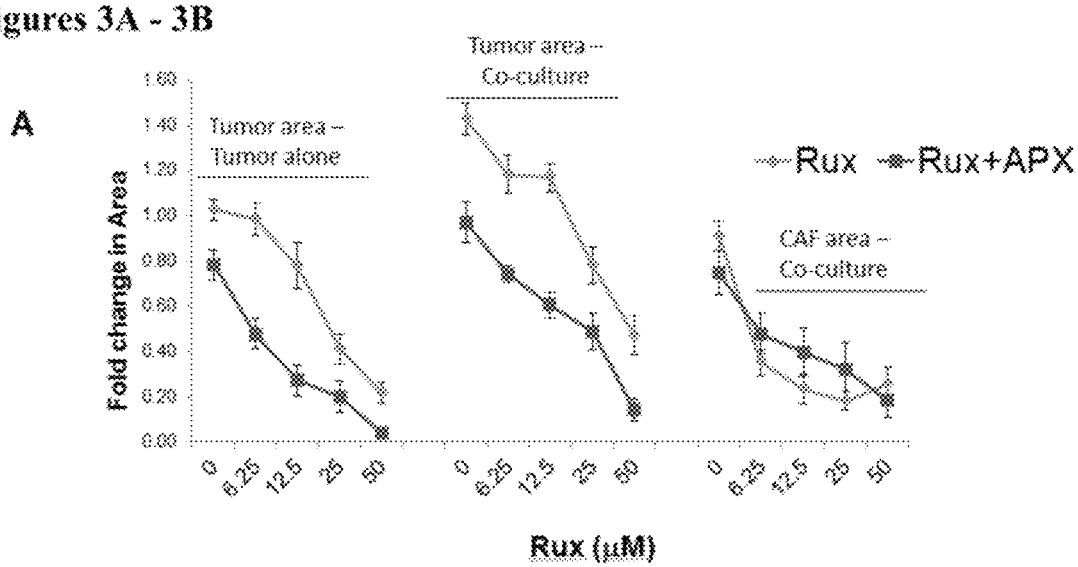
FIGS. 3A & 3B depict that dual-targeting of Ref-1 and Jak/STAT signaling inhibits PDAC tumor growth in a 3D co-culture model.
Figure 3B:
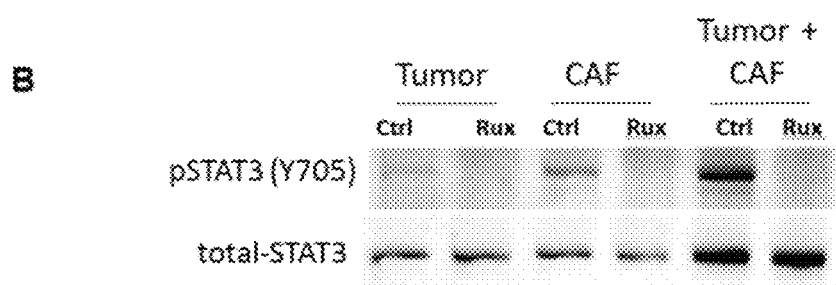

Using this approach, it was discovered that impinging upon STAT3 signaling in combination with Ref-1 signaling dramatically affects the viability and migratory ability of pancreatic cancer cell lines (FIG. 3).

Several studies of different cancers support the notion that combination therapy involving inhibition of Ref-1 in tumor-promoting processes such as hypoxia or angiogenesis is efficacious. In an osteosarcoma model characterized by hypoxia and angiogenesis, inhibition of Ref-1 in combination with endostatin demonstrates in vivo efficacy with decreases in VEGF expression and microvessel density.

Figure 2:
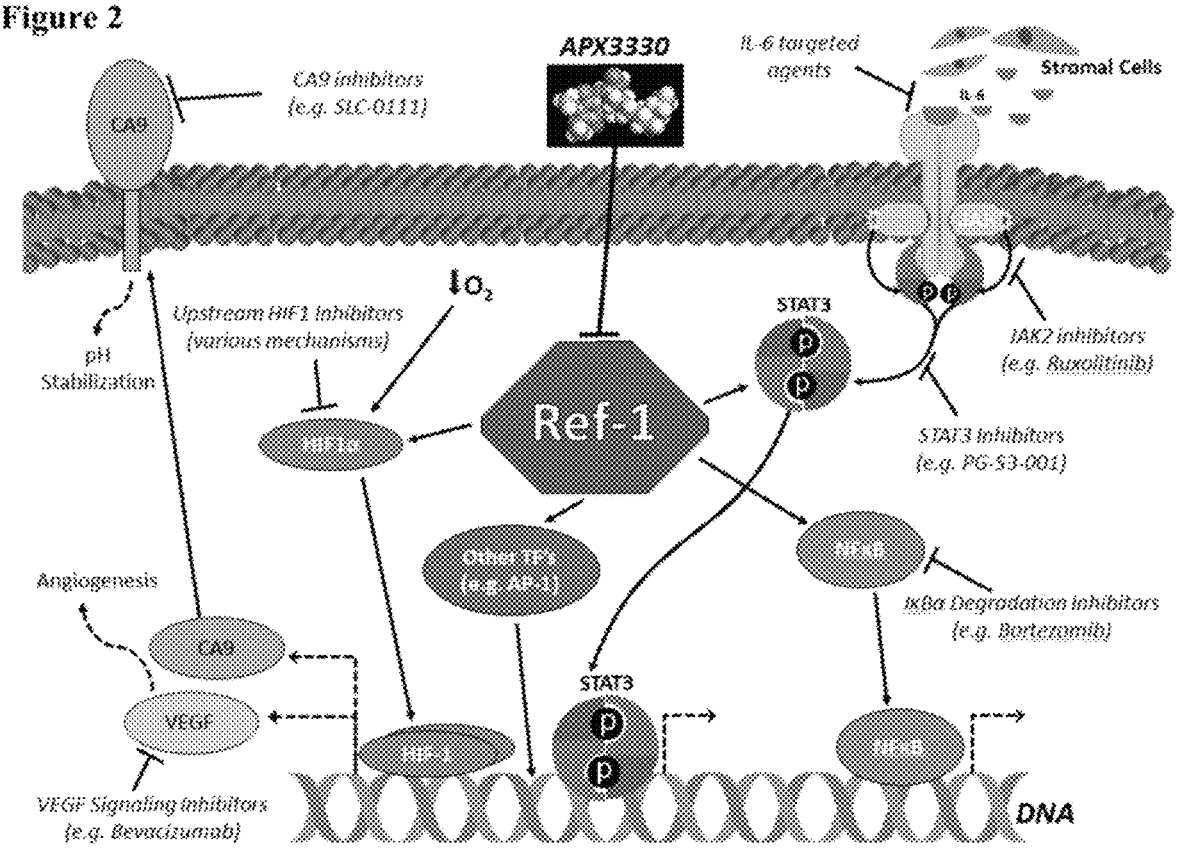
FIG. 2 depicts Ref-1 signaling as a node in tumor cells and potential inhibitors in related pathways. Ref-1 redox signaling promotes the transactivation of transcription factors such as STAT3, HIF-1α, and NF-κB. Inhibiting Ref-1 with APX3330 decreases the expression of downstream genes, leading to tumor cell growth arrest and/or death. Additionally, other methods for inhibiting the signaling pathways affected by Ref-1, as well as the enzymes that are upregulated by these pathways, have been shown to enhance the cytotoxic and cytostatic effects of Ref-1 inhibition.

Another increased lethal pair involving Ref-1 and hypoxia is the combination of Ref-1 inhibition with inhibition of the HIF-1α target CA9. Using pancreatic 3D co-culture models, tumor spheroid area is reduced after dual targeting with Ref-1 and CA9 (FIG. 2). The mechanism of enhancement is believed to be due to an increase in pH and blockade of the tumor's ability to adapt to hypoxic conditions perpetuated through simultaneous CA9 and Ref-1 blockade.

Finally, studies comparing doxorubicin-sensitive vs doxorubicin-resistant colon cancer cells demonstrate that hypoxia enhances the expression of Pgp (P-glycoprotein) and BCRP (breast cancer resistance protein)—and that the addition of APX3330 to doxorubicin under hypoxic conditions can attenuate HIF activity significantly, blocking the upregulation of Pgp and BCRP. This decrease in Pgp and BCRP expression may play a role in the observed increase in doxorubicin accumulation, especially in the parental cells. The results suggest that, when blockade of Ref-1's redox function blockades HIF signaling, colon cancer cells' response to doxorubicin may be enhanced.

A recent study sought to sensitize NSCLC cell lines to cisplatin by sequential use of AT-101 (gossypol) with cisplatin. AT-101 exerts its anti-tumor effects in many ways: it is a BH3-mimetic and also has been shown to inhibit Ref-1's DNA repair and redox activities. Blockade of the anti-apoptotic proteins Bcl-2 and Bcl-XL through Ref-1's redox inhibition of STAT3 activity contributes to the enhanced cell killing and tumor growth seen in this combination. Furthermore, in NSCLC cell line A549, siRNA inhibition of APE1 expression significantly sensitizes A549 cells to cisplatin and increased cell apoptosis. Both of these studies point to Ref-1 function as critical in the cells' response to cisplatin, especially in apoptosis signaling through STAT3.

In contrast, a recent study in breast cancer cell lines that were exposed to cisplatin in combination with inhibitors of either APE1 repair or Ref-1 redox activity, cisplatin resistance increased. The authors conjecture that a concurrent downregulation of mismatch repair proteins (MSH2, MSH6, MLH1, and ERCC1) may explain why those results differ from the other studies that demonstrate a greater response to cisplatin when Ref-1 is inhibited concurrently. In the pursuit of personalized medicine, these preclinical studies demonstrate the importance of elucidating cell-specific signaling following chemotherapy as well as the crosstalk between DNA repair pathways that occurs following DNA damaging agents. These factors will need to be considered as new treatment combinations are proposed, such as considering the addition of a Ref-1 inhibitor to a cisplatin regimen.

Finally, both Ref-1 inhibition via APX3330 and siRNA knockdown of Ref-1 upregulates β-catenin in pancreatic cancer cells. When the WNT/β-catenin inhibitor IWR-1 was paired with APX, enhanced cytotoxicity occurred.

These studies show how seemingly "separate tracks" of cancer survival pathways can intersect, how those intersections involve Ref-1, and the exciting therapeutic possibilities that arise from those intersections.

Mining Big Data to Predict Combination Therapy Involving Ref-1

A second option for uncovering new treatment options is to mine publicly available data sets such as TCGA (The Cancer Genome Atlas) and CCLE (Cancer Cell Line Encyclopedia) to elucidate [in silico] effective combination treatments to utilize in cancer treatment settings. The goal is to accelerate the selection of likely increased lethal targets, particularly for aggressive cancers that have few treatment options.

For example, historically in pancreatic cancer, new targeted agents would be paired with the standard-of-care agent, gemcitabine. But, adding selective inhibitors of multiple cancer-related pathways to gemcitabine either did not extend survival significantly or, although statistically significant, did not extend the 5-year survival rate. In today's age of omics, "big data" can be used to predict increased lethality and effective drug combinations rather than a shotgun approach.

A study combining transcriptional and proteomic profiling following Ref-1 knockdown in HeLa cells reveals several pathways that are differentially expressed following Ref-1 modulation. These pathways include DNA damage, mitochondrial function, and microtubule stabilization. The downregulation of DNA repair proteins following Ref-1 knockdown is another confirmation that the addition of a Ref-1 inhibitor to a DNA-damaging agent is deleterious to cancer cells.

The aforementioned study also demonstrates a downregulation in mitochondrial function. Mitochondria are emerging as important indicators of cellular disease or health following Ref-1 modulation, therefore drugs that target anti-apoptotic mechanisms may be efficacious when combined with Ref-1 inhibition. Such drugs might include Bcl-2 inhibitors or YM-155 (a survivin inhibitor). Finally, the proteomic study indicates another area in which Ref-1 inhibition may be useful as an increased lethality. Lack of Ref-1 expression affects microtubule stabilization proteins such as actin, impeding proper organization of the fibers. Several commonly used chemotherapeutic agents disrupt microtubule dynamics, including docetaxel, paclitaxel, and vinblastine. Therefore, those agents show promise for being able to be paired with Ref-1 inhibition.

Ref-1 DNA Repair and CIPN; Indirect Linking Through Altering Redox Function

Chemotherapy-induced peripheral neuropathy (CIPN) is one of the most prevalent dose-limiting toxicities of anticancer therapy. Up to 90% of cancer patients experience chemotherapy-induced peripheral neuropathy (CIPN) at some point during or after anticancer treatment. Indeed, anticancer drugs used for the six most common malignancies pose a substantial risk for CIPN. These drugs include, but are not limited to platinum agents, taxanes, vinca alkaloids, proteasome inhibitors, immunomodulators and even new, targeted therapeutic agents. There are currently no approved treatments to prevent or treat CIPN, thus the neurotoxicity can be dose-limiting for some patients. Platinum drugs, particularly cisplatin and oxaliplatin, are an important component of numerous standard-of-care treatment (SOC) regimens for pediatric and adult cancers; for example, oxaliplatin is a part of the FOLFIRINOX and FOLFOX protocols.

CIPN can persist after treatment is completed. Up to 40% of cancer patients continue to struggle with CIPN five years after treatment ends—and 10% remain symptomatic after more than 20 years. Thus, CIPN directly affects cancer survivorship, quality of life, and may limit future treatment options if cancer recurs.

Figure 5:
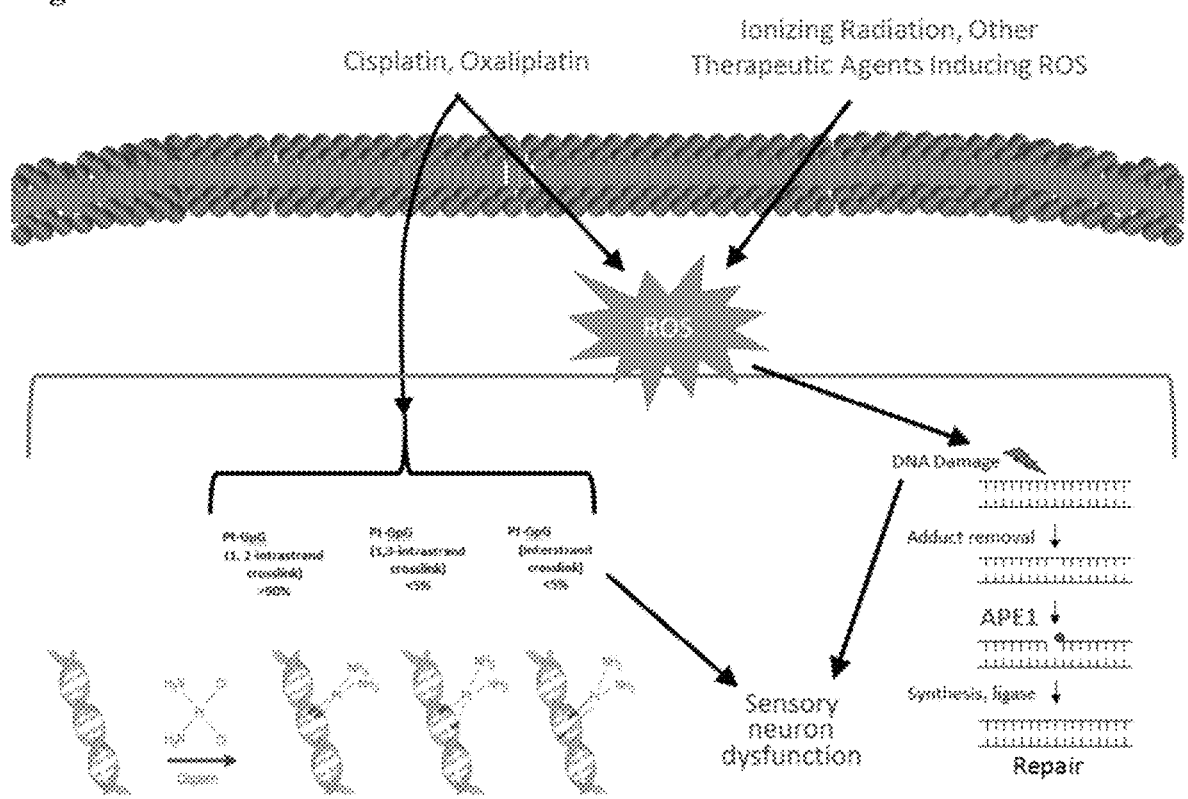
FIG. 5 depicts that anticancer treatments inducing oxidative DNA damage alters sensory neuronal function. These agents include cisplatin, oxaliplatin, ionizing radiation as well as other drugs. ROS, reactive oxygen species; Pt, platinum adduct; APE1, apurinic/apyrimidinic endonuclease.

In previous studies using an experimental model of cultured sensory neurons, a causal relationship was established between CIPN and DNA damage and repair. It was demonstrated that reducing the activity of the DNA base excision repair (BER) pathway by reducing expression of APE1 increased the neurotoxicity produced by anticancer treatment, whereas, augmenting the activity of APE1 lessened the neurotoxicity. Additionally, it was demonstrated that APE1's DNA repair function—not the redox signaling function—is crucial for sensory neuron survival and function. It was further demonstrated that the small-molecule redox inhibitor APX3330 protects sensory neurons from oxidative DNA damage caused by ionizing radiation (IR), cisplatin, and oxaliplatin (FIG. 5).

Figure 6A:
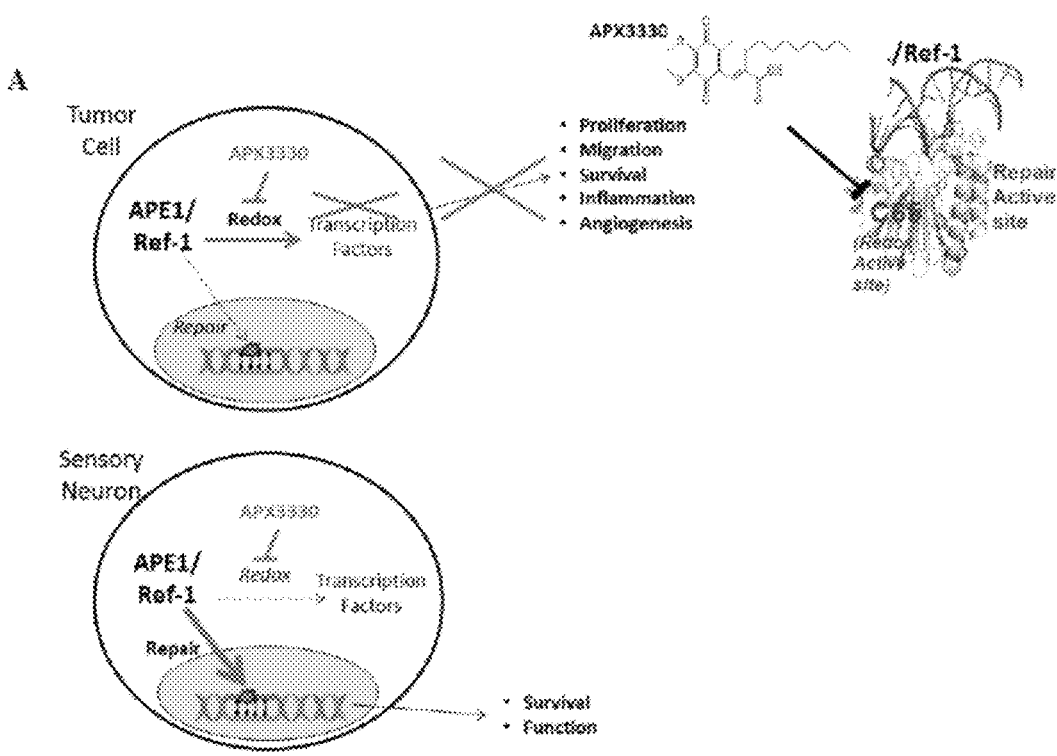
Figure 7:
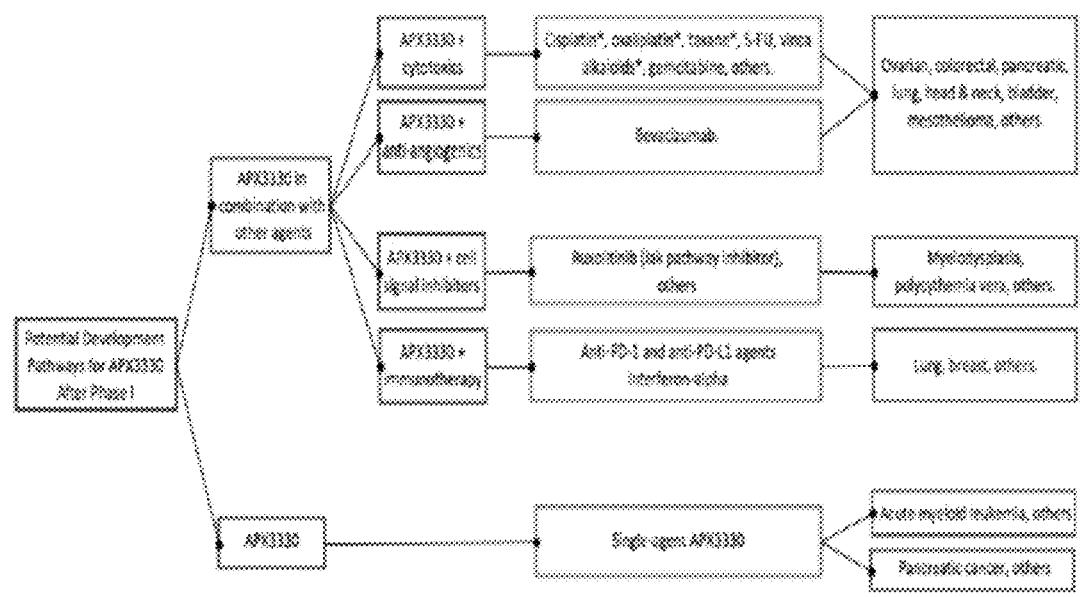
FIG. 7 depicts that APX3330 has broad potential in a variety of cancers. Supportive pre-clinical data exists for APX3330 in combination with each drug listed in the diagram (second column of boxes from the right) and for each indication (boxes at far right). *In addition to anti-tumor activity, APX3330 provides neuroprotection when administered with agents causing oxidative damage to neurons.

This begs the question: how does a Ref-1 redox-specific inhibitor affect DNA repair activity? Although APX3330 is a targeted inhibitor of APE1/Ref-1's redox function, it appears that, in the setting of sensory neurons, it can also enhance the protein's DNA repair (AP endonuclease) activity (FIG. 6). Although this seems counterintuitive, APX3330 causes the protein to unfold over time. This unfolding primarily alters the amino end of APE1/Ref-1, affecting its interactions with downstream transcription factor targets by perturbing the equilibrium of the protein's folded/unfolded states and facilitating repair activity. This disengagement of APE1 from its Ref-1 redox activity could enhance APE1 repair endonuclease activity. When isolated sensory neurons are exposed to APX3330, a concentration-dependent increase in Ref-1 endonuclease activity occurs, which is not observed in tumor cells. As discussed herein, it was found that APX3330 protected sensory neurons from DNA damage and reactive oxygen species (ROS) production induced by agents such as ionizing IR, cisplatin and oxaliplatin.

A critical property of any putative therapeutic for neurotoxicity is that it will not compromise the anticancer function of the treatment(s) administered. Importantly, the enhancement of DNA repair activity by APX3330 was not observed in mitotic cells. It was shown that APX3330 negatively affects the growth and/or survival of tumor cell lines, patient-derived cell lines, and tumors in animal models. Therefore, it is possible that APX3330 could protect postmitotic cells without altering the effects of anticancer drugs on tumor cells (FIG. 6). Additionally, APX3330 does not affect cisplatin or oxaliplatin's tumor-killing efficacy in vivo, yet it protects DRG neurons from oxidative DNA damage. If further translational research further bears out these findings, APX3330 could be offered as a neuroprotective mechanism in humans, facilitating BER repair of oxidative DNA damage and protecting sensory neurons. In healthy cells, it appears that the DNA repair function—not the redox function of APE1/Ref-1—is necessary for sensory neuronal survival/function. That is opposite from tumor cells. Collectively, these data support the notion that APX3330 can be neuroprotective against cancer therapy without compromising treatment.

Example 1

While a number of studies have investigated genes regulated by APE1, and specifically its redox signaling function, it has proven difficult to compile a comprehensive list of genes regulated by APE1 as it is essential for cell viability. Particularly, APE1 knockout in mice results in embryonic lethality, post-implantation, between days E5-E9. As such, it has not historically been possible to generate stable APE1 knockout cell lines.

Approaches to circumvent this dilemma have utilized conditional knockouts and siRNA knockdowns. While APE1 knockdowns via siRNA are useful, this approach produces a heterogeneous population, resulting in cells with differing amounts of the APE1 protein. Additionally, siRNA knockdowns are transient with APE1 expression recovering over time. Consequently, there may be a limit to the amount of information gained using APE1 siRNA in a mixed population.

In order to address this problem and more accurately detect changes to the potential numerous effectors regulated by APE1, in this Example single-cell RNA Sequencing (scRNA-seq) is utilized to identify new pathways not previously linked to APE1.

Methods

Cell Culture

Pa03C, Pa02C, Panc10.05 and Panc198 (Pa20C) were obtained from Dr. Anirban Maitra at The Johns Hopkins University. All cells were maintained at 37° C. in 5% $CO_2$ and grown in DMEM (Invitrogen; Carlsbad, CA) with 10% Serum (Hyclone; Logan, UT). Cell line identity was confirmed by DNA fingerprint analysis (IDEXX BioResearch, Columbia, MO) for species and baseline short-tandem repeat analysis testing. All cell lines were 100% human and a nine-marker short tandem repeat analysis is on file. They were also confirmed to be *mycoplasma* free.

Transfection with APE1 and Scrambled siRNA

The siRNAs used were Scrambled (SCR) (5' CCAUGAGGUCAGCAUGGUCUG 3', 5' GAC-CAUGCUGACCUCAUGGAA 3') (SEQ ID NO:1) and siAPE1 (5' GUCUGGUACGACUGGAGUACC 3' (SEQ ID NO:2), 5' UACUCCAGUCGUACCAGACCU 3') (SEQ ID NO:3). All siRNA transfections were performed by plating $1 \times 10^5$ cells per well of a 6-well plate and allowing the cells to attach overnight. The next day, Lipofectamine RNAiMAX reagent (Invitrogen, Carlsbad, CA) was used to transfect in the APE1 and SCR siRNA at concentrations between 10 and 50 nM following the manufacturer's indicated protocol. Opti-MEM, siRNA, and Lipofectamine was left on the cells for 16 hours and then regular DMEM media with 10% Serum was added. Cells were assayed for RNA and protein expression 3 days following transfection.

Western Blot Analysis

For whole cell lysates, cells were harvested, lysed in RIPA buffer (Santa Cruz Biotechnology, Santa Cruz, CA), and protein was quantified and electrophoresed. Immunoblotting was performed using the following antibodies: APE1 (Novus Biologicals, Littleton, CO) and Vinculin (Sigma, St. Louis, MO). For qRT-PCR experiments, APE1 expression was at least 80% decreased compared to scrambled control in order to be considered for further analysis.

Single Cell RNA-Sequencing

Three days post-transfection, SCR/siAPE1 cells were collected and loaded into 96-well microfluidic Cl Fluidigm array (Fluidigm, South San Francisco, CA, USA). All chambers were visually assessed and any chamber containing dead or multiple cells was excluded. The SMARTer system (Clontech, Mountain View, CA) was used to generate cDNA from captured single cells. The dscDNA quantity and quality was assessed using an Agilent Bioanalyzer (Agilent Technologies, Santa Clara, CA, USA) with the High Sensitivity DNA Chip. A total of 48 SCR and 48 siAPE1 cells were chosen for sequencing. The Purdue Genomics Facility prepared libraries using a Nextera kit (Illumina, San Diego, CA). Unstranded 2×100 bp reads were sequenced using the HiSeq2500 on rapid run mode in 1 lane. RNA-seq data are available at the Gene Expression Omnibus (GEO) through accession number pending.

Bioinformatics and Statistical Analyses

Read quality was observed using FastQC v. 0.11.2 and after quality trimming was performed using FastX-Toolkit v. 0.0.13.2. A FastX trimscore of 30 and a trim length of 50 were used. Tophat2 was used to align trimmed reads to the human genome (ENSEMBL version GrCh38.p7). One mismatch was allowed. The htseq-count script in HTSeq v.0.6.1 was run to count the number of reads mapping to each gene. HTSeq used Biopython v.2.7.3 in the analysis. In order to determine which genes were differentially expressed the R package BPSC was used, which is specifically designed to analyze single-cell RNA-seq data. Ingenuity Pathway Analysis was utilized in performing network analyses (IPA, QIAGEN Redwood City, www.qiagen.com/ingenuity). An upstream regulator analysis, canonical pathway analysis, mechanistic networks analysis, causal network analysis, and downstream effects analysis were performed using IPA (results were deemed significant for p-values <0.05). Algorithms and details of each type of network analysis are presented in Kramer, A., et al., *Causal analysis approaches in Ingenuity Pathway Analysis*. Bioinformatics, 2014. 30(4): pp. 523-30.

qRT-PCR Reactions qRT-PCR was used to measure the mRNA expression levels of the various genes identified from the scRNA-seq analysis. Following transfection, total RNA was extracted from cells using the Qiagen RNeasy Mini kit (Qiagen, Valencia, CA) according to the manufacturer's instructions. First-strand cDNA was obtained from RNA using random hexamers and MultiScribe reverse transcriptase (Applied Biosystems, Foster City, CA). Quantitative PCR was performed using SYBR Green Real Time PCR master mix (Applied Biosystems, Foster City, CA) in a CFX96 Real Time detection system (Bio-Rad, Hercules, CA). The relative quantitative mRNA level was determined using the comparative Ct method using ribosomal protein L6 (RPL6) (Pa03C) or Actin (Panc10.05, Panc 198, Pa02C) as the reference gene. The primers used for qRT-PCR are detailed in Table 4. Experiments were performed in at least triplicate for each sample. Statistical analysis performed using the $2^{-\Delta\Delta C_T}$ method and analysis of covariance (ANCOVA) models.

TABLE 4

Primers used for qRT-PCR.

| Gene | Primer | Sequence | SEQ ID NO. |
|---|---|---|---|
| Actin | Forward | CACCATTGGCAATGAGCGGTTC | 4 |
|  | Reverse | AGGTCTTTGCGGATGTCCACGT | 5 |
| RPL6 | Forward | ATTGCTTATAGACCGGAAGCCG | 6 |
|  | Reverse | AACTTTTTCACCCGCCATCTTG | 7 |
| BCRP/ABCG2 | Forward | GTTCTCAGCAGCTCTTCGGCTT | 8 |
|  | Reverse | TCCTCCAGACACACCACGGATA | 9 |
| CIRBP | Forward | GTCAGAGTGGTGGCTACAGTG | 10 |
|  | Reverse | GCCCTCGGAGTGTGACTTAC | 11 |
| COMMD7 | Forward | GAGCAGCGAATTGGAGAAAGTGG | 12 |
|  | Reverse | TCCATCTCGTGCAGGAAGCTGT | 13 |
| ISYNA1 | Forward | GCCAGACCAAAGTCAAGTCCGT | 14 |
|  | Reverse | CTTAGAGCGGAACTGCAATGGC | 15 |
| ITGA1 | Forward | CCGAAGAGGTACTTGTTGCAGC | 16 |
|  | Reverse | GGCTTCCGTGAATGCCTCCTTT | 17 |
| NOTCH3 | Forward | CCAGATGGCTTCACCCCGC | 18 |
|  | Reverse | TCAGTTGGCATTGGCTCCAG | 19 |
| PPIF | Forward | CGACTTCACCAACCACAATGGC | 20 |
|  | Reverse | GGTGTTAGGACCAGCATTAGCC | 21 |
| PRDX5 | Forward | TGATGCCTTTGTGACTGGCGAG | 22 |
|  | Reverse | CCAAAGATGGACACCAGCGAATC | 23 |
| RAB3D | Forward | ACGTGTTGTGCCTGCTGAGGAT | 24 |
|  | Reverse | CTTCTCGCAGATGACATCCACC | 25 |
| SIPA1 | Forward | GTGTCCACGATGCTGCCTTACA | 26 |
|  | Reverse | CTTGCTGCCAGGCTCCTGGAA | 27 |
| TAPBP | Forward | GAGCCTGTTCTCATCACCATGG | 28 |
|  | Reverse | GTAGGCAAAGCTCAAGTCCAGC | 29 |
| TNFAIP2 | Forward | TGCTCCAGAACCTGCATGAGGA | 30 |
|  | Reverse | AACTCAGGCAGCCTCGTGTCTA | 31 |

Results scRNA-Seq Analysis of APE1 Knockdown Cells

Figure 8A:
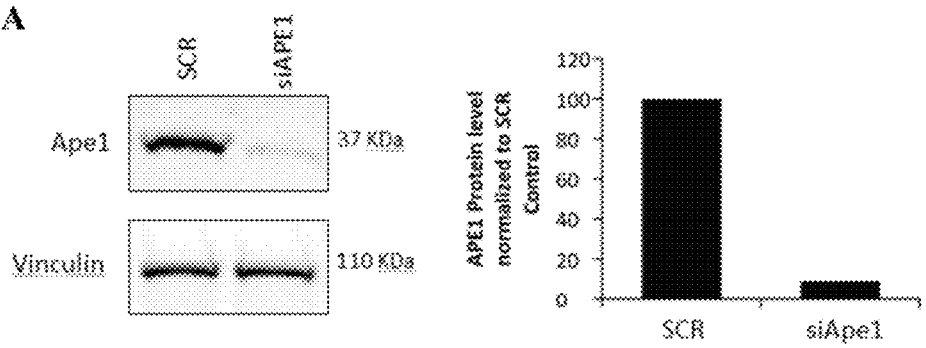
FIGS. 8A-8C depict APE1 expression and batch effects in cells following siRNA knockdown.

The siRNA knockdown of APE1 did not result in complete loss of the APE1 protein, as detected by Western blotting, with 10-20% APE1 protein expression observed in the siAPE1 samples compared to the scrambled controls (SCR) as shown by representative Western blot shown in FIG. 8A. 20 nM siRNA was used, as levels greater than this results in off-target effects and cell killing not related to APE1 functions. Therefore, in order to clearly identify changes in gene expression specifically related to the amount of APE1 protein within each individual cell, single-cell RNA-seq was performed on cells following APE1 siRNA knockdown.

Correcting for Batch Effects Using Cell Cycle-Annotated Genes

Due to sample preparation constraints, the siAPE1 and SCR cells were split across three batches, with one batch containing siAPE1 and two batches containing SCR cells (SCR 1 and SCR 2). Differences between cell batches were corrected by applying the scLVM R package. In conjunction with scLVM, the Biomart R package was used to obtain a list of cell cycle-annotated genes. Specifically, the Gene Ontology (GO) term GO:0007049 was used to identify 189 genes with the annotation name of "cell cycle". Of these 189 genes, only 102 coincided with the genes remaining in the analysis due to removal of genes exhibiting low expression across all cells (gene detection rate quality control filtering). A latent variable model was fit to account for cell cycle confounding, while also incorporating treatment and control covariates into the model. Using the fitted latent variable model, it was then possible to regress out the cell cycle confounding and compute a corrected dataset.

Figure 8B:
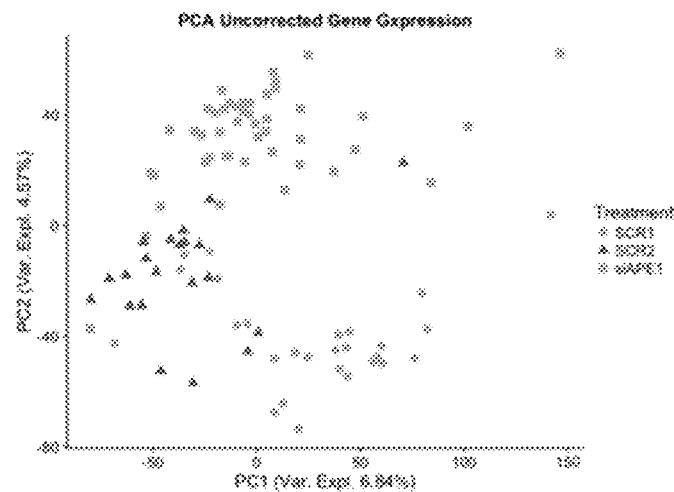

As an illustration, the plot in FIG. 8B demonstrates the two principal components before correcting for cell cycle and shows that the most influential source of variation (i.e., the x-axis representing 6.84% of the total variation) in the data corresponds to the axis along which SCR 1 and SCR 2 cells were separated. In contrast, the second most influential source of variation (i.e. the y-axis representing 4.57% of the total variation) corresponds to the axis along which siAPE1 and SCR cells were separated.

Figure 8C:
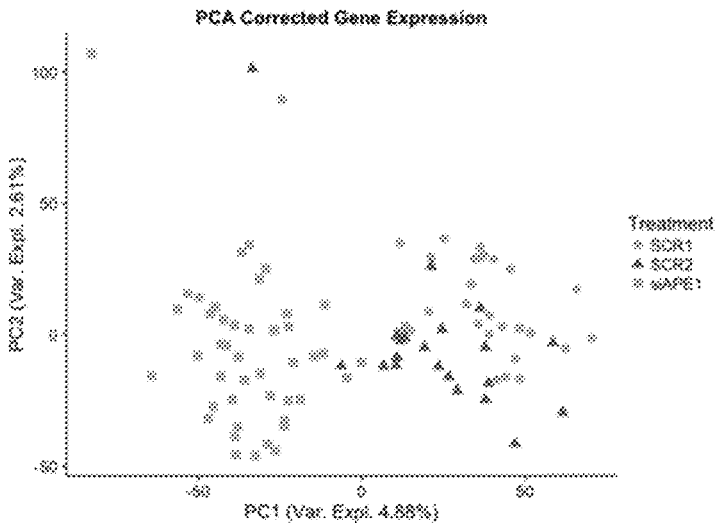

In the principal components plot following cell cycle correction (FIG. 8C), the SCR 1 and SCR 2 cells showed greater similarity, which resulted in the largest source of variation (i.e., the horizontal axis representing 4.88% of the total variation) now corresponding to the axis along which the siAPE1 and SCR cells were separated. Using cell cycle correction, the variation attributed to cell cycle annotated genes was effectively removed without removing the variation attributed to the differences between siAPE1 treatment and scrambled control. Thus, the largest source of variation between the cells was attributed to APE1 knockdown.

Differential Expression of Genes in the siAPE1 Knockdown and SCR Control Cells

Initially, 48 SCR cells and 48 siAPE1 cells were captured for sequencing. Two SCR and siAPE1 cells each were discarded prior to sequencing due to the presence of multiple cells in the capture site. Cell detection rates (percentage of genes detected in each cell) and gene detection rates (percentage of cells with a given gene expressed) were used for statistical quality control. A threshold of 5% was used for both detection rates, resulting in a dataset of 94 cells and 15,351 genes. With the median number reads per cell of 0.95 million, the total number of reads per cell was normalized to one million. After the aforementioned cell cycle correction was performed, a further three outlier cells were removed as they demonstrated signs of PCR bias with extremely high expression counts for some genes. After all quality control measures and the removal of outliers, the number of genes detected per cell averaged 7095.7 using the original (i.e. prior to correcting for cell-cycle confounding) gene expression counts. For each gene, the average number of cells with non-zero gene counts was 42.1 using the original gene expression counts.

The average APE1 expression in the remaining 46 cells in the SCR group was 101.6 reads per million. Of the siAPE1 cells (n=45), 25 cells had no detectable APE1 expression with zero APE1 counts. The remaining 20 cells showed diminished APE1 expression, with an average of 37.7 reads per million. A violin plot showing the distribution of the cells in each of these groups can be found in FIG. 9A.

While there are many available software packages that are commonly used for differential expression analysis, there are important differences between them in terms of what assumptions are made about the distribution of the count data arising from RNA-seq experiments. Two such R packages that use a generalized linear model in order to model non-normally distributed data are edgeR and BPSC. The package edgeR models the counts with an overdispersed (larger variance) Poisson distribution (also known as the negative-binomial distribution), which may not be appropriate for single cell RNA-seq data due the fact that there are many more zero counts in this data (a phenomenon referred to as zero-inflation) compared to bulk RNA-seq. The experimental results using edgeR resulted in a large number of differentially expressed genes, with a potentially high false discovery rate (data not shown). Alternatively, the R package BPSC models the counts in a more flexible beta-Poisson distribution that can sufficiently account for the zero-inflation in the single-cell data with the use of additional parameters in the model. Therefore, the BPSC R package was used in this Example for the differential expression analysis between SCR cells (n=46) and siAPE1 knockdown cells (n=45).

In order to facilitate comparison of the additional experimental designs later in this Example, the explicit mathematical expression of the linear component of the generalized model used for the baseline differential expression analysis is given by the following:

$$\mu_{ij} = \beta_{0j} + \beta_{1j} I[\text{siAPE1}]_i$$

where $\mu_{ij}$ is the expected value of the beta-Poisson count distribution of the $i^{th}$ cell for the $j^{th}$ gene, $\beta_0$ is the intercept and $\beta_1$ is the gene expression in log(Counts per Million). The expression $I[\text{siAPE1}]_i$ is an indicator variable that takes the value of one when a cell belongs to the siAPE1 knockdown group. The differential expression of the $j^{th}$ gene can then be tested using the null (denoted as $H_0$) and alternative (denoted as $H_1$) hypotheses as follows:

$$H_0: \beta_{1j} = 0$$

$$H_1: \beta_{1j} \neq 0$$

While only an expression for the statistical design above is included, it is worth emphasizing that the model is more sophisticated than simple linear regression, as the distributional assumptions made about the data are fundamentally different. With this statistical design, the BPSC R package reported 1,950 differentially expressed genes (DEGs) between the siAPE1 and SCR cells using a false discovery rate cutoff of 5%.

Figures 9A, 9B:
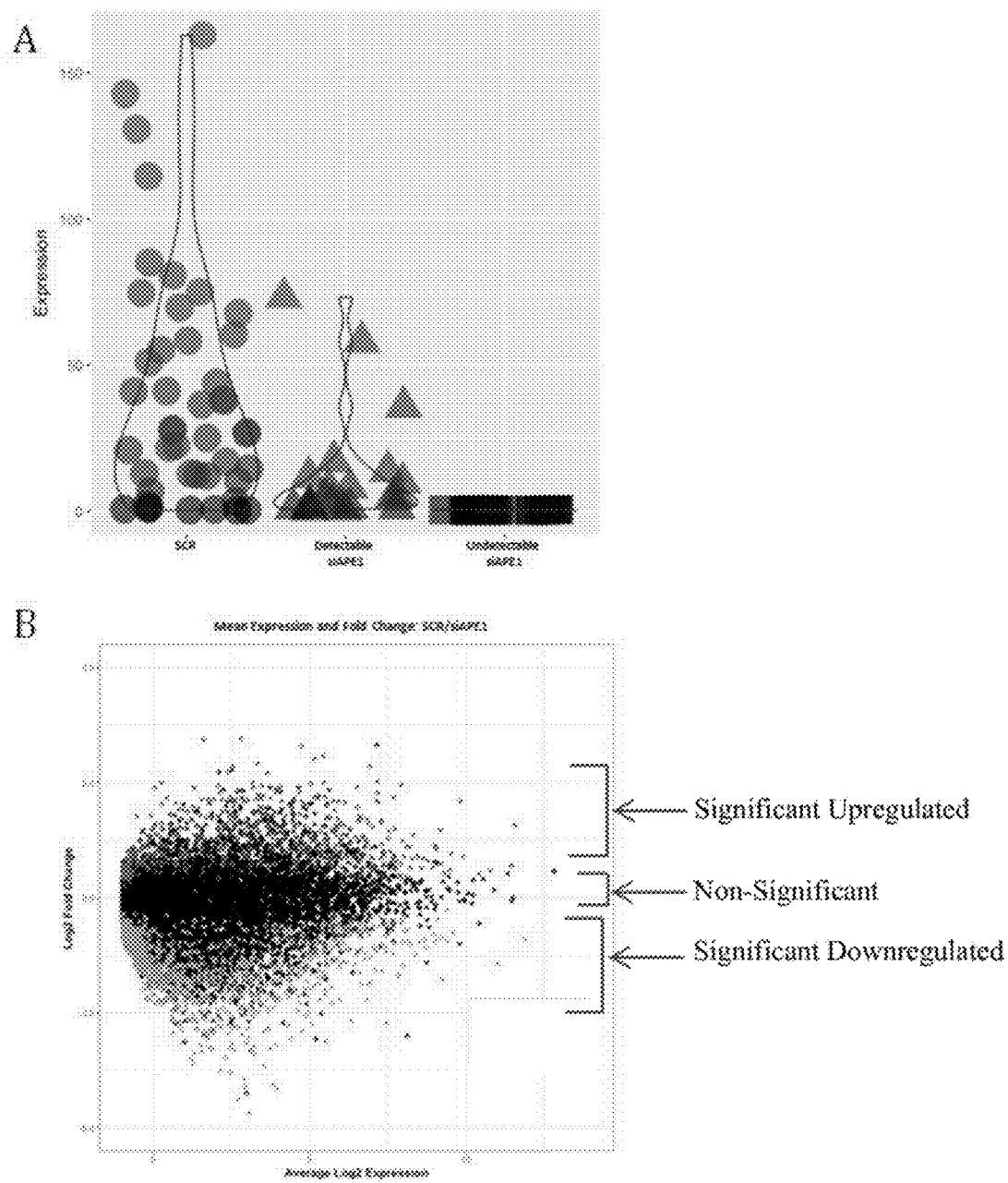
FIGS. 9A-9C depict the results of scRNA-seq and comparison of analyses.

71.7% of these differentially expressed genes had lower expression levels in the siAPE1 cells. In comparison, 58.5% of all genes sequenced had lower expression in the siAPE1 cells, though many of these genes had very low expression overall (FIG. 9B). Using Fisher's exact test on the number of genes with statistically significant increased/decreased expression vs genes with non-significant changes in expression, a p-value of 10-16 was obtained, a highly significant result. This indicated that the predominantly inhibitory effect of APE1 knockdown on the DEGs was greater than any global decrease in expression that may be caused due to external factors (such as cell viability).

Identifying Differentially Expressed Genes in Relation to APE1 Levels within the Cell One of the advantages of performing scRNA-seq is that it allows looking at APE1 expression in each individual cell. It was therefore possible to use this information to categorize cells within the siAPE1 group as having either undetectable APE1 (defined as a cell with zero expression of APE1) or detectable APE1 (defined as a cell with greater than zero expression of APE1). As previously mentioned, within the siAPE1 group there were 25 cells with undetectable APE1 (hereafter called undetectable siAPE1) and 20 cells exhibiting detectable but reduced APE1 expression (hereafter called detectable siAPE1).

The delineation of the siAPE1 cells allowed consideration of the SCR control, detectable siAPE1 and undetectable siAPE1 cells as three different categories. Such a model is appropriate if detectable siAPE1 cells were considered to be distinct from both undetectable siAPE1 as well as SCR control cells. The model in this case is given by $$\mu_{ij} = \beta_{0j} + \beta_{1j} I[\text{siAPE1}]_i I[APE1>0]_i + \beta_{2j} I[\text{siAPE1}]_i I[APE1=0]_i$$

where the expression $I[\text{siAPE1}]_i I[APE1>0]_i$ takes the value of one when the $i^{th}$ cell both belongs to the siAPE1 group and has non-zero APE1 expression (detectable siAPE1). The expression $I[\text{siAPE1}]_i I[APE1>0]_i$ takes the value of one when the $i^{th}$ cell belongs to the siAPE1 group and has no detectable expression of APE1 (undetectable siAPE1). A test for differential expression of the $j^{th}$ gene was performed using the null and alternative hypotheses $$H_0: \beta_{1j} = 0, \beta_{2j} = 0$$

$$H_1: \text{At least one of } \beta_{1j} \neq 0 \text{ or } \beta_{2j} \neq 0$$

This model has two parameters that can be tested for joint significance, whereas the initial SCR/siAPE1 model only had one parameter to test. While it is possible to estimate the joint significance with a single test of both parameters, the parameter specific significance was computed in order to gain insight into the individual differences between undetectable siAPE1 and detectable siAPE1 groups with respect to the SCR control. In practice, each of these parameters was tested separately and their joint significance was reported as the resulting p-values using Fisher's method. For two p-values $p_{1j}$, $p_{2j}$ corresponding to test of $\beta_{1j}$, $\beta_{2j}$ for the $j^{th}$ gene, the combined test statistic is described as $$F = -2 * \log(p_{1j}) - 2 * \log(p_{2j}) \sim X_4^2$$

where F is distributed as a chi-squared random variable with four degrees of freedom under the null hypothesis. The combined p-value p* is therefore computed as $$p^* = 1 - PX_4^2(F^* < F)$$

where $PX_4^2$ denotes the cumulative distribution function of a $X_4^2$ random variable and F* is the empirical test statistic computed similar to F above, only using the computed p-values for each gene. It is worth mentioning that Fisher's method, as described above, does not enforce the assumption of a consistent direction of differential expression of the two groups when compared to the control. While it may be useful to incorporate the assumption that the direction (positive or negative) of differential expression should be consistent among the detectable and undetectable siAPE1 groups directly into the statistical design of the analysis, these ideas were not pursued further.

Figure 9C:
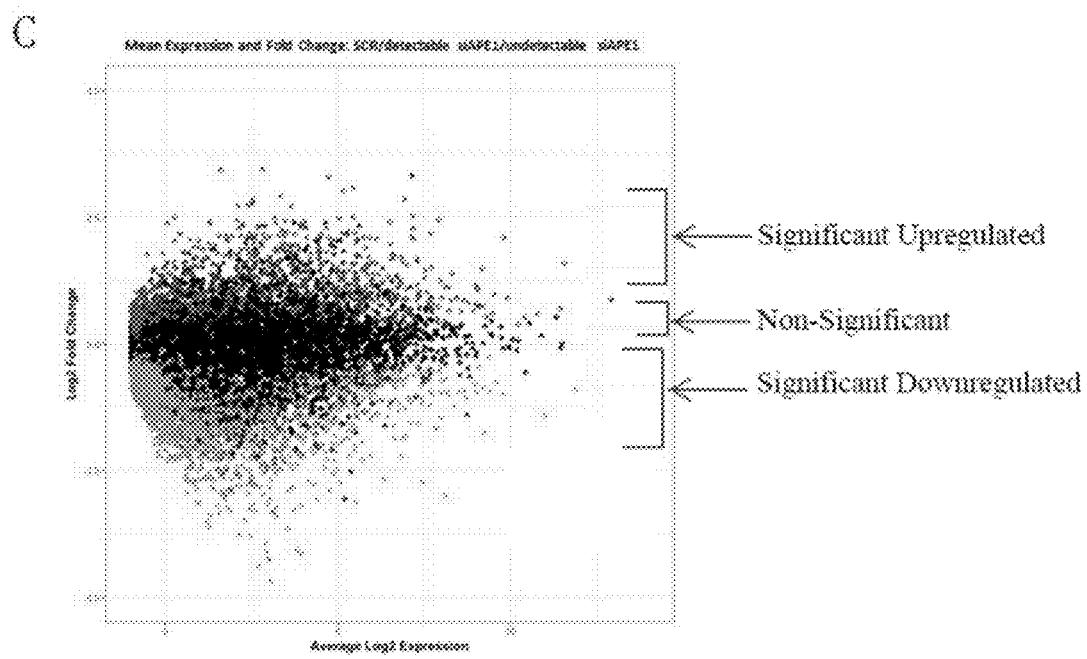

This analysis allows for detection of differences that may be present between SCR and detectable siAPE1 cells, between SCR and undetectable siAPE1 cells, or between SCR and both categories of siAPE1 cells. The joint analysis guards against a single outlier preventing a gene from being reported as differentially expressed as one parameter may be reported as insignificant, but not the other. Additionally, since the direction of the expression change of the DEGs is expected to be consistent as one moves from the SCR group to the detectable siAPE1 group to undetectable siAPE1 group, this experimental design aids in the interpretation of results and helps to identify genes potentially affected by outliers. This SCR/detectable siAPE1/undetectable siAPE1 analysis identified 2,837 genes using a false discovery rate of 5%. Of the 1,950 DEGs identified in the SCR/siAPE1 analysis, 1,945 (99.7%) were found to be differentially expressed in this subsequent analysis. Additionally, 72.1% of the DEGs were down-regulated (FIG. 9C), similar to the 71.7% down-regulated in the SCR/siAPE1 analysis. This consistency indicated that the increase in number of DEGs identified was due to the more rigorous statistical model, making it the preferable analysis.

Figure 10A:
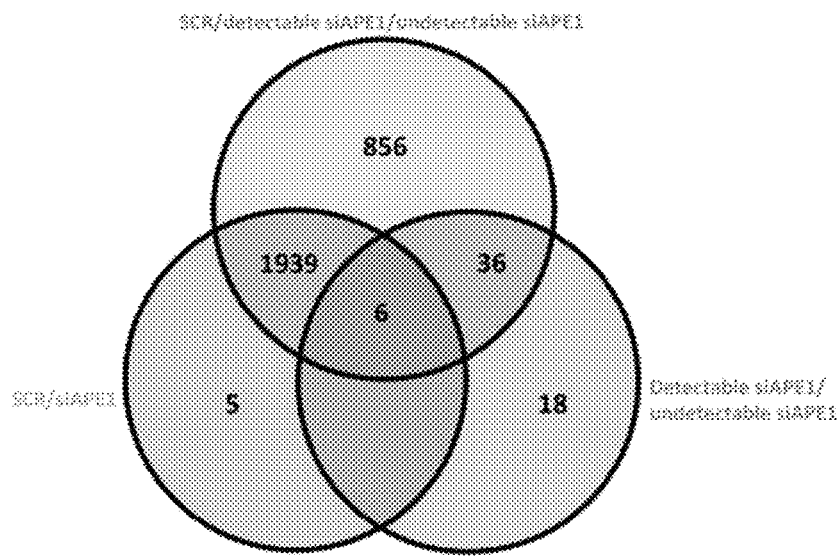
FIGS. 10A-10G depict the identification of differentially expressed genes in relation of APE1 levels.
Figure 10B:
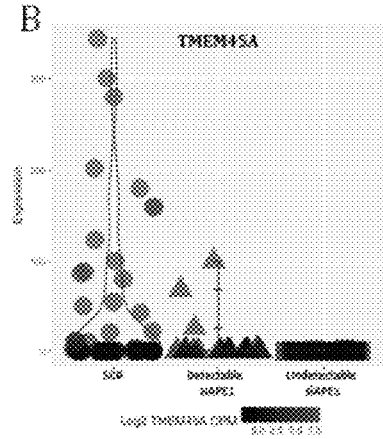
Figure 10C:
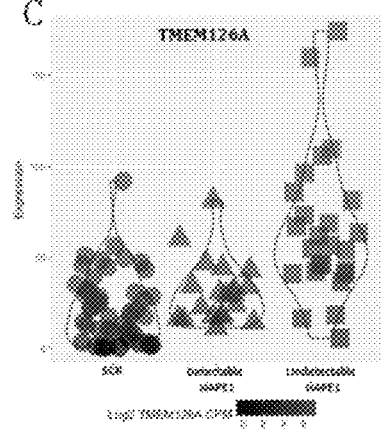
Figure 10D:
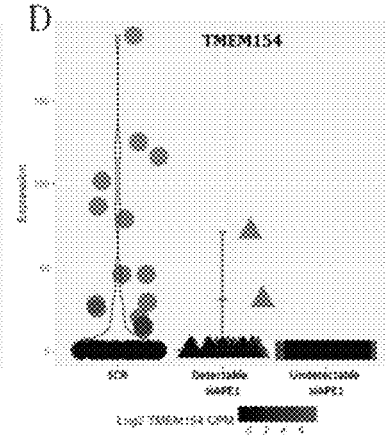
Figure 10E:
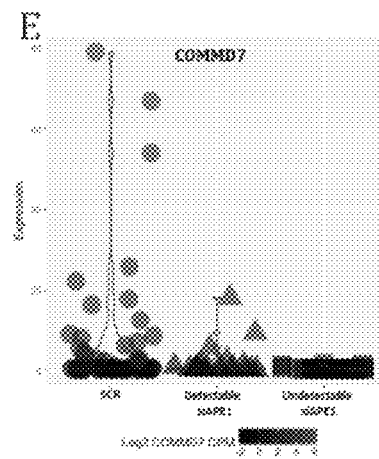
Figure 10F:
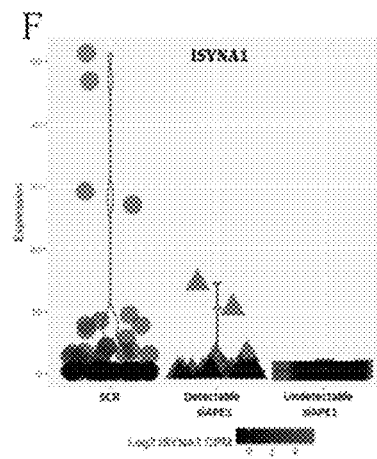
Figure 10G:
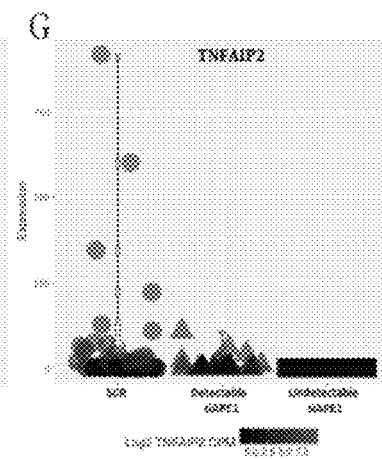

Analysis was also performed to investigate which genes were differentially expressed between the detectable and undetectable siAPE1 cells. This analysis was statistically underpowered due to the smaller sample size of the two cell groups. It resulted in only 60 DEGs being identified, indicating that the detectable and undetectable siAPE1 cells had similar gene expression patterns, especially when compared to the SCR control cells. When comparing the DEGs to the SCR/detectable siAPE1/undetectable siAPE1 results, 42 genes were found to overlap, while only six genes overlapped with the SCR/siAPE1 analysis (FIG. 10A). These six genes (TMEM45A, TMEM126A, TMEM154, COMMD7, ISYNA1 and TNFAIP2) were the only genes overlapping between all three analyses. Violin plots illustrating the expression of these genes in relation to APE1 expression per cell are shown in FIGS. 11B-11G. The presence of these six genes in all three analyses confirmed that, as APE1 levels decrease, the expression levels of these six genes changed further.

Determining the Clinical Relevance of the Differentially Expressed Genes

One overarching objective of this Example was to ascertain potential combinations of APE1 inhibition with clinically approved drugs that impinge on pathways impacted by altered APE1 expression, initially in pancreatic cancer, but eventually in other cancers. Toward this goal, the clinical relevance of the DEGs identified by the different analyses was investigated using The Cancer Genome Atlas (TCGA), which contains data such as tumor gene expression and clinical outcomes from cancer patients. Due to the small number of DEGs identified in the detectable siAPE1/undetectable siAPE1 analysis, it was excluded from this TCGA analysis. Both the SCR/siAPE1 and SCR/detectable siAPE1/undetectable siAPE1 analyses were utilized. Performing this TCGA analysis allowed for measurement of the clinical relevance of the DEGs identified in this Example, and also provided a performance metric for the two analyses.

The RTCGA toolbox was used to analyze the data from the TCGA. In this analysis, a gene is defined as clinically relevant if its expression level at the time of sequencing is statistically significantly related to the number of days until death in patients with pancreatic cancer. The statistical significance of a gene is determined using the Cox proportional hazards regression model, a commonly used model in clinical trials and biostatistics. Specifically, the outcome of days until death (accounting for censoring due to a patient still being alive at the time of sequencing) was regressed on the normalized gene expression data of patient tumor samples via bulk RNA-Seq using the R package survival. Only expression levels in the analysis were used, modeling one gene at a time across all tumor types and stages. In all, 178 patient tumor samples were included and a total of 20,501 genes were considered. Due to naming conventions and quality control procedures, only 10,292 were in common between the total number of genes sequenced in the scRNA-seq analysis and the TCGA analysis of survival outcomes. Therefore, for this analysis, the discussion will be limited to only these 10,292 genes. For this reason, the total number of differentially expressed genes reported below for both differential expression analyses are fewer than reported in previous sections.

The TCGA analysis resulted in 1,627 genes statistically significantly related to time until death using a false discovery rate of 5%. Of the 1,486 DEGs considered from the SCR/siAPE1 analysis, 246 genes (16.6%) were found to be clinically relevant. The SCR/detectable siAPE1/undetectable siAPE1 analysis identified 345 clinically relevant genes (16.3%) out of the available 2,115 DEGs.

The SCR/detectable siAPE1/undetectable siAPE1 analysis identified more DEGs that are clinically relevant without a change in the overall percentage of clinically relevant genes. This further illustrates that the 856 genes unique to the analysis were not statistical anomalies, but authentic results identified due to a more stringent statistical model. Because of this result, all following analyses were carried out using the SCR/detectable siAPE1/undetectable siAPE1 results.

Gene Expression Patterns in Cancer-Related Pathways

Ingenuity pathway analysis (IPA) was used to determine pathways regulated by APE1 based on the DEGs previously identified in the SCR/detectable siAPE1/undetectable siAPE1 analysis. Full pathway analysis results are in Table 5. A total of 104 canonical pathways were identified as overrepresented using a one-tailed Fisher's exact test. Data presented in FIG. 11A demonstrate the 20 most statistically significant overrepresented pathways, six of which were previously unlinked to APE1. The EIF2 signaling pathway (p-value=$1.58 \times 10-18$) with 70 DEGs was found to be the pathway most affected by APE1 knockdown. An overview of the pathway with the genes that were affected is presented in FIG. 11B, with a heatmap highlighting the 70 DEGs and their expression in each cell shown in FIG. 11C. Other previously unlinked pathways were the mTor pathway (p-value=$3.98 \times 10-12$) with 55 DEGs and the regulation of eIF4 and p70S6K signaling pathway (p-value=$3.63 \times 10-9$) with 42 DEGs. These pathways, along with the virus entry via endocytic pathway, regulation of Actin-based motility by Rho and putrescine degradation pathways, are now putatively linked to APE1 based on the scRNA-seq data, expanding APE1's already diverse role within the cell. In total, 44 pathways previously unassociated with APE1 were identified in this Example. These results highlight the importance of single cell RNA-seq in determining clear gene expression and pathway interactions.

TABLE 5

Complete results of IPA Pathway analysis.

| Ingenuity Canonical Pathways | p-value |
|---|---|
| EIF2 Signaling | $1.58 \times 10^{-18}$ |
| mTOR Signaling | $3.98 \times 10^{-12}$ |
| Regulation of eIF4 and p70S6K Signaling | $3.63 \times 10^{-9}$ |

TABLE 5-continued

Complete results of IPA Pathway analysis.

| Ingenuity Canonical Pathways | p-value |
|---|---|
| Mitochondrial Dysfunction | $8.12 \times 10^{-6}$ |
| Oxidative Phosphorylation | $1.02 \times 10^{-5}$ |
| Sumoylation Pathway | $2.63 \times 10^{-5}$ |
| Aldosterone Signaling in Epithelial Cells | $1.41 \times 10^{-4}$ |
| ILK Signaling | $3.71 \times 10^{-4}$ |
| Huntington's Disease Signaling | $4.07 \times 10^{-4}$ |
| Virus Entry via Endocytic Pathways | $5.5 \times 10^{-4}$ |
| Apoptosis Signaling | $5.5 \times 10^{-4}$ |
| Protein Kinase A Signaling | $5.89 \times 10^{-4}$ |
| Protein Ubiquitination Pathway | $7.08 \times 10^{-4}$ |
| Glycolysis I | $7.41 \times 10^{-4}$ |
| CDK5 Signaling | $9.12 \times 10^{-4}$ |
| NADH Repair | 0.001 |
| Putrescine Degradation III | 0.001 |
| Androgen Signaling | 0.001 |
| Regulation of Actin-based Motility by Rho | 0.002 |
| Aryl Hydrocarbon Receptor Signaling | 0.002 |
| Mitotic Roles of Polo-Like Kinase | 0.002 |
| Phospholipase C Signaling | 0.002 |
| Role of CHK Proteins in Cell Cycle Checkpoint Control | 0.003 |
| Gαi ± q Signaling | 0.003 |
| PI3K/AKT Signaling | 0.003 |
| ERK/MAPK Signaling | 0.003 |
| Spermine and Spermidine Degradation I | 0.004 |
| Synaptic Long Term Potentiation | 0.005 |
| Caveolar-mediated Endocytosis Signaling | 0.005 |
| Integrin Signaling | 0.005 |
| fMLP Signaling in Neutrophils | 0.005 |
| RAR Activation | 0.006 |
| HIF1α ± Signaling | 0.006 |
| Pyrimidine Deoxyribonucleotides De Novo Biosynthesis I | 0.006 |
| IL-17A Signaling in Fibroblasts | 0.007 |
| Unfolded protein response | 0.007 |
| NRF2-mediated Oxidative Stress Response | 0.007 |
| Production of Nitric Oxide and Reactive Oxygen Species in Macrophages | 0.007 |
| Breast Cancer Regulation by Stathmin1 | 0.009 |
| 3-phosphoinositide Degradation | 0.009 |
| Cell Cycle: G2/M DNA Damage Checkpoint Regulation | 0.009 |
| Actin Nucleation by ARP-WASP Complex | 0.01 |
| Pyrimidine Ribonucleotides Interconversion | 0.01 |
| DNA Double-Strand Break Repair by Non-Homologous End Joining | 0.01 |
| Glycogen Degradation III | 0.01 |
| Guanine and Guanosine Salvage I | 0.01 |
| Adenine and Adenosine Salvage I | 0.01 |
| Glioma Invasiveness Signaling | 0.01 |
| Ethanol Degradation II | 0.011 |
| Tryptophan Degradation X (Mammalian, via Tryptamine) | 0.011 |
| Ethanol Degradation IV | 0.011 |
| GNRH Signaling | 0.011 |
| 14-3-3-mediated Signaling | 0.012 |
| FcI³ Receptor-mediated Phagocytosis in Macrophages and Monocytes | 0.012 |
| Antigen Presentation Pathway | 0.012 |
| LPS-stimulated MAPK Signaling | 0.013 |
| p70S6K Signaling | 0.013 |
| Pyrimidine Ribonucleotides De Novo Biosynthesis | 0.014 |
| ATM Signaling | 0.015 |
| Oxidative Ethanol Degradation III | 0.016 |
| Endoplasmic Reticulum Stress Pathway | 0.016 |
| Insulin Receptor Signaling | 0.016 |
| CXCR4 Signaling | 0.017 |
| RhoGDI Signaling | 0.017 |
| Noradrenaline and Adrenaline Degradation | 0.018 |
| nNOS Signaling in Neurons | 0.018 |
| Signaling by Rho Family GTPases | 0.018 |
| Tight Junction Signaling | 0.019 |
| PI3K Signaling in B Lymphocytes | 0.020 |
| IL-3 Signaling | 0.020 |
| D-myo-inositol-5-phosphate Metabolism | 0.022 |
| Role of Tissue Factor in Cancer | 0.023 |
| Superpathway of Inositol Phosphate Compounds | 0.023 |
| PPAR Signaling | 0.026 |
| Cholecystokinin/Gastrin-mediated Signaling | 0.027 |
| Xenobiotic Metabolism Signaling | 0.027 |
| Ceramide Biosynthesis | 0.027 |
| Glycogen Degradation II | 0.027 |
| Assembly of RNA Polymerase II Complex | 0.028 |
| Sonic Hedgehog Signaling | 0.029 |
| D-glucuronate Degradation I | 0.029 |
| Germ Cell-Sertoli Cell Junction Signaling | 0.029 |
| Hypoxia Signaling in the Cardiovascular System | 0.031 |
| Salvage Pathways of Pyrimidine Ribonucleotides | 0.031 |
| Hereditary Breast Cancer Signaling | 0.031 |
| UVB-Induced MAPK Signaling | 0.034 |
| Growth Hormone Signaling | 0.034 |
| Estrogen Receptor Signaling | 0.036 |
| Role of IL-17A in Psoriasis | 0.036 |
| B Cell Receptor Signaling | 0.037 |
| Axonal Guidance Signaling | 0.037 |
| Histamine Degradation | 0.038 |
| Fatty Acid I²-oxidation I | 0.039 |
| Thrombin Signaling | 0.041 |
| tRNA Charging | 0.041 |
| RhoA Signaling | 0.042 |
| Phagosome Formation | 0.042 |
| Endothelin-1 Signaling | 0.042 |
| Molecular Mechanisms of Cancer | 0.042 |
| Neurotrophin/TRK Signaling | 0.043 |
| Agrin Interactions at Neuromuscular Junction | 0.046 |
| Retinol Biosynthesis | 0.047 |
| AMPK Signaling | 0.047 |
| The Visual Cycle | 0.047 |

A number of the significant pathways affected by APE1 knockdown confirm previous observations and therefore provided validation for the results. For example, the HIF1α signaling pathway, shown to be regulated by APE1, was found to be significantly down-regulated in the pathway analysis (p-value=0.006). Similarly, the mitochondrial dysfunction (p-value=8.12×10−6) and Huntington's disease signaling (p-value=4.07×10−4) pathways are both in the top ten significantly overrepresented pathways affected by APE1 knockdown. The mitochondrial dysfunction pathway has 37 DEGs, while there are 42 DEGs in the Huntington's disease signaling pathway. Mitochondrial dysfunction is believed to play a role in Huntington's disease pathology, and prior studies have demonstrated that APE1 is important for the maintenance of mitochondrial function. APE1 is also known to participate in mitochondrial DNA repair functions. While APE1 is known to influence these pathways, this Example expands the understanding of APE1 within the cell by implicating the genes in the pathways that are affected by APE1 knockdown.

Validating scRNA-Seq Results Using qRT-PCR

The scRNA-seq results of the SCR/siAPE1 analysis were validated by performing qRT-PCR in Pa03C cells following siRNA knockdown. A panel of genes, from distinct pathways and showing varying changes following knockdown, was chosen (FIG. 12A). These genes were present in both the SCR/siAPE1 and SCR/detectable siAPE1/undetectable siAPE1 analyses. Efficiency of siRNA knockdown was assessed using Western blots, with only samples exhibiting greater than 80% reduction in APE1 expression compared to the scrambled controls chosen.

In addition, validation of 3 genes that were differentially expressed and statistically significant in all analyses (SCR/siAPE1, Detectable siAPE1/undetectable siAPE1 and SCR/detectable siAPE1/undetectable siAPE1) was performed. The presence of these genes (FIG. 12B) within all 3 analyses indicates that their expression changes more dramatically with greater APE1 knockdown.

The genes that showed statistically significant increased or decreased expression in scRNA-seq exhibit changes in the same direction following qRT-PCR (FIG. 12C), with a decrease seen in the mRNA levels of CIRBP, COMMD7, ISYNA1, ITGA1, NOTCH3, PRDX5, RAB3D, SIPA1, TAPBP and TNFAIP2. The expression of BCRP and PPIF was significantly increased following knockdown. The fold changes from scRNA-seq were plotted against qRT-PCR fold changes in FIG. 12D. With an $R^2$ value of 0.82 and p<0.0001 (Linear Regression analysis), it was confirmed that the fold changes were consistent and validated the single-cell scRNA-seq studies.

Additionally, the "connectivity map" project compared the query gene expression signatures against a database of gene expression profiles derived from treating human cells with various agents to identify similarities and predict drug mechanisms. Incorporating drug sensitivity data of cell lines with similar gene expression profiles were used to predict effective combination treatments. Cancer Cell Line Encyclopedia (CCLE, https://portals.broadinstitute.org/ccle/home) contains baseline gene expression data of 1,036 cancer cell lines and pharmacologic profiles ($IC_{50}$, AUC) for anticancer drugs across 504 cell lines. CCLE gene expression profile set as the reference was used, as well as data from Genomics of Drug Sensitivity in Cancer (GDSC) and Cancer Therapeutics Response Portal (CTRP, http://portals.broadinstitute.org/ctrp/). Gene expression of CCLE cell lines and of Ref-1 knockdown single cells were normalized and ranked. A high correlation indicated that a drug that is effective in a CCLE cell will have relatively high probability of being effective in a cell whose Ref-1 signaling is inhibited. After identifying the CCLE cell lines with significantly high correlations with Ref-1 single cells (correlation >0.5), the frequency of these drugs that have high potency ($IC_{50}$<1 μM) on these CCLE cell lines was counted. Using this computational screening strategy, Table 6 lists drugs that are predicted to be most effective with Ref-1 inhibition, in order of the drugs that had the greatest number of cell lines. The agents in Table 6 will be utilized in combination treatments with APX3330 for further analysis.

TABLE 6

List of compounds likely to synergize with APX3330 based on CCLE and single cell RNAseq

| Class of drug | | P value |
|---|---|---|
| HDAC inhibitors | Panobinostat | 2.60E−07 |
| | Entinostat | 1.00E−06 |
| | Vorinostat | 1.87E−06 |
| | Merck60 | 1.13E−10 |
| | Apicidin | 2.31E−08 |
| | BRD-K66532283 | 2.16E−07 |
| Nucleoside analogs | Decitabine | 4.97E−09 |
| | Gemcitabine | 4.20E−07 |
| | Clofarabine | 1.83E−06 |
| | Ara-C | 6.36E−08 |
| DNA damaging agents | Doxorubicin | 1.66E−10 |
| | Etoposide | 5.42E−07 |
| | Topotecan | 8.36E−07 |
| | Bendamustine | 1.18E−06 |
| | Dacarbazine | 1.66E−06 |
| | Mitomycin C | 6.78E−06 |
| | Chlorambucil | 6.65E−06 |
| RTKi (Receptor tyrosine kinases) | Axitinib | 3.32E−09 |
| | Sunitinib | 4.91E−09 |
| | KW-2449 | 9.39E−09 |
| | MGCD-265 | 3.46E−07 |

TABLE 6-continued

List of compounds likely to synergize with APX3330 based on CCLE and single cell RNAseq

| Class of drug | | P value |
|---|---|---|
| | Imatinib | 5.93E−07 |
| | Pazopanib | 2.65E−07 |
| BRDi (Bromodomain) | I-BET151 | 6.99E−09 |
| | GSK525762A | 9.65E−08 |
| | JQ-1 | 1.48E−07 |
| Jak2 | NVP-BSK805 | 1.50E−07 |
| | Momelotinib | 3.29E−07 |
| Tubulin polymerization | Vincristine | 7.59E−08 |
| | CHM-1 | 4.05E−07 |
| PLKi (Polo-like kinase) | GSK461364 | 6.66E−08 |
| | BI-2536 | 9.46E−07 |
| Mdm2i | Serdemetan | 1.11E−06 |
| | HLI 373 | 6.22E−06 |
| S1Pi | FTY720 | 1.46E−06 |

Example 2

In this Example, Ref-1 inhibition in combination with docetaxel and trametinib was analyzed.

Standard 3D co-culture assays as prepared in Arpin, C. et al., Mol Cancer Ther 15, 794-805 (2016); Logsdon, P. et al., Mol Cancer Ther 15, 2722-2732 (2016); Cardoso, A. et al., PloS one 7, e4742 (2012); and Kelley, M. et al., The Journal of pharmacology and experimental therapeutics 359, 300-309 (2016) were used to evaluate the cytotoxicity of the combinations on tumor cells as well as cancer-associated fibroblasts.

As shown in FIG. 14, Ref-1 inhibition in combination with docetaxel and trametinib was shown to be more effective than either agent alone. Docetaxel was chosen because it was gave the highest number of CCLE cell lines (115 lines) that were likely to synergize with Ref-1 inhibition; Trametinib was chosen due to the prevalence of PDAC lines (14%) in the CCLE lines revealed from the computational screening strategy.

Example 3

In this Example, inhibition of Ref-1 via APX3330 in combination with gemcitabine was analyzed.

Standard 3D co-culture assays as described in Example 2 were used to evaluate the cytotoxicity of the combination on tumor cells as well as cancer-associated fibroblasts.

The scientific premise of this approach is based on: 1) a computational approach providing chemotherapeutic agents to partner with APX3330 that result in augmented effects on PDAC killing; and 2) 3D and in vivo studies with APX3330 and gemcitabine demonstrating that addition of APX3330 increased the effects of gemcitabine. In the 3D spheroid model (FIGS. 14A & 14B), it was demonstrated a dose-dependent combination effect of gemcitabine and APX3330 on a patient-derived tumor line, Pa03C in co-culture with CAFs. There was a reduction in the area of the CAFs with APX3330 alone, but the effects were not enhanced with the addition of gemcitabine (See green bars, FIG. 14B).

Additionally, the beneficial effects of combining APX3330 with gemcitabine in vivo were demonstrated (FIG. 14C). APX3330 (25 mg/kg) was combined with a standard dose of gemcitabine (35 mg/kg) to demonstrate the "additive" effects of APX3330 in reducing pancreatic tumor volumes. The data in FIG. 14C is tumor volume at sacrifice. Combination therapy was well-tolerated. There was a significantly decreased tumor volume in the combination treatments of APX3330 with gemcitabine compared to the single agents alone. All treatments, single or combination were significantly different from the vehicle control. These data demonstrate a novel combination effect when APX3330 is combined with gemcitabine in a xenograft model as well as lend support to the interrogation of combination therapy with APX3330 and the FDA approved agents in Table 6.

Example 4

In this Example, the inhibition of Ref-1 via APX3330 in combination with the PDH/KDGH inhibitor, CPI-613, was analyzed.

Standard 3D co-culture assays as described in Example 2 were used to evaluate the cytotoxicity of the combination on tumor cells as well as cancer-associated fibroblasts.

As shown in FIGS. 15A-15C, there was greater than 50% killing of HCT-116 colon cancer cells using 0.2, 0.8, 1.6, 3.1, 6.3 µM APX3330 when combined with 100 and 75 µM CPI-613.

Example 5

In this Example, differences in gene expression of PDAC cell lines in response to APE1 siRNA knockdown were analyzed.

The effect of APE1 siRNA knockdowns were then analyzed in other PDAC low passage patient-derived cells. The effect of APE1 knockdown on these genes varied between the different patient lines, as shown in FIG. 16A-16D, Pa02C, a cell line generated from liver metastasis of a PDAC patient, showed generally similar gene expression patterns to the Pa03C cells, which were also isolated from PDAC liver metastasis. In Pa02C cells, BCRP, COMMD7, ISYNA1, ITGA1, PRDX5, RAB3D, SIPA1 and TNFAIP2 all demonstrated a decrease in expression, while NOTCH3 and PPIF were significantly increased following knockdown (FIG. 16A). Interestingly, while changes in expression of BCRP and NOTCH3 were significant, they were in opposing directions to the changes seen in Pa03C cells.

Panc10.05 cells, derived from a primary PDAC tumor, exhibited similar results to Pa03C cells, with eight of the 12 genes showing similar changes in expression (FIG. 16B). COMMD7, ITGA1, RAB3D, SIPA1, TAPBP and TNFAIP2 show decrease, while BCRP and PPIF increased expression. In contrast, CIRBP, ISYNA1, NOTCH3 and PRDX5 show no change in expression in the Panc10.05 cells.

Panc198 cells, also originating from a primary tumor, produced the most varied results (FIG. 16C). No change in expression was seen for BCRP, CIRBP, ISYNA1, NOTCH3, PRDX5, PPIF, SIPA1 and TAPBP. COMMD7, ITGA1, RAB3D and TNFAIP2 all showed significantly decreased expression. COMMD7, ITGA1, RAB3D and TNFAIP2 were significantly changed in all four patient-derived cell lines tested (FIG. 16D).

Only six genes overlapped between the three analyses (TMEM45A, TMEM126A, TMEM154, COMMD7, ISYNA1 and TNFAIP2) (FIG. 10A), demonstrating that only these six genes were further affected as APE1 levels decreased. This was an unexpected result, as a larger number of genes was expected to change further as APE1 levels decrease. Consequently, these results indicate that the change in expression of most genes following APE1 knockdown is apparent when APE1 is at least reduced by 80% (based on the number of APE1 transcripts in the siAPE1 cells), and further reduction of APE1 does not significantly increase or decrease most genes further. In the case of several down-regulated genes, this was because initial APE1 knockdown (detectable siAPE1 cells) already reduced their expression to near zero, which meant further reduction of APE1 (undetectable siAPE1 cells) had no effect on them.

Discussion

BCRP (Breast cancer resistance protein)/ABCG2 is an ATP-binding cassette (ABC) transporter that is one of the proteins responsible for multidrug resistance of cancer cells. In PDAC, high BCRP expression corresponds to carcinogenesis, tumor progression, early recurrence and poor survival. Several chemotherapeutic drugs are substrates for BCRP, which results in their efflux from and reduced accumulation within the cells. An affected drug of particular interest is 5-fluorouracil (5-FU), which is currently part of the treatment regimen for PDAC patients. Therefore, the discovery that APE1 knockdown affects BCRP expression is crucial when looking at future drug combinations to improve survival in PDAC. Combining APE1-targeted agents with 5-FU in tumors genetically similar to Pa02C should respond favorably to this combination due to reduced BCRP expression. A study in colon cancer stem cells indeed demonstrated dramatically increased cell killing when 5-FU and an inhibitor of APE1, APX3330, were used in vivo.

NOTCH3, a highly conserved member of the eponymous Notch signaling pathway, has been implicated in cell survival, proliferation, differentiation, development and homeostasis. Increased Notch3 protein levels have been identified as a prognostic marker for PDAC patients, and leads to increased tumor invasion, metastasis and shortened patient survival. Because of this, Notch3 has become a target for novel cancer therapies. γ-secretase inhibitors and DLL4-inhibiting antibodies both target proteins upstream of Notch3, leading to the inhibition of the Notch signaling pathway. The identification of Notch3 as being affected by APE1 opens up the possibility of combining APE1-targeted therapies with these inhibitors to enhance (in Pa03C) or counteract (in Pa02C) the effects of APE1 inhibition on NOTCH3 expression and function in PDAC.

Of the 10 other genes validated, four of them, COMMD7, ITGA1, RAB3D and TNFAIP2 showed decreased expression in all four patient cell lines (FIG. 16D). COMMD7, ITGA1, RAB3D and TNFAIP2 have all been shown to be upregulated in various cancers including PDAC. While it cannot be assumed these changes will be universal in all PDAC samples, this consistency suggests that some of these genes could make promising targets or biomarkers for APE1-based therapy or combination therapies that potentially will be useful across multiple PDAC tumor subtypes and in other tumor types. Furthermore, these genes represent a fraction of the genes identified in this initial Example affected by APE1 knockdown. The identification of pathways formerly unassociated with APE1, as well as known pathways exhibiting DEGs not previously linked with APE1, opens up novel targets for APE1-based combination therapies. In fact, initial experiments targeting some of the identified pathways in combination with APE1 inhibition appear to be promising.

Example 6

Development of additional Ref-1 redox inhibitors based on APX3330 and related families of compounds has been undertaken. A number of analogs have been synthesized based on structure-activity relationship (SAR). Changes include alterations of the dimethoxybenzoquinone with a napthoquinone ring, modification of the carboxylic acid, carbon chain on the double bond shortened, and substitution of the methyl group on the ring structure with hydrogen or various halogens. APX3330 exists as a charged molecule at physiological pH; the addition of amide derivatives of carboxylic acid altered APX3330's physical properties. Also, the lipophilic carbon chain was shortened on the double bond, making the new compounds less lipophilic. These changes resulted in new compounds (e.g., APX2009 and APX2014) that exhibited greater potency than APX3330 during in vitro testing.

In this Example, the efficacies of analogs, APX2009 and APX2014, as well as APX3330, were analyzed in 3D spheroid models of pancreatic cancer.

Co-Culture Model: To make 3D spheroid models, 3D tumor spheroid cultures were grown in DMEM growth media supplemented with 5% FBS (Hyclone, Logan, UT) and containing 3% Reduced Growth Factor Matrigel (RGF, BD Biosciences) in ultra low-attachment 96-well plates (Corning Life Sciences) as described in Sempere et al., Cancer biology & therapy 2011, 12(3), 198-207; Arpin et al., Mol Cancer Ther 2016, 15(5), 794-805; and Logsdon et al., Mol Cancer Ther 2016, 15(11), 2722-2732. These spheroid cultures were grown with tumor cells alone or in the presence of CAFs (cancer-associated fibroblasts). To track growth throughout the culture time and differentiate the cell types in the cultures, tumor cells were stably transduced with TdTomato (red channel), and CAFs were stably transduced with EGFP (green channel). These modifications were performed in fresh, low-passage cells to preserve the heterogeneity and unique genetic characteristics of the patient cells, and growth rates were similar to uninfected cells. 3D spheroid cultures were analyzed on Days 4, 8 and 12 after plating using Thermo ArrayScan high-content imaging system as described in Logsdon, Mol Cancer Ther 2016, 15(11), 2722-2732 and Lindblom et al., Toxicologic pathology 2012, 40(1), 18-32. 3D culture images were obtained by the ArrayScan system at 2.5× magnification with filters for TdTomato and EGFP. Quantification of tumor and CAF intensity and area was accomplished using 2D projections of these 3D images. Spheroids were treated on Days 4 and 8 following ArrayScan analysis/imaging. Confocal images of 3D spheroid cultures were captured with a confocal/two-photon Olympus Fluoview FV-1000 MPE system (Olympus Scientific Solutions America; Waltham, MA) at the Indiana Center for Biological Microscopy facility (Indianapolis, IN) as previously described in Logsdon et al., Mol Cancer Ther 2016, 15(11), 2722-2732.

These spheroid cultures were grown with Panc10.05 tumor cells alone or in the presence of CAFs(cancer-assoicated fibroblasts). Pa03C cells were plated into 3D cultures alone or with CAF19 cells. Spheriods were treated with increasing concentrations of napabucasin, vehicle (DMSO), APX3330 at 25 µM or 35 µM or combination of napabucasin and APX3330 on days 4 and 8 following ArrayScan analysis/imaging. Tumor cell growth in these spheroids was measured via fluorescence intensity (as well as area, data not shown) on days 4, 8, and 12 after plating. 3D cultures were treated with APX3330 (top row), APX2009 (middle row), or APX2014 (bottom row) following measurements on days 4 and 8. Graphs are means with standard deviations of N=3.

As shown in FIG. 17, APX3330 and its second generation compounds, reduced cell growth, cell proliferation. Moreover, APX2009 and APX2014 appeared as effective as APX3330 even when administered at a lower dosage.

Example 7

In this Example, the combination of APX330 and the STAT3 inhibitor, napabucasin (BB1-608-STAT3 inhibitor), was analyzed for its tumor killing ability in a patient-derived 3D spheroid model of pancreatic cancer as described in Example 6.

As shown in FIGS. 18, the combination of APX3330 and napabucasin had a synergistic tumor killing effect.

Example 8

In this Example, combination therapy with APE1/Ref-1 inhibitors in a PDAC 3D co-culture model prepared as in Example 6 was analyzed.

Pa03C and Panc10.05 tumor cells were grown in 3D cultures in the presence of CAFs. Spheroids were treated with either single agents, vehicle (DMSO) or combination of targeted agents on days 4 and 8 (black arrows), and the intensity of tumor (red) and CAF (green) were quantified as described in Example 7 every 3-4 days in culture.

As shown in FIGS. 19A & 19B, the combination of APX3330 and napabucasin had a synergistic tumor killing effect on pancreatic tumor cells.

Additionally, the combination of APX330, or its analog APX2009, and the STAT3 inhibitor, napabucasin (BB1-608-STAT3 inhibitor), was analyzed for its tumor killing ability in the PDAC 3D co-culture model using the same methodology. As shown in FIGS. 20A & 20B, both the combination of APX3330 and napabucasin and the combination of APX2009 and napabucasin had a synergistic tumor killing effect as compared to any of the agents alone.

Example 9

In this Example, the combination of APX330 and the STAT3 inhibitor, napabucasin, was analyzed for its tumor killing ability in a genetic PDAC model in vitro and in vivo.

In murine KPC (Kras$^{LSL \cdot G12D/+}$; Trp$^{53R172H/+}$; Pdx1$^{Cretg/+}$) cells derived from the GEMM, enhancement of Napa-induced cytotoxicity is observed when APX3330 is added to the Napabucasin (FIG. 21A). Alamar blue proliferation-based assay demonstrates the syngergistic nature of the APX+Napabucasin combination after 3 days incubation with these agents.

In a pilot study with a highly proliferative and aggressive in vivo co-culture model using patient derived tumor cells (Pa03C) and CAFs injected together, the co-treatment of APX3330+Napa significantly inhibited tumor growth 46% (FIG. 21B, p=0.012). Sub-lethal doses of the single agents were used in order to see the effect of the combination treatment, and the combination treatment was well tolerated in mice. Tumor volume is significantly reduced after two weeks of treatment.

Example 10

In this Example, the combination of APX330 and the CA9 inhibitor, SLC-0111, was analyzed for its tumor killing ability in a 3D co-culture pancreatic cancer tumor model prepared as described in Example 6.

Pa03C and 10.05 cells were plated into 3D cultures with CAF19 cells, and tumor cell growth in these spheroids was measured via fluorescence intensity on days 4, 8, 12, and 16 after plating. 3D cultures were treated with APX3330 and SLC-0111 following measurements on days 4, 8, and 12. Differences between groups were determined using Tukey's multiple comparisons test: ***$p<0.001$ vs. DMSO; ++$p<0.01$ vs. APX3330; +++$p<0.001$ vs. APX3330; ^^$p<0.01$ vs. SLC-0111; ^^^$p<0.001$ vs. SLC-0111. Graphs are means with standard deviations of N=3. Fluorescent images of Pa03C tumor cells (red channel) and CAFs (green channel) in these spheroids were captured on day 12.

As shown in FIGS. 22A-22C, dual-targeting of CA9 and APE1 kills PDAC tumors better than either agent alone.

Example 11

In this Example, combinations of APX330 and one other therapeutic agent (e.g., Bcl2 antagonist, HDAC 1 and 3 inhibitor, TKI inhibitor) were analyzed for their tumor killing abilities in a 3D co-culture pancreatic cancer tumor model prepared as described in Example 6.

Pa03C and Panc10.05 tumor cells were grown in 3D cultures in the presence of CAFs (cancer-associated fibroblasts). Spheroids were treated with either single agents, vehicle (DMSO) or combination of targeted agents on Days 4 and 8, and the area of tumor (red) and CAF (green) were quantified following 12 days in culture. Results are shown in FIGS. 23A-23E.

Example 12

In this Example, combinations of APX330 and one of either the STAT3 inhibitor, napabucasin, or the TCA cycle inhibitor, CPI-613, were analyzed for their tumor killing abilities in a 3D co-culture pancreatic cancer tumor model as described in Example 6.

Pa03C and Panc10.05 tumor cells were grown in 3D cultures in the presence of CAFs. Spheroids were treated with either single agents, vehicle (DMSO) or combination of targeted agents on Days 4 and 8 (black arrows), and the area of tumor (red) and CAF (green) were quantified following 12 days in culture. Results are shown in FIGS. 24A-24C.

Example 13

In this Example, the combination therapy of APX3330 and STAT3 inhibitor, Ruxolitinib, was analyzed for inhibiting PDAC tumor growth.

Initially, it was confirmed that ruxolitinib blocks the phosphorylation of p-STAT3 (Y705) in the 3D co-culture model. Confirmation of inhibition of STAT3 activation was done via immunoblotting for pSTAT3 Y705 residue after 4 hours of Ruxolitinib treatment (12.5 µM) in the 3D assay 8-10 days post plating. Total STAT3 protein is provided as a loading control and reference for the levels of STAT3 in both cell types. Representative western blot is shown from an n of 3. (see FIG. 26).

Using the 3D co-culture pancreatic cancer tumor model as described in Example 6, low passage patient-derived tumor cells, Pa03C, were grown in 3D cultures in the presence and absence of CAFs. Spheroids were treated with Ruxolitinib alone and in combination with APX3330 (40 µM), and the area of tumor (red channel) and CAF19 #1 (green channel) were quantified following 12 days in culture, n=4 but this is a representative plot.

As shown in FIG. 25, dual-targeting of Ref-1/APE1 and Jak/STAT signaling inhibited PDAC tumor growth in the 3D co-culture model.

Example 14

In this Example, the combination therapy of APX3330 and STAT3 inhibitor, Ruxolitinib, was analyzed for delaying tumor growth in a flank co-culture model.

Particularly, as shown in FIG. 27, in vivo efficacy experiments with patient-derived Pa03C tumors showed a significant tumor growth delay in vivo. Ruxolitinib (Rux) in combination with APX3330 also showed a reduction in tumor volume in this aggressive co-culture model with patient-derived line and CAFs.

Example 15

In this Example, the combination therapy of APX3330 and STAT3 inhibitor, Ruxolitinib, was analyzed to ensure that the treatment was not killing all CAFs in a co-culture model of PDAC in mice.

Immunohistochemistry (IHC) with vimentin as a marker for the CAFs was used to ensure that the combination treatment was not killing all the CAFs in the co-culture model. Staining for vimentin was performed at sacrifice.

Methods for Immunohistochemistry staining of tumor tissue: Tissues were fixed overnight at room temperature in 10% NBF after which they were transferred through graded concentrations of alcohol to xylene inside a Leica Automated Vacuum Tissue Processor. Tissues were embedded in paraffin before being cut into 5-mm thick sections, mounted onto positively charged slides, and baked at 60° C. The slides were then deparaffinized in xylene and rehydrated through graded alcohols to water. Antigen retrieval was performed by immersing the slides in a Target Retrieval Solution (Dako) for 20 minutes at 90° C. (in a water bath), cooling at room temperature for 10 minutes, washing in water, and then proceeding with immunostaining. Slides were blocked with protein blocking solution (Dako) for 30 minutes. All subsequent staining steps were performed using the Dako FLEX SYSTEM on an automated Immunostainer; incubations were done at room temperature and Tris-buffered saline plus 0.05% Tween 20, pH 7.4 (TBS-Dako Corp) was used for all washes and diluents. The primary antibody was anti-mouse vimentin and p-STAT3. Control sections were treated with an isotype control using the same concentration as primary antibodies to verify the staining specificity. For whole slide digital imaging, the Aperio ScanScope CS system was used. The system imaged all slides at 20×. The control and treatment groups were then evaluated for statistical differences. Results are shown in FIGS. 28A & 28B.

Treatment of the implanted tumors started on day 11 post implant. Particularly, the co-cultures implanted included $2.5 \times 10^6$ tumor cells +/-5 ×$10^6$ CAFs, providing a 1:2 ratio of tumor cell to CAF. The tumors had an initial average tumor size of about 200 mm$^3$. The mice were then administered either 50 mg/kg APX3330 BID in 4% Cr:EtOH, 50 mg/kg Rux SID pm in 4% Cr:EtOH, or combinations of the agents. Treatment schedule consisted of treating for 5 days and then giving 2 days off treatment until the tumors reached an average size of 2000 mm$^3$. With no treatment, the mice reached an average tumor size of 2700 mm$^3$ at day 26, with Rux or APX3330 treatment alone, the mice reached an average size of 1750 m$^3$ at day 28, and with the combination therapy, the mice reached an average size of 1200 mm$^3$ at day 31.

Example 16

In this Example, the anti-cancer efficacy of oxaliplatin with APX3330 in colon cancer orthotopic tumors was analyzed.

Figures 29A, 29B, 29C, 29D, 29E, 29F, 29G:
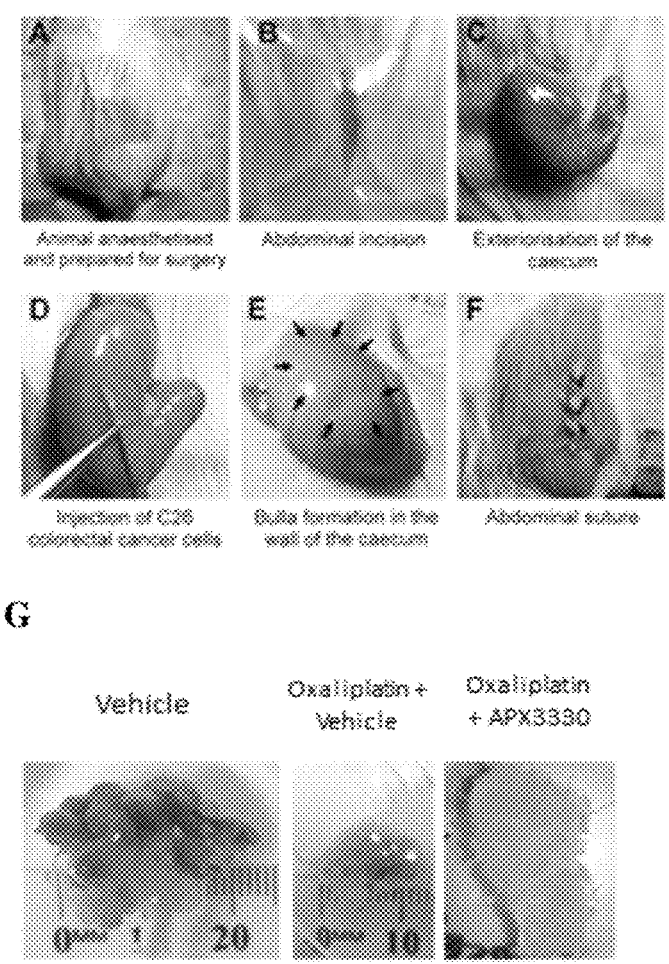

Immune competent mice were injected with mouse C26 colon cancer cells in the caecum (FIG. 29A). Animals were treated with either oxaliplatin or oxaliplatin with APX3330 and tumor size determined compared to vehicle controls (FIG. 29B). There was a dramatic and significantly increased tumor cell killing the in oxaliplatin and APX3330 treated mice compared to the mice treated with oxaliplatin alone (FIGS. 29B & 29D). Additionally, APX3330 treatment alleviated oxaliplatin induced loss of myenteric neurons in the colon of the CRC mice (FIG. 29C).

Example 17

In this Example, the combination therapy of APX2014 and STAT3 inhibitor, napabucasin, was analyzed for its tumor killing ability in mouse colon cell line MC-38.

MC-38 cells (Yunhua Liu) were seeded in a 96-well tissue culture plate at 2000 cells/well in DMEM+10% FBS and grown overnight at 37° C., 5% $CO_2$. Media was exchanged with DMEM+5% FBS drug media containing Napabucasin (SELLECK CHEMICALS) serially diluted 1:2 in a 5-point spread of 750 nM to 47 nM and spiked with APX2014 at EC30 (3.0 uM), or APX2014 EC10 (2.0 uM), or alone for single agent. Cells were incubated for 72 hours at 37° C., 5% $CO_2$. Media was exchanged with DMEM+5% FBS+10% Alamar blue fluorescent cell viability indicator (Invitrogen™) and incubated 4 hours at 37° C., 5% $CO_2$ and then read on a fluorescent reader (Synergy™ H4 BioTek). Results are shown in FIG. 30A. FIG. 30B shows APX2014 single agent effect. Data shown is the average of 3 separate cytotoxicity assays; each assay normalized to media only control.

Example 18

In this Example, the combination therapy of APX3330 and PDH and alpha-KDH Metabolic inhibitor, CPI-613, was analyzed for its tumor killing ability in human adenocarcinoma colon suspension cell line Colo-201.

Colo-201 (Yunhua Liu) was seeded in a 96-well tissue culture plate at 2000 cells/well in RPMI+Sodium Pyruvate+10% FBS and grown overnight at 37° C., 5% $CO_2$. 2× Drug Media RPMI+Sodium Pyruvate+5% FBS was added at dosages of APX3330 (Apexian) in a 5-point spread from 75 uM to 6.3 uM and spiked with CPI-613 (Apexbio Technology) at 75 uM, or 50 uM, or alone for single agent. Cells were incubated 72 hours at 37° C., 5% $CO_2$ and then 10% Alamar blue fluorescent cell viability indicator (INVITROGEN™) was added directly to plate. Indicator was incubated 4 hours at 37° C., 5% $CO_2$, and then read on a fluorescent reader (SYNERGY™ H4 BioTek). FIG. 31A shows APX3330 and CPI-613 single agent effects. FIG. 31B shows APX3330 and CPI-613 synergistic combo effects. FIG. 31C shows APX3330 and CPI-613 EC50 (CalcuSyn). FIG. 31D depicts Chou-Talalay Index (CI) of dose combinations (CalcuSyn). FIG. 31E depicts synergistic drug combinations (CalcuSyn) of APX3330 spiked with 50 uM CPI-613 or 75 uM CPI-613. Drug combination synergy was observed at APX3330 dosages of 75 uM and 50 uM when spiked with 50 uM CPI-613. Synergy was observed at all but one APX3330 dosage (6.3 uM) when spiked with 75 uM CPI-613. Data shown is the average of 3 separate cytotoxicity assays; each assay normalized to media only control.

Example 19

In this Example, the combination therapy of APX3330 and PDH and alpha-KDH Metabolic inhibitor, CPI-613, was analyzed for its tumor killing ability in human carcinoma colon cell line HCT-116.

HTC-116 (Yunhua Liu) was seeded in a 96-well tissue culture plate at 2000 cells/well in DMEM+10% FBS and grown overnight at 37° C., 5% $CO_2$. Drug Media DMEM+5% FBS was added at dosages of APX3330 (Apexian) in a 5-point spread from 75 uM to 6.3 uM and spiked with CPI-613 (Apexbio Technology) at 75 uM, or 50 uM, or alone for single agent. Cells were incubated for 72 hours at 37° C., 5% $CO_2$. Media was exchanged with DMEM+5% FBS+10% Alamar blue fluorescent cell viability indicator (INVITROGEN™) and incubated 4 hours at 37° C., 5% $CO_2$ and then read on a fluorescent reader (SYNERGY™ H4 BioTek). FIG. 32A shows APX3330 and CPI-613 single agent effects. FIG. 32B shows APX3330 and CPI-613 synergistic combo effects. FIG. 32C shows APX3330 and CPI-613 EC50 (CalcuSyn). Figure d32D depicts Chou-Talalay Index (CI) of dose combinations (CalcuSyn). FIG. 32E depicts synergistic drug combinations (CalcuSyn) of APX3330 spiked with 50 uM CPI-613 or 75 uM CPI-613. Drug combination synergy was observed at APX3330 dosages of 75 uM and 50 uM when spiked with 50 uM CPI-613. Synergy was observed at all but one APX3330 dosage (6.3 uM) when spiked with 75 uM CPI-613. Data shown is the average of 3 separate cytotoxicity assays; each assay normalized to media only control.

Example 20

In this Example, the combination therapy of APX3330 and PDH and alpha-KDH Metabolic inhibitor, CPI-613, was analyzed for its tumor killing ability in human carcinoma colon cell line HCT-116.

HTC-116 (Yunhua Liu) was seeded in a 96-well tissue culture plate at 2000 cells/well in DMEM+10% FBS and grown overnight at 37° C., 5% $CO_2$. Drug Media DMEM+5% FBS was added at dosages of APX3330 (Apexian) from 100 uM to 0.4 uM in a 10-point spread and spiked with CPI-613 (Apexbio Technology) at 100 uM, or 75 uM, or alone for single agent. Cells were incubated for 72 hours at 37° C., 5% $CO_2$. Media was exchanged with DMEM+5% FBS+10% Alamar blue fluorescent cell viability indicator (INVITROGEN™) and incubated 4 hours at 37° C., 5% $CO_2$ and then read on a fluorescent reader (SYNERGY™ H4 BioTek). FIG. 33A shows APX3330 and CPI-613 single agent effects. FIG. 33B shows APX3330 and CPI-613 synergistic combo effects. FIG. 33C shows APX3330 and CPI-613 EC50 (CalcuSyn). FIG. 33D depicts Chou-Talalay Index (CI) of dose combinations (CalcuSyn). FIG. 33E depicts synergistic drug combinations (CalcuSyn) of APX3330 spiked with 100 uM CPI-613 or 75 uM CPI-613. Drug combination synergy was observed at all APX3330 dosages when spiked with 100 uM CPI-613. Synergy was observed at APX3330 dosages 100 uM-12.5 uM when spiked with 75 uM CPI-613. Data shown is the average of 3 separate cytotoxicity assays; each assay normalized to media only control.

Example 21

In this Example, the combination therapy of APX2014 and PDH and alpha-KDH Metabolic inhibitor, CPI-613, was analyzed for its tumor killing ability in human carcinoma colon cell line HCT-116.

HTC-116 (Yunhua Liu) was seeded in a 96-well tissue culture plate at 2000 cells/well in DMEM+10% FBS and grown overnight at 37° C., 5% $CO_2$. Drug Media DMEM+5% FBS was added at dosages of APX2014 (Apexian) in a 5-point spread from 25 uM to 1.6 uM and spiked with CPI-613 (Apexbio Technology) at 75 uM, or 50 uM, or alone for single agent. Cells were incubated for 72 hours at 37° C., 5% $CO_2$. Media was exchanged with DMEM+5% FBS+10% Alamar blue fluorescent cell viability indicator (INVITROGEN™) and incubated 4 hours at 37° C., 5% $CO_2$ and then read on a fluorescent reader (SYNERGY™ H4 BioTek). FIG. 34A shows APX2014 and CPI-613 single agent effects. FIG. 34B shows APX2014 and CPI-613 synergistic combo effects. FIG. 34C shows APX2014 and CPI-613 EC50 (CalcuSyn). FIG. 34D depicts Chou-Talalay Index (CI) of dose combinations (CalcuSyn). FIG. 34E depicts synergistic drug combinations (CalcuSyn) of APX2014 spiked with 50 uM CPI-613 or 75 uM CPI-613. Drug combination synergy could not be ascertained at APX2014 dosages when spiked with 50 uM CPI-613. Synergy was observed at only one APX2014 dosage (12.5 uM) when spiked with 75 uM CPI-613. Data shown is the average of 3 separate cytotoxicity assays; each assay normalized to media only control.

Example 22

In this Example, the combination therapy of APX3330 and GLS1 metabolic inhibitor, CB-839, was analyzed for its tumor killing ability in human carcinoma colon cell line HCT-116.

HTC-116 (Yunhua Liu) was seeded in a 96-well tissue culture plate at 2000 cells/well in DMEM+10% FBS and grown overnight at 37° C., 5% $CO_2$. Drug Media DMEM+5% FBS was added at dosages of APX3330 (Apexian) from 100 uM to 0.4 uM in a 10-point spread and spiked with CB-839 (Sigma-Aldrich) at 1000 nM, or 500 nM, or alone for single agent. Cells were incubated for 72 hours at 37° C., 5% $CO_2$. Media was exchanged with DMEM+5% FBS+10% Alamar blue fluorescent cell viability indicator (INVITROGEN™) and incubated 4 hours at 37° C., 5% $CO_2$ and then read on a fluorescent reader (SYNERGY™ H4 BioTek). FIG. 35A depicts APX3330 and CB-839 single agent effects. FIG. 35B depicts APX3330 and CB-839 synergistic combo effects. FIG. 35C shows APX3330 and CB-839 EC50 (CalcuSyn). FIG. 35D shows Chou-Talalay Index (CI) of dose combinations (CalcuSyn). FIG. 35E depicts synergistic drug combinations (CalcuSyn) of APX3330 spiked with 1000 nM CB-839 or 500 nM CB-839 (5-pt only). Drug combination synergy was observed at APX3330 dosages 100 uM-25 uM when spiked with 1000 nM. Synergy was observed at APX3330 dosages 100 uM-50 uM when spiked with 500 nM CB-839. Data shown is the average of 3 separate cytotoxicity assays; each assay normalized to media only control.

Example 23

In this Example, the combination therapy of APX3330 and cisplatin was analyzed for its tumor killing ability in the cisplatin resistant bladder cell line, BLCAb001.

The BLCAb001 (cisplatin resistant) cell line was treated with increasing concentrations of APX2014 and cisplatin as single agents and in combination and assayed in a 96-hour viability assay. The concentrations of APX2014 range from 6 mM-0.38 mM in combination with the indicated cisplatin doses (FIG. 36A). Doses of 6 mM-3 mM were shown to be synergistic with combination indexes of >1.0. The concentrations of Cisplatin as a single agent range from 2.5 mM-0.04 mM (FIG. 36B).

Example 24

In this Example, the combination therapy of APX3330 and cisplatin was analyzed for its tumor killing ability in the cisplatin resistant bladder cell line, BLCAb002.

The BLCAb002 (cisplatin sensitive) cell line was treated with increasing concentrations of APX2014 and cisplatin as single agents and in combination and assayed in a 96-hour viability assay. The concentrations of APX2014 range from 6 mM-0.38 mM in combination with the indicated cisplatin doses (FIG. 37A). Doses of 6 mM-1.5 mM were shown to be synergistic with combination indexes of >1.0. The concentrations of cisplatin as a single agent range from 2.5 mM-0.04 mM (FIG. 37B).

Example 25

In this Example, the combination therapy of APX2014 and napabucasin (STAT3 inhibitor) was analyzed for its tumor killing ability in the bladder cell line, T24.

T24 bladder cancer cells were treated with increasing concentrations of napabucasin in the presence or absence of APX2014 (2.5 or 5.0 mM) for 72 hours. The cells were then fixed, stained with methylene blue and relative cell number was calculated via spectrophotometry. Results are shown in FIGS. 38A & 38B.

Example 26

In this Example, the combination therapy of APX2009 and napabucasin (STAT3 inhibitor) was analyzed for its tumor killing ability in the bladder cell line, T24.

T24 bladder cancer cells were treated with increasing concentrations of napabucasin in the presence or absence of APX2009 (2.5 or 5.0 mM; 3.5 or 7 mM) for 72 hours. The cells were then fixed, stained with methylene blue and relative cell number was calculated via spectrophotometry. Results are shown in FIGS. 39A & 39B.

Example 27

In this Example, the combination therapy of APX2014 and napabucasin (STAT3 inhibitor) was analyzed for its tumor killing ability in the bladder cell line, SCaBER.

SCaBER bladder cancer cells were treated with increasing concentrations of napabucasin in the presence or absence of APX2014 (2.5 or 5.0 mM) for 72 Hrs. The cells were then fixed, stained with methylene blue and relative cell number was calculated via spectrophotometry. Results are shown in FIGS. 40A & 40B.

Example 28

In this Example, the combination therapy of APX2009 and napabucasin (STAT3 inhibitor) was analyzed for its tumor killing ability in the bladder cell line, SCaBER.

SCaBER bladder cancer cells were treated with increasing concentrations of napabucasin in the presence or absence of APX2009 (2.5 or 5.0 mM; 3.5 or 7 mM) for 72 hours. The cells were then fixed, stained with methylene blue and relative cell number was calculated via spectrophotometry. Results are shown in FIGS. 41A & 41B.

Example 29

In this Example, the combination therapy of APX2009 and CA9 inhibition was analyzed for its tumor killing ability in pancreatic ductal adenocarcinoma (PDAC).

Cell Culture: Low-passage patient-derived PDAC cell lines and pancreatic cancer-associated fibroblasts used in this Example were received from Dr. Anirban Maitra (The Johns Hopkins University) and maintained as described in Logsdon et al. (2016 Mol Cancer Ther 15(11):2722-2732), Fishel et al. (2011 Mol Cancer Ther 10(9):1698-1708), Su et al. (2011 Biochem 50:82-92), and Zhang et al. (2013 Biochem 52(17):2955-2966). Cells were submitted for STR analysis (CellCheck with IDEXX BioResearch) and were tested regularly for *mycoplasma* contamination. Cell lines were passaged fewer than 12 times before resuscitating fresh stocks. Hypoxic conditions in monolayer experiments were generated in a Ruskinn Invivo$_2$ 200 hypoxia work station (Baker Ruskinn; Sanford, ME) at 0.2% oxygen. Cell proliferation and viability in monolayer cultures was measured with alamarBlue assay. Growth of 3-dimensional tumor spheroid cultures was performed and quantified as described in Logsdon et al. (2016 Mol Cancer Ther 15(11):2722-2732), Sempere et al. (2011 Cancer Biol & Ther 12(3):198-207), and Arpin era al. (2016 Mol Cancer Ther 15(5):794-805).

Western Blot Analysis: Immunoblotting was performed using antibodies for APE1/Ref-1 (Novus Biologicals; Littleton, CO), CA9 (Santa Cruz; Dallas, Texas), Actin (Neo-Markers; Fremont, CA), and Vinculin (Sigma; St. Louis, MO). All samples were processed and run in parallel as described in Logsdon et al. (2016 Mol Cancer Ther 15(11):2722-2732) and Fishel et al. (2011 Mol Cancer Ther 10(9):1698-1708).

siRNA Transfections: PDAC cells were transfected with siRNA as previously described in Logsdon et al. (2016 Mol Cancer Ther 15(11):2722-2732), Fishel et al. (2011 Mol Cancer Ther 10(9):1698-1708), and Arpin era al. (2016 Mol Cancer Ther 15(5):794-805). siRNAs used were scrambled control and siAPE1/Ref-1 (SEQ ID NOS:1-3), as well as OriGene (Rockville, MD) Trisilencer siCA9.

Inhibitors: Small molecule inhibitors were prepared and used as previously described in Logsdon et al. (2016 Mol Cancer Ther 15(11):2722-2732), Fishel et al. (2011 Mol Cancer Ther 10(9):1698-1708), Su et al. (2011 Biochem 50:82-92), and Zhang et al. (2013 Biochem 52(17):2955-2966). APE1/Ref-1 redox signaling was inhibited using APX3330, APX2009, and APX2014 (Apexian Pharmaceuticals; Indianapolis, IN), with RN7-58 (Apexian Pharmaceuticals) used as a negative control that, although structurally similar, does not inhibit APE1/Ref-1 redox signaling activity (Shah et al. 2017 NPJ Precision Oncology 1; Kelley et al., 2017 Neural Regen Res 12(1):72-74; Kelley et al., 2016 J Pharmacol Exp Ther 359(2):300-039; Fishel et al., 2011 Mol Cancer Ther 10(9):1698-1708). CA9 inhibition was accomplished with SLC-0111 and FC12-531A (Logsdon et al. (2016 Mol Cancer Ther 15(11):2722-2732); Supuran et al., 2015 Expert Opinion on Drug Discovery 10(6):591-597; Chen et al., 2017 Am Soc Hematology; Koenig et al., 2017 Experimental Hematology 53, S88; Fishel et al. (2011 Mol Cancer Ther 10(9):1698-1708). All of these compounds have been administered in mice with minimal toxicity, though ongoing studies are evaluating their safety and efficacy alone and in combination with other agents in vivo.

ChIP Assay: Chromatin Immunoprecipitation (ChIP) was performed using the *Magna* ChIP kit (Millipore). Immunoprecipitation (IP) was performed using polyclonal antibodies for HIF1α (Novus) or Rabbit IgG control (Millipore). Binding to the HIF-1-Binding Site (HBS) in the CA9 promoter was measured via qPCR using SYBR Green master mix (Applied Biosystems) in a CFX96 Real-Time System (Bio-Rad). Primer sequences used for ChIP qPCR were: CA9 HBS-Fwd (5'-CTCACTCCACCCCCATCCTA-3')(SEQ ID NO:32) and CA9 HBS-Rev (5'-GGACCGAGG-GAGACAACTAG-3') (SEQ ID NO:33). 1% of the cross-linked DNA from each sample was evaluated (without IP) as a control to normalize the qPCR signal across samples (Input).

pH Assay: Intracellular pH was measured with pHrodo Red AM Intracellular pH Indicator (LifeTech) as described in Logsdon et al. (2016 Mol Cancer Ther 15(11):2722-2732). Fluorescent images of pHrodo Red AM-exposed cells were captured with a confocal/two-photon Olympus Fluoview FV-1000 MPE system (Olympus Scientific Solutions America; Waltham, MA) at the Indiana Center for Biological Microscopy facility (Indianapolis, IN) as previously described in Logsdon et al. (2016 Mol Cancer Ther 15(11):2722-2732).

qRT-PCR: mRNA levels were measured using qRT-PCR as previously described in Logsdon et al. (2016 Mol Cancer Ther 15(11):2722-2732), Fishel et al. (2011 Mol Cancer Ther 10(9):1698-1708), Fischer et al. (2015 J Biol Chem 290(5):3057-3068). The comparative Ct method was used to quantitate mRNA levels using RPLP0 and B2M as reference genes. The primers for CA9, RPLP0, and B2M are commercially available (Applied Biosystems). Experiments were performed in triplicate for each sample.

Immunohistochemistry (IHC): 3D spheroid cultures were collected on day 12 after plating, fixed with 4% paraformaldehyde (PFA) (Electron Microscopy Sciences; Hatfield, PA), and permeabilized with 70% ethanol. Fixed/permeabilized 3D cultures were solidified in HistoGel (LifeTech). HistoGel plugs were paraffin embedded and slides were prepared by the laboratory of Dr. Keith Condon (Indiana University School of Medicine; Indianapolis, IN). Samples were stained with the specified antibodies by the Indiana University School of Medicine Research Immunohistochemistry Facility (Indianapolis, IN).

Statistical Analysis: Comparisons in experiments with more than two groups were analyzed with post-hoc Multiple Comparisons Tests (Tukey, Dunnett, or Sidak as appropriate) Logsdon et al. (2016 Mol Cancer Ther 15(11):2722-2732), McHugh (2011 Biochem 21(3):203-209), and Stevens et al. (2017 PloS One 12(4):e0176124). Differences between groups were considered significant if $p<0.05$. Statistical analyses were performed with Microsoft Excel and Prism (Version 6.0f, Copyright ©2014 GraphPad Software Inc. La Jolla, CA).

Results

APE1/Ref-1-HIF-1-CA9 Signaling Axis in PDAC Cells

To characterize the response of different PDAC patient lines to APE1/Ref-1 and/or CA9 inhibition, the effects of inhibition of CA9 via small molecule inhibitor, SLC-0111, or siRNA were evaluated in patient-derived cells. Although CA9 is well-established as a hypoxia-regulated enzyme, the level of CA9 expression induced under hypoxic conditions is variable between patient lines. Therefore, the relative CA9 expression in a selection of low-passage patient-derived PDAC cell lines (10.05, Pa02C, and Pa03C) was determined following 24 hrs exposure to 0.2% oxygen, as compared to cells incubated in normoxic conditions. Hypoxia exposure significantly induced CA9 protein levels in all cell lines (2.5-21.5-fold), including cancer-associated fibroblast cells (CAF19) (FIG. 42A). However, CA9 was most strongly induced in the 10.05 cells (21.5-fold over normoxia), and Pa03C cells had the lowest levels of hypoxia-induced CA9 protein (2.5-fold over normoxia). Notably, APE1/Ref-1 expression was not significantly affected by hypoxia exposure in these cells. The majority of mechanistic experiments were evaluated in 10.05 cells because of their robust CA9 induction and were repeated in the CA9-weak Pa03C cells to confirm and compare responses.

The efficacy of SLC-0111, a CA9 inhibitor that has recently completed a Phase I clinical trial, was evaluated in different PDAC cell lines under hypoxic conditions for comparison. While all three of the patient-derived PDAC cell lines tested had $LC_{50}$s for SLC-0111 below 100 µM during hypoxia exposure (FIG. 42B), the most sensitive cell line was 10.05, which induces CA9 expression to the highest level following hypoxia exposure (FIG. 42A). In fact, CA9 protein induction under hypoxia was inversely correlated with SLC-0111 $LC_{50}$ under hypoxia in the cell lines tested ($R^2 > 0.99$) (FIG. 42B), indicating that increased CA9 induction may predict increased sensitivity to CA9 inhibition in PDAC cells.

Induction of CA9 in pancreatic cancer cells grown in monolayer versus 3D tumor spheroids were compared. Following exposure to ~0.2% hypoxia using a hypoxic chamber in the 10.05 monolayer cultures, CA9 was induced ~21-fold (FIGS. 42A and 42C). Using the 3D tumor spheroid system with and without CAFs, CA9 expression was further increased 2.5 and 6.2-fold, respectively, over hypoxic monolayer cultures despite these spheroid cultures being grown in normoxic conditions (FIG. 42C). Based on the relevance of the 3D culture model, the effects of inhibition of CA9 and APE1/Ref-1 were further evaluated in this system.

Figure 1:
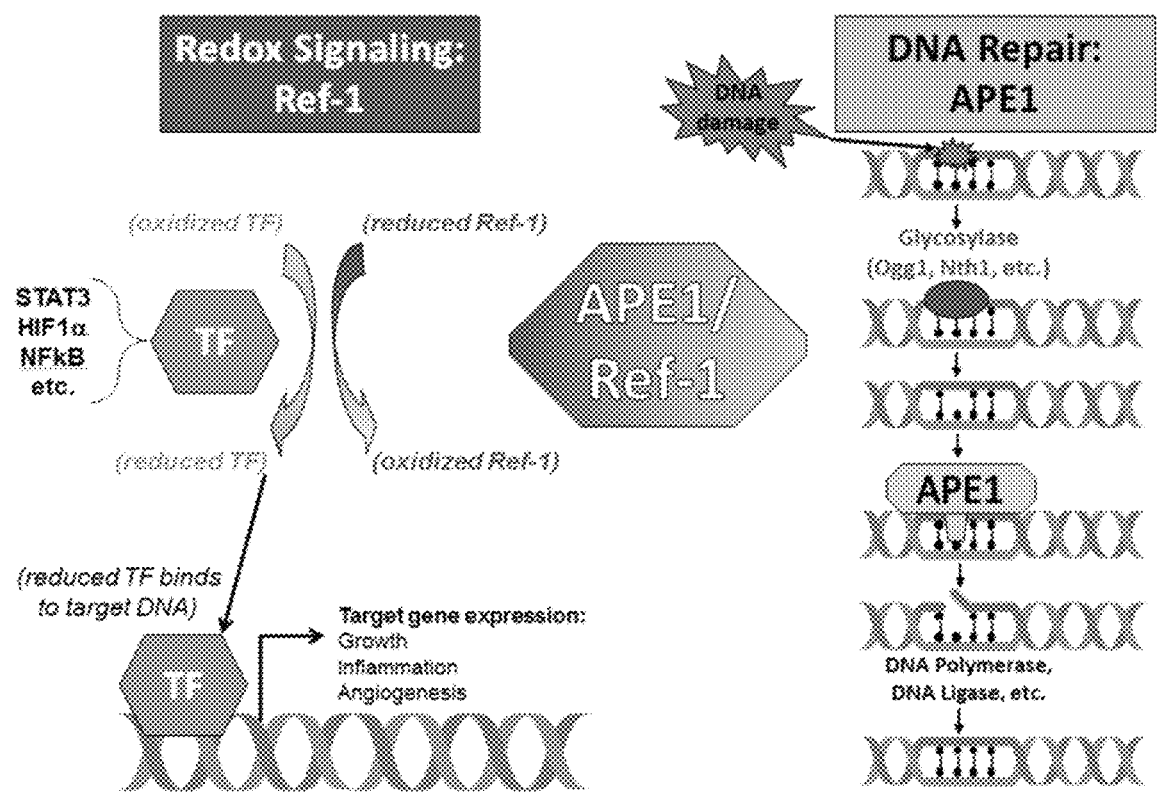
FIG. 1 depicts the dual functions of APE1/Ref-1. APE1/Ref-1 is a multifunctional protein involved in redox signaling and DNA repair. The redox signaling function (Ref-1) is responsible for reduction of oxidized cysteine residues in certain transcription factors (TF's), leading to increased transcriptional activity and upregulation of genes involved in cell growth, inflammation, angiogenesis, and other cellular functions. The DNA repair function (APE1) is responsible for the endonuclease activity in base excision repair, cutting the phosphodiester backbone of DNA at abasic sites created by glycosylases. These cuts allow the abasic sites to be replaced with appropriate nucleotide bases, completing the DNA base excision repair process.

Knockdown of APE1/Ref-1 and CA9 expression was evaluated in 3D spheroid cultures to determine whether the growth and survival of PDAC cells in this relevant microenvironment was dependent upon CA9 and APE1/Ref-1 expression. Spheroids were collected on day 8 to confirm the continued knockdown of CA9 and APE1. Each siRNA significantly reduced the expression of its target gene/enzyme product, confirming the continued knockdown of these enzymes throughout the duration of the 3D cultures. APE1/Ref-1 knockdown also decreased CA9 expression to a similar extent to that seen in siCA9 cultures (FIG. 42D FIG. 1D). Reduced levels of APE1/Ref-1 and/or CA9 significantly slowed 3D tumor spheroid growth by ~50-80% ($p<0.001$) as measured by fluorescence intensity and area (FIGS. 42E and 42F). These results confirm the importance of APE1/Ref-1 and CA9 expression in PDAC tumor growth. Additionally, APE1/Ref-1 knockdown slowed 3D tumor spheroid growth significantly more than CA9 knockdown, which indicated that inhibition of CA9 alone may not be as efficient at attenuating PDAC tumor growth as dual-targeting these enzymes.

Inhibition of APE1/Ref-1 redox signaling decreased HIF-1-mediated CA9 transcription and subsequent expression (FIG. 42D). To determine whether this was the result of a direct effect on HIF1α binding to the CA9 promoter, a chromatin immunoprecipitation (ChIP) assay was performed to investigate HIF-1-DNA interactions. 10.05 cells were treated with the APE1/Ref-1 redox signaling inhibitor APX3330 and exposed to 0.2% 02 for 12 hrs. Immunoprecipitations (IPs) of HIF1α demonstrated a 4.3-fold increase in HIF1α binding to the HIF-1-Binding Site (HBS) in the CA9 promoter under hypoxic conditions, which was decreased by ~60% in cells treated with APX3330 (FIGS. 42G and 42H). These data demonstrate that HIF1α interactions with the CA9 promoter were induced by hypoxia, and that these hypoxia-induced interactions were attenuated by APE1/Ref-1 redox signaling inhibition, providing further confirmation of the mechanism by which APE1/Ref-1 redox signaling regulates HIF-1-mediated CA9 transcription under hypoxic conditions.

Blockade of CA9 Via APE1/Ref-1 or CA9 Inhibition

To determine target selectivity, analogs of APX3330, APX2009 and APX2014, and an analog of SLC-0111, FC12-531A, were used. All of which demonstrated improved cytotoxicity over their parent compounds under hypoxic conditions (Table 7).

Hypoxia-induced CA9 mRNA and protein levels were evaluated in 10.05 cells following treatment with APX3330, APX2009, APX2014, and the inactive analog RN7-58. Inhibition of APE1/Ref-1 with all three inhibitors resulted in concentration-dependent decreases in hypoxia-induced CA9 mRNA and protein levels, with 10-fold less required for APX2009 and APX2014 vs. APX3330 (FIGS. 43A and 43B), indicating that these analogs were more potent inhibitors of APE1/Ref-1 redox signaling than APX3330. The inactive analog (RN7-58) did not affect hypoxia-induced CA9 expression even at 100 µM, further confirming the selective contribution of APE1/Ref-1 redox signaling activity to the effects seen with the other compounds.

The effect of APE1/Ref-1 redox inhibition on CA9 protein expression was also measured in 3D tumor spheroids. 10.05 cells were grown in 3D cultures for 12 days and treated on days 4 and 8 with APX3330, APX2009 and APX2014, or the inactive analog (RN7-58). APE1/Ref-1 redox inhibition significantly decreased the expression of CA9 protein in 3D tumor cultures in a concentration-dependent manner (FIG. 43C). Importantly, the APX2009 and APX2014 APE1/Ref-1 inhibitors required 10-fold less of the concentration compared to APX3330 to attenuate CA9 expression in the spheroid cultures, further validating the potency of these compounds. The inactive analog (RN7-58) did not affect CA9 expression in PDAC spheroid cultures, once again corroborating the specificity of the effects of the APE1/Ref-1 redox signaling inhibitors on HIF1α activity.

CA9 expression is important for tumor cell growth, and CA9 functions by stabilizing intracellular pH to counteract the acidification that occurs in response to metabolic changes under hypoxic conditions. As a functional marker for CA9 activity, the effects of CA9 on intracellular pH were evaluated. Hypoxia exposure (0.2% 02 for 48 hrs) did not significantly affect intracellular pH in 10.05 cells (FIGS. 43D and 43E), indicating that these cells compensate for the effects of hypoxia on pH. However, when CA9 expression was reduced via siRNA, the result was a significant decrease in intracellular pH in hypoxia-exposed cells, as measured by increased fluorescence of the pH-sensitive pHrodo Red AM dye (FIGS. 43D and 43E). These data support the conclusion that CA9 is responsible for regulating pH in these cells.

APX3330 and SLC-0111 did not affect intracellular pH as single-agents at concentrations up to 50 µM APX3330 or 100 µM SLC-0111, instead requiring the combination of both compounds to acidify hypoxic PDAC cells. Therefore, the APX3330 analogs, APX2009 and APX2014, were used to determine whether APE1/Ref-1 redox inhibition alone can shift intracellular pH in hypoxic PDAC cells given a sufficiently potent inhibitor. Treatment with either 8 APX2009 or 5 µM APX2014 alone resulted in a significant increase in fluorescence (normalized to cell survival), indicating decreased intracellular pH with single-agent APE1/Ref-1 redox signaling inhibition (FIGS. 2D-2E). Due to the decrease in CA9 expression following APE1/Ref-1 inhibition, these data show that APE1/Ref-1 redox signaling inhibition alone was sufficient to acidify cells. Taken together, the data in FIGS. 43D and 43E indicated that decreases in CA9 expression via either siRNA or APE1/Ref-1 redox inhibition resulted in intracellular acidification in hypoxic PDAC cells.

Following these mechanistic results, the effects of the APE1/Ref-1 redox signaling inhibitors, APX2009 and APX2014, were compared to APX3330 in 3D PDAC tumor+CAF co-cultures using 10.05 (FIG. 43F) or Pa03C (FIG. 43G) tumor cells. Each of these analogs exhibited $LC_{50}$s between 4-50-fold lower than APX3330 in this 3D tumor spheroid model (Table 7), suggesting that they have improved potency in their tumor growth-inhibitory effects compared to APX3330. Similarly, a more potent analog of CA9 inhibitor, SLC-0111, FC12-531A exhibited $LC_{50}$s ~15-fold lower than SLC-0111 in this 3D tumor spheroid model (FIGS. 43H and 43I, Table 7), demonstrating improved potency in its tumor growth-inhibitory effects over SLC-0111. Surprisingly, as shown in Table 7, APX2009 and APX2014 were more potent as single agents compared to the parent compound, APX3330. In combination studies, the analogs, APX2009 and APX2014, could be used at much lower concentrations to achieve a better combinatory effect.

TABLE 7

|  |  |  | Panc10.05 | Pa03C |
|---|---|---|---|---|
| Monolayer (Hypoxia) |  | APX3330 | 40.3 | 50.2 |
|  |  | APX2009 | 4.9 | 6.7 |
|  |  | APX2014 | 1.3 | 3.5 |
|  |  | SLC-0111 | 63.9 | 90.8 |
|  |  | FC12-531A | 1.4 | 1.1 |
| 3D Cultures | Tumor Alone | APX3330 | 44.5 | 37.9 |
|  |  | APX2009 | 9.4 | 6.9 |
|  |  | APX2014 | 0.3 | 1.1 |
|  |  | SLC-0111 | 64.0 | 51.9 |
|  |  | FC12-531A | 4.8 | 3.0 |
|  | Tumor + CAFs | APX3330 | 57.9 | 41.6 |
|  |  | APX2009 | 13.0 | 8.4 |
|  |  | APX2014 | 1.2 | 2.4 |
|  |  | SLC-0111 | 70.8 | 64.1 |
|  |  | FC12-531A | 4.9 | 3.8 |
|  | CAFs | APX3330 | 59.4 | 57.3 |
|  |  | APX2009 | 14.1 | 13.1 |
|  |  | APX2014 | 6.3 | 7.1 |
|  |  | SLC-0111 | 98.2 | 97.0 |
|  |  | FC12-531A | 4.6 | 5.3 |

Figures 44A, 44B, 44C, 44D, 44E, 44F:
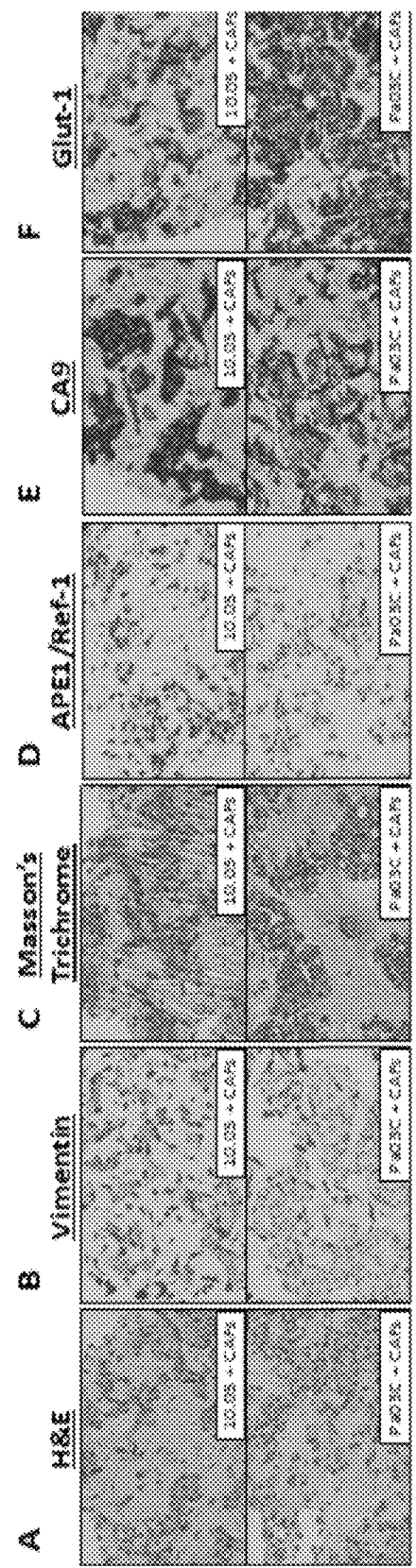

*N = 3
** All concentrations are μM
****3D culture data calculated from D12 curves Effect of dual-targeting APE1/Ref-1 and CA9 in 3D Cultures Characterization of 3D spheroid cultures was performed using H&E staining, Vimentin (to detect CAFs within the co-cultures), and Masson's Trichrome (FIGS. 44A-44C). These data indicated that the tumor cells were more densely packed than the CAFs in the 3D co-cultures, and the Masson's Trichrome stain indicated that the CAFs deposit extracellular matrix (ECM) components such as collagen, validating this model as representative of the fibrotic tumors seen in PDAC patients. Notably, APE1/Ref-1 staining was primarily nuclear and appeared to be uniform in tumor cells throughout the cultures in all 3D cultures tested (FIG. 44D). Furthermore, the hypoxia markers CA9 and Glucose Transporter 1 (Glut-1) showed positivity in distinct regions (FIGS. 44E and 44F), indicating differential zones of hypoxia within the spheroid cultures. These data demonstrated that culturing PDAC cells in this 3D tumor spheroid model resulted in hypoxic cells that expressed CA9 without the need for external induction of low-oxygen conditions.

APE1/Ref-1 redox signaling inhibition sensitized 3D PDAC tumor spheroids to CA9 inhibition with second-generation inhibitors Combination treatment with APX3330 and SLC-0111 significantly attenuated tumor cell growth with minimal effects on the CAFs in the spheroid co-cultures at Day 12 of co-culture in 3D co-cultures containing both PDAC tumor cells and CAFs. To characterize the growth inhibitory effects of the compounds over time and determine the optimal regimen, the time in culture was extended to 16 days and assayed for growth after each treatment. The combination therapy was more effective than monotherapy in both patient-derived cell lines. SLC-0111 was also combined with APX2009 at 10 μM or APX2014 at 0.6 μM in 3D co-cultures, which showed similar results as with APX3330 at 50 μM.

To further determine the effects of CA9 inhibition and APE1/Ref-1 inhibition in PDAC cells, the SLC-0111 analog, FC12-531A, was employed, which showed the same trend as SLC-0111 in the tumor cells in this model, but with substantially lower concentrations needed to achieve similar effects (3 μM FC12-531A vs. 50 μM SLC-0111). Specifically, 3 μM FC12-531A monotherapy significantly affected tumor cell growth in Pa03C co-cultures, but not in 10.05 co-cultures, and FC12-531A significantly enhanced the effects of APX3330, APX2009, and APX2014 on 3D tumor cell growth in both 10.05 and Pa03C co-cultures (FIGS. 45A-45R). These data validate results showing enhanced PDAC tumor cell killing with dual-targeting of APE1/Ref-1 redox signaling and CA9 activity while moving forward with novel inhibitors that have improved potency, allowing for nanomolar-to-low-micromolar concentrations of each drug used with the most potent combination (0.6 μM APX2014+3 μM FC12-531A, FIGS. 4M-4R).

These results demonstrate an arm of the APE1/Ref-1 regulatory node connecting APE1/Ref-1 redox signaling through HIF-1-mediated transcription to CA9 expression and activity (FIG. 46). Specifically, the results presented herein expand the significance of this signaling axis using novel analogs of clinical compounds to dual-target APE1/Ref-1 redox signaling and CA9 activity in 3D PDAC tumor cultures, resulting in enhanced killing of tumor cells in spheroid co-cultures. The results presented herein also show for the first time that hypoxia-induced interactions between HIF-1 and the promoter of one of its major transcriptional targets are decreased following APE1/Ref-1 redox signaling inhibition (FIG. 42C), providing a key bridge in the understanding of APE1/Ref-1 contributions to HIF-1-mediated transcription.

What is claimed is:

1. A method of treating retinopathy of prematurity (ROP) in a subject in need thereof, the method comprising administering to the subject [(2E)-2-[(3-methoxy-1,4-dioxo-1,4-dihydronaphthalen-2-yl)methylidene]-N,N-diethylpentanamide] (APX2009).

2. The method as set forth in claim 1 further comprising administering a second therapeutic agent.

3. The method as set forth in claim 2, wherein the second therapeutic agent is selected from the group consisting of doxorubicin, endostatin, 5-fluorouracil (5-FU), bortezomib, ispinesib mesylate, SN-38, topotecan, paclitaxel, bryostatin 1, trametinib, LAQ824, vinblastine, BEZ235, panobinostat, methotrexate, temsirolimus, FK866, afatinib, tozasertib, irinotecan, GSK2126458, CPI-613, γ-secretase inhibitors, DLL4-inhibiting antibodies, and combinations thereof.

4. A method of treating neovascularization in a subject in need thereof, the method comprising administering to the subject [(2E)-2-[(3-methoxy-1,4-dioxo-1,4-dihydronaphthalen-2-yl)methylidene]-N,N-diethylpentanamide] (APX2009).

5. The method as set forth in claim 4, wherein the neovascularization is selected from the group consisting of retinal neovascularization and choroidal neovascularization (CNV).

6. The method as set forth in claim 4 further comprising administering a second therapeutic agent.

7. The method as set forth in claim 6, wherein the second therapeutic agent is selected from the group consisting of doxorubicin, endostatin, 5-fluorouracil (5-FU), bortezomib, ispinesib mesylate, SN-38, topotecan, paclitaxel, bryostatin 1, trametinib, LAQ824, vinblastine, BEZ235, panobinostat, methotrexate, temsirolimus, FK866, afatinib, tozasertib, irinotecan, GSK2126458, CPI-613, γ-secretase inhibitors, DLL4-inhibiting antibodies, and combinations thereof.

* * * * *